United States Patent [19]
Andrews et al.

[11] Patent Number: 5,506,117
[45] Date of Patent: Apr. 9, 1996

[54] BIOCHEMICAL PROCESS FOR GROWING LIVING CELLS BY MEASURING THE AMOUNT OF NUTRIENT ADDED TO THE REACTION MEDIUM

[75] Inventors: Frank T. Andrews, Kailua, Hi.; William A. Farone, Costa Mesa, Calif.

[73] Assignees: Cytokinetics, Inc., Kailua, Hi.; Applied Power Concepts, Inc., Orange, Calif.

[21] Appl. No.: 151,217

[22] Filed: Nov. 12, 1993

Related U.S. Application Data

[63] Continuation-in-part of Ser. No. 423,800, Oct. 18, 1989, Pat. No. 5,346,826, and Ser. No. 628,321, Dec. 17, 1990, Pat. No. 5,262,961.

[51] Int. Cl.$^6$ .............................. C12Q 1/02; C12N 5/00
[52] U.S. Cl. .......... 435/29; 435/34; 435/240.241; 435/240.25; 435/240.4; 435/240.46; 435/243; 435/244; 435/245
[58] Field of Search ............... 435/29, 34, 240.241, 435/244, 245, 291, 240.25, 240.4, 240.46, 243, 282

[56] References Cited

U.S. PATENT DOCUMENTS

| | | |
|---|---|---|
| 3,814,670 | 6/1974 | Freake et al. . |
| 3,888,741 | 6/1975 | Freake et al. . |
| 3,968,010 | 7/1976 | Young . |
| 4,275,164 | 6/1981 | Masurekar .......................... 435/227 |
| 4,673,638 | 6/1987 | Grosch et al. ........................ 435/34 |
| 4,988,443 | 1/1991 | Michaels et al. .................... 435/182 |
| 4,999,298 | 3/1991 | Wolfe et al. .................... 435/240.242 |
| 5,079,161 | 1/1992 | Mitsuda et al. ................ 435/240.23 |
| 5,139,946 | 8/1992 | Howell et al. .................. 435/240.2 |
| 5,262,961 | 11/1993 | Farone ................................ 364/500 |
| 5,286,646 | 2/1994 | Kearns et al. ................ 435/240.24 |

OTHER PUBLICATIONS

Biotech Abs. 89–08820 Garn et al "Eur Congr. Biotech" (1987) vol. 3 #92.
Biotech Abs 89.06204 EP–306466 Public, Date Mar. 8, 1989
Waser "Quantit. Chem" Publis W.A.–Benjamin 1964 pp. 230–242.

*Primary Examiner*—Herbert J. Lilling
*Attorney, Agent, or Firm*—John J. Connors; Connors & Associates

[57] ABSTRACT

Disclosed is a process for growing living cellular material in a reaction zone having a membrane in contact with an aqueous medium. The concentration of nutrient in samples from the process is measured using a spectrometric instrument to obtain spectral data characteristic of nutrient components. This spectral data is analyzed using a chi-squared mathematical technique to determine the unknown concentration of nutrient components in said samples. Then the rate at which nutrient is fed to the reaction zone is altered based on the determination of concentration of nutrient components as required to optimize the process.

16 Claims, 39 Drawing Sheets

.25% Fructose in Water

.25% Fructose in Water

.25% Fructose in Water

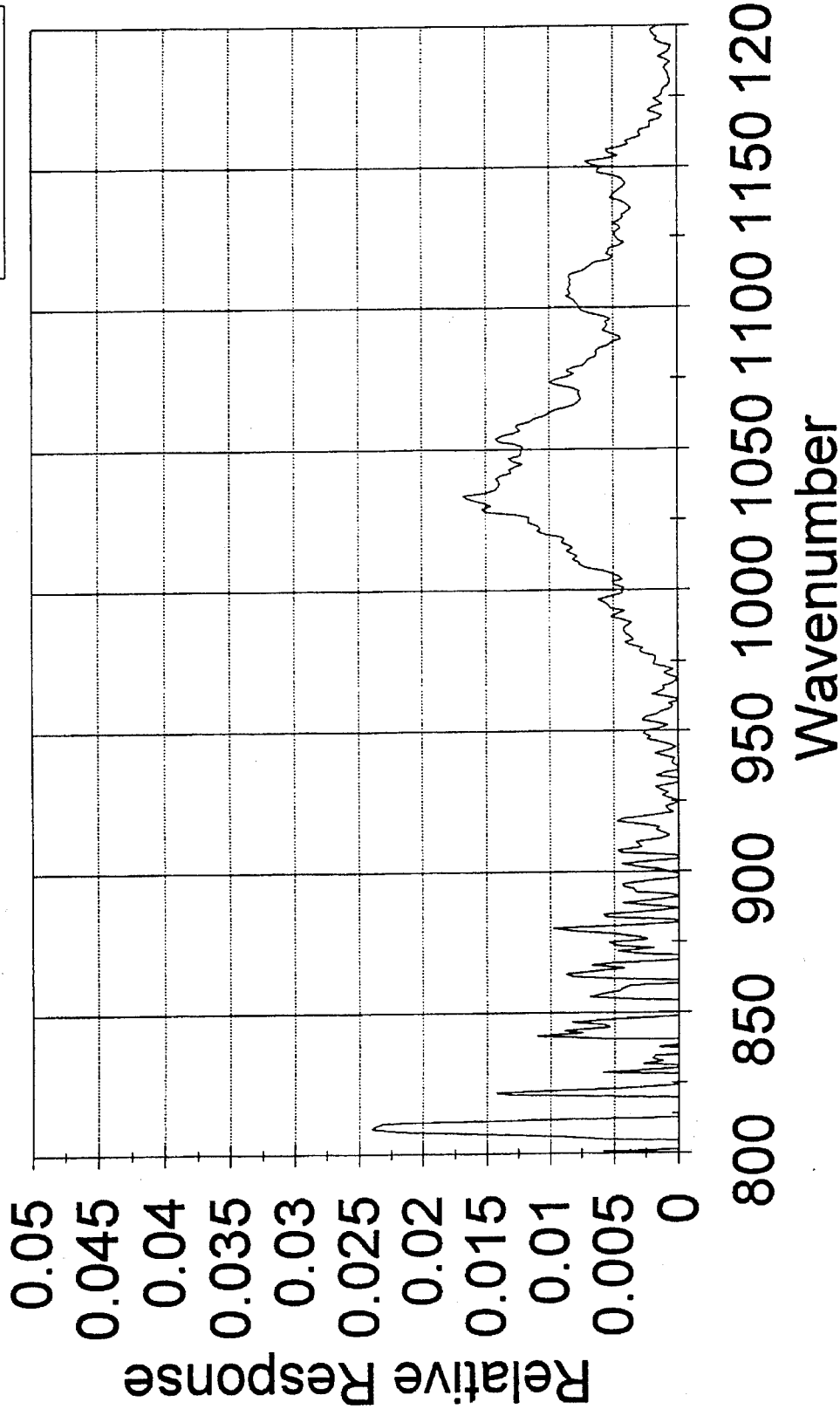

.5% Glucose in Water

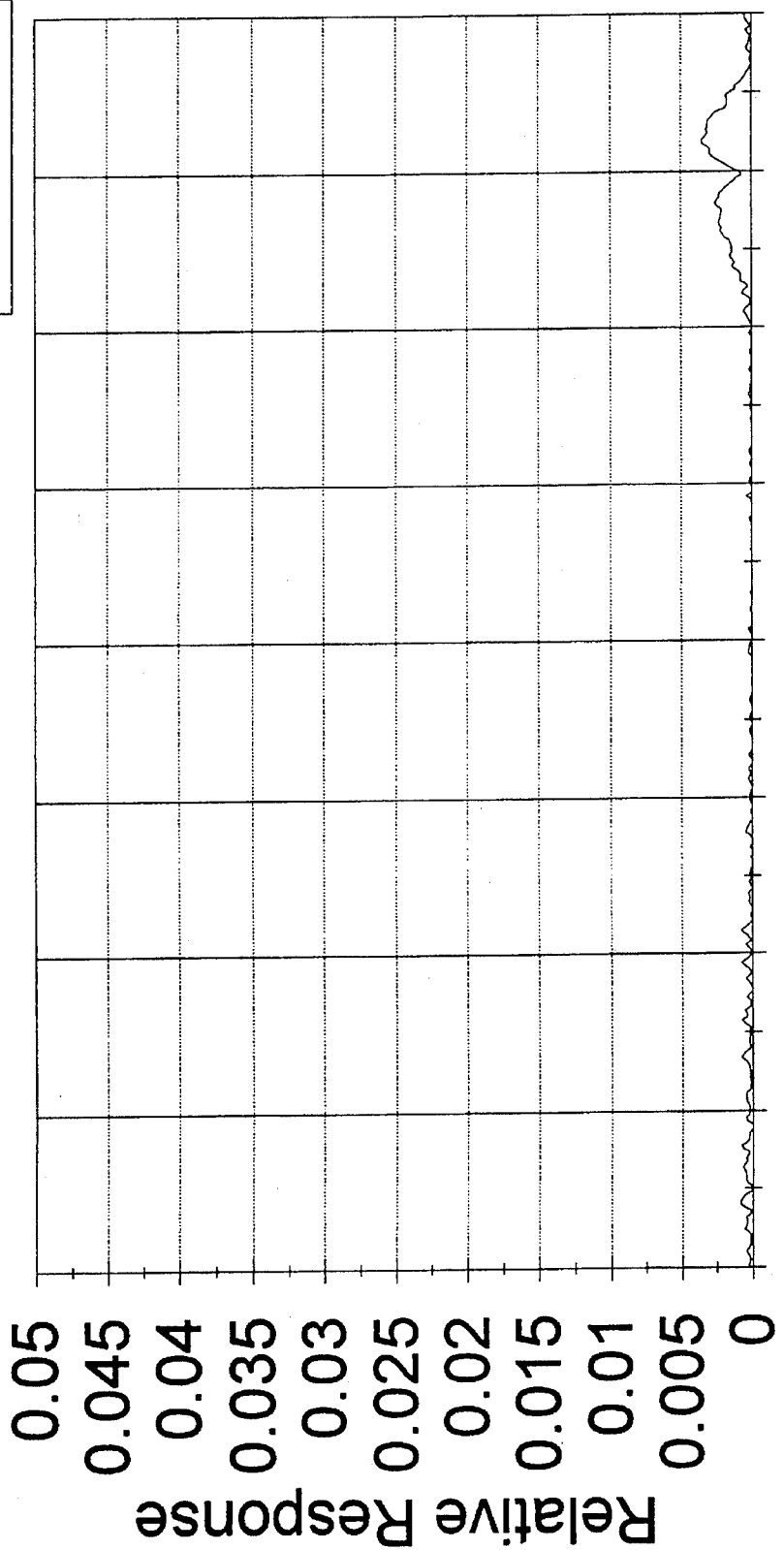

.5% Glucose in Water

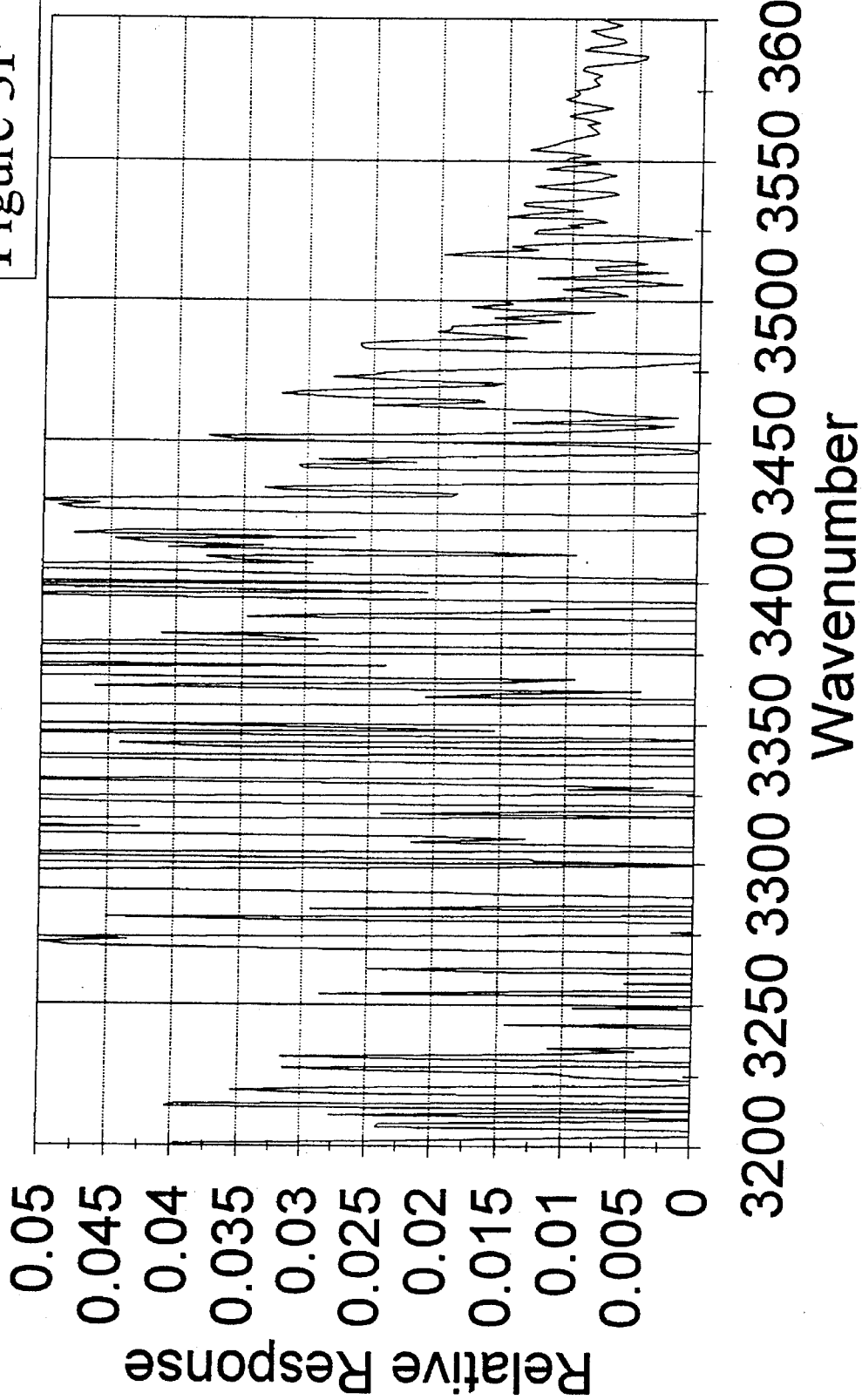

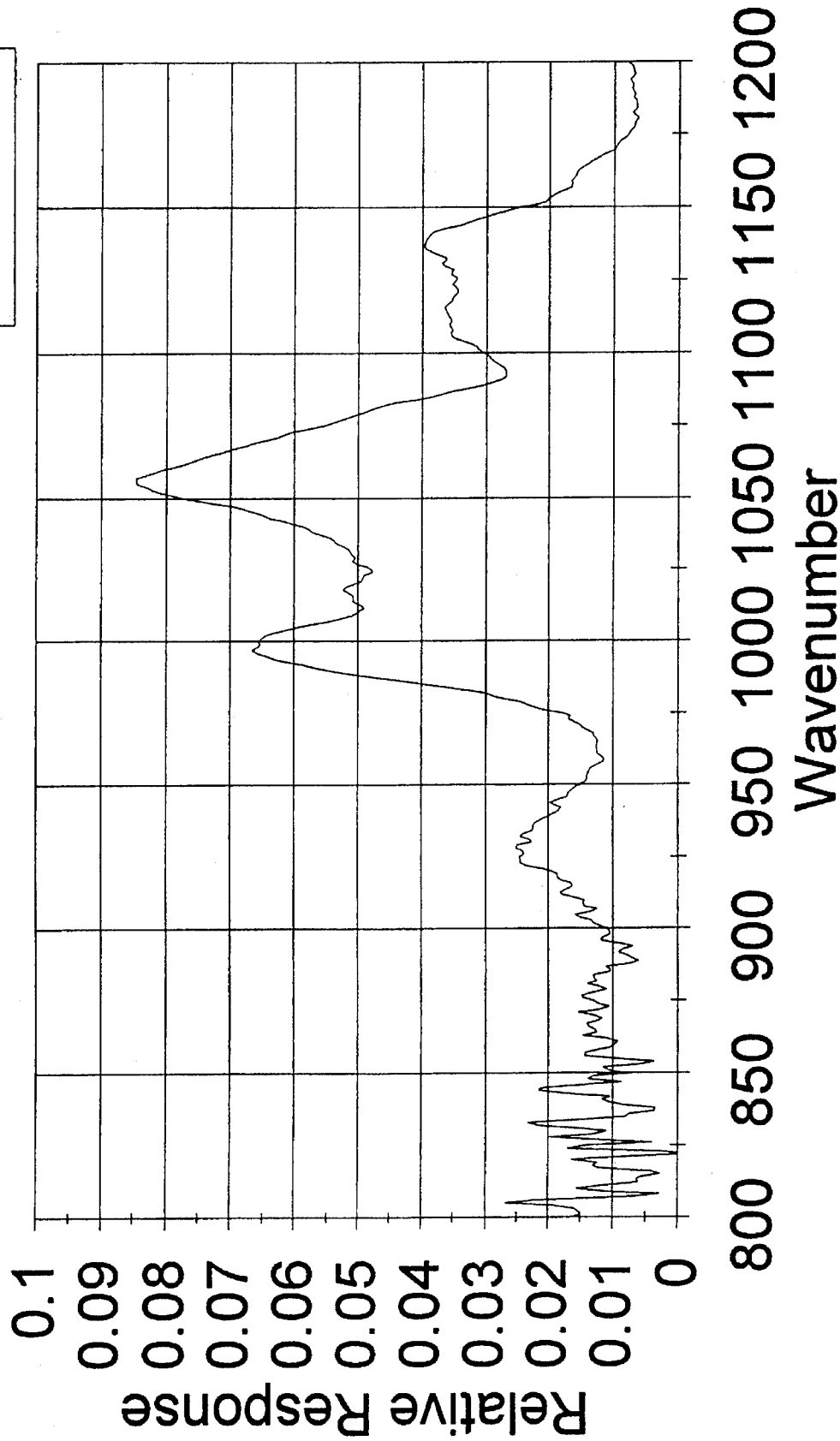

3% Sucrose in Water

3% Sucrose in Water

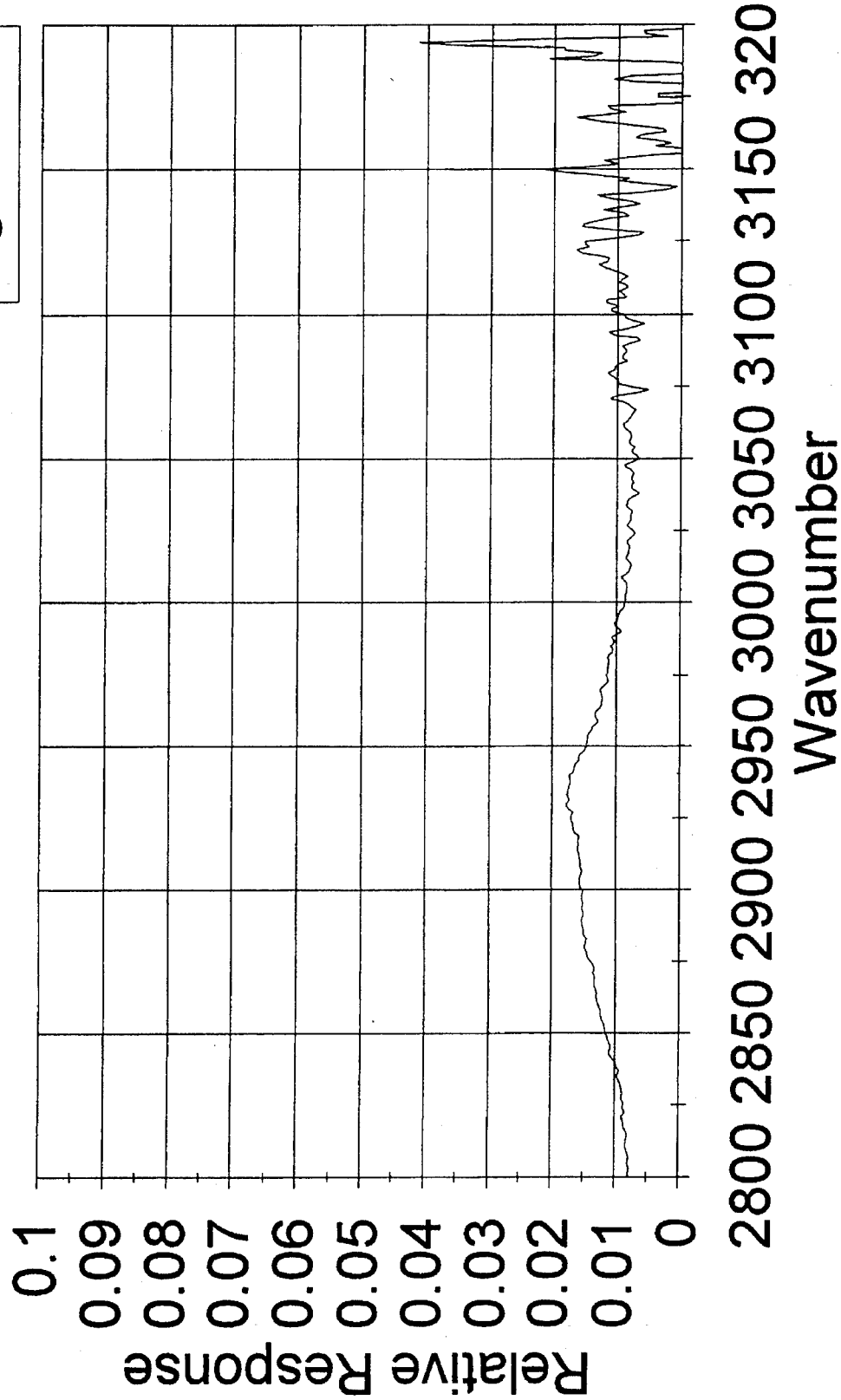

3% Sucrose in Water

3% Sucrose in Water

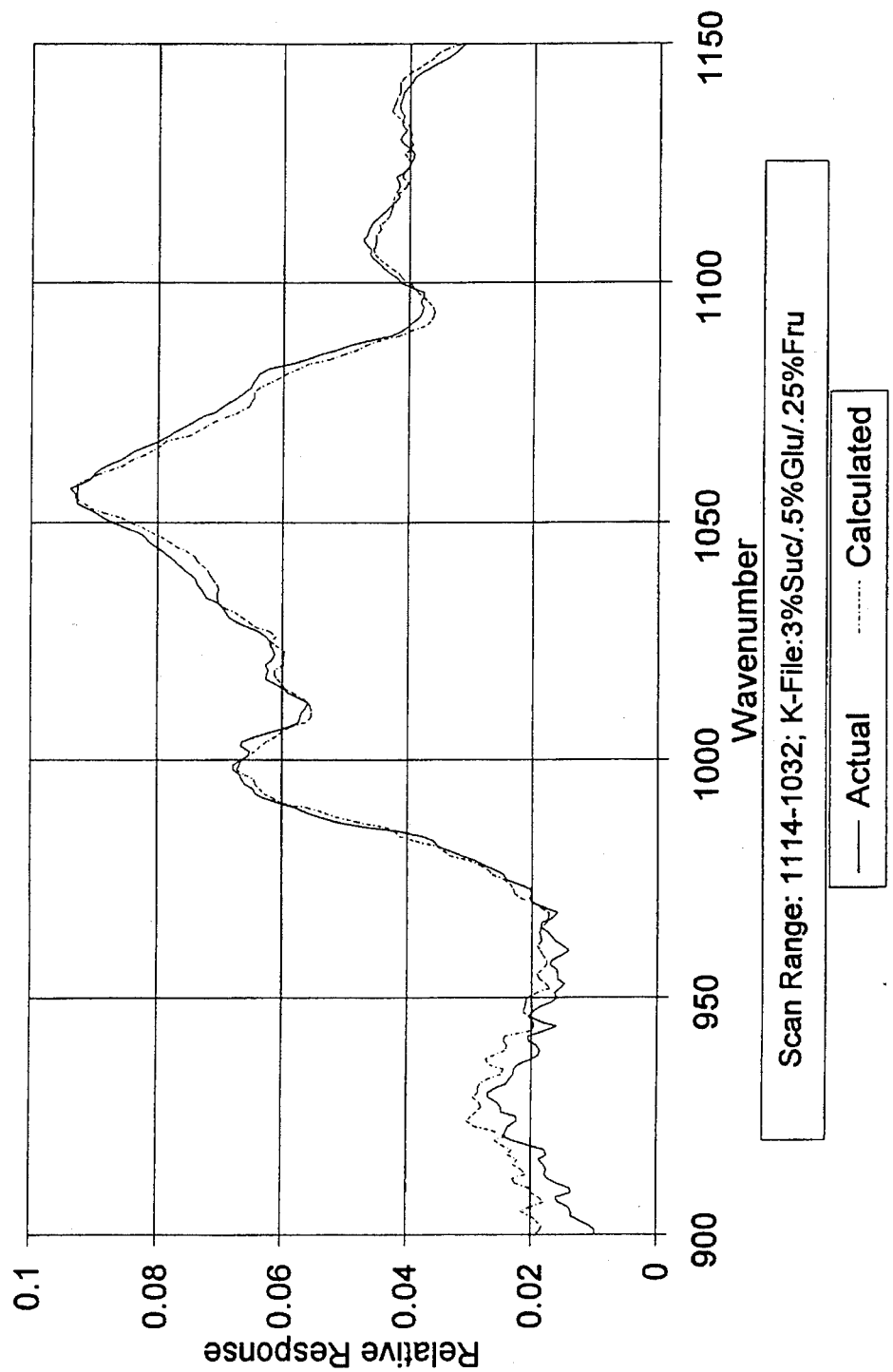

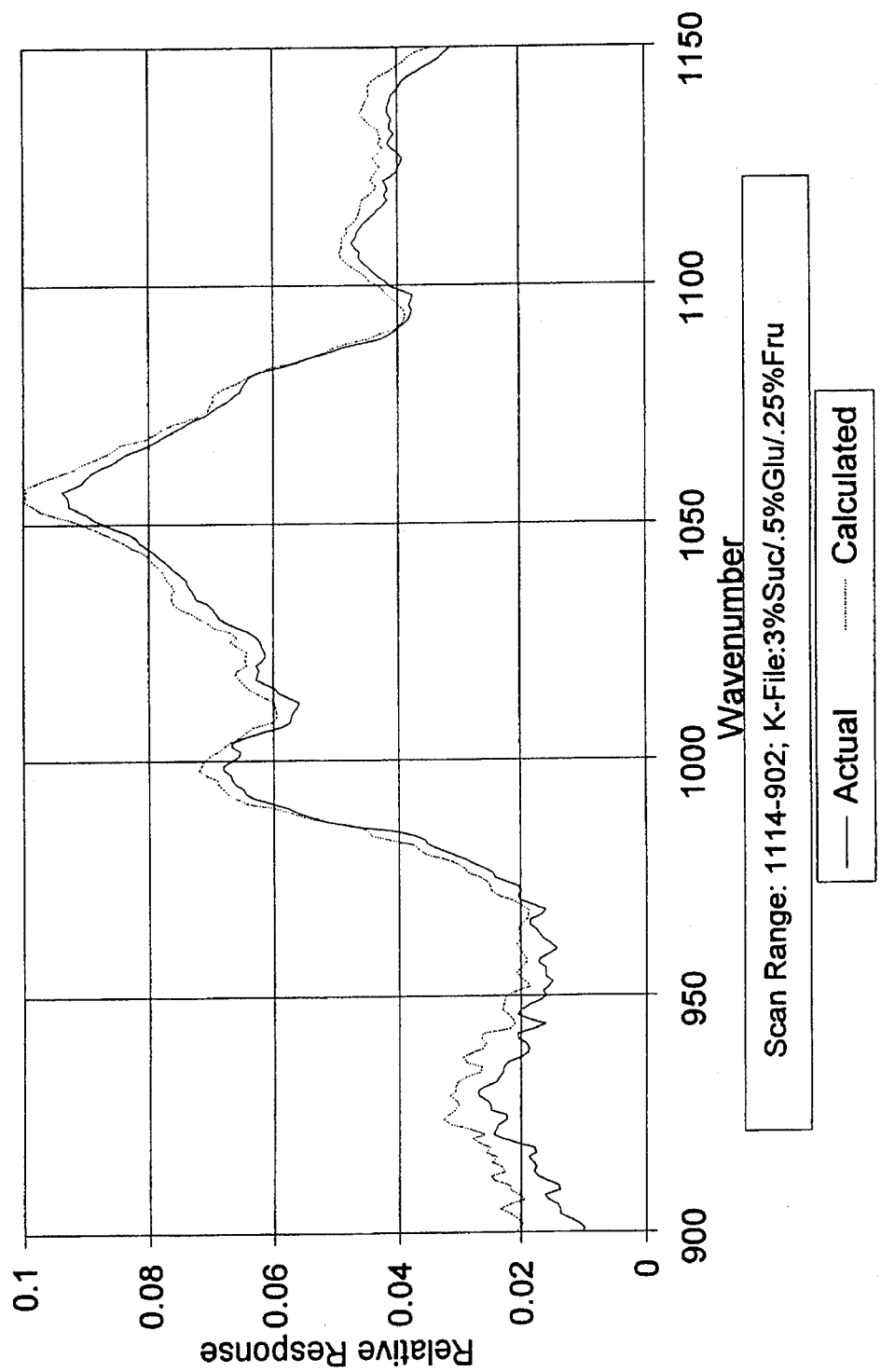

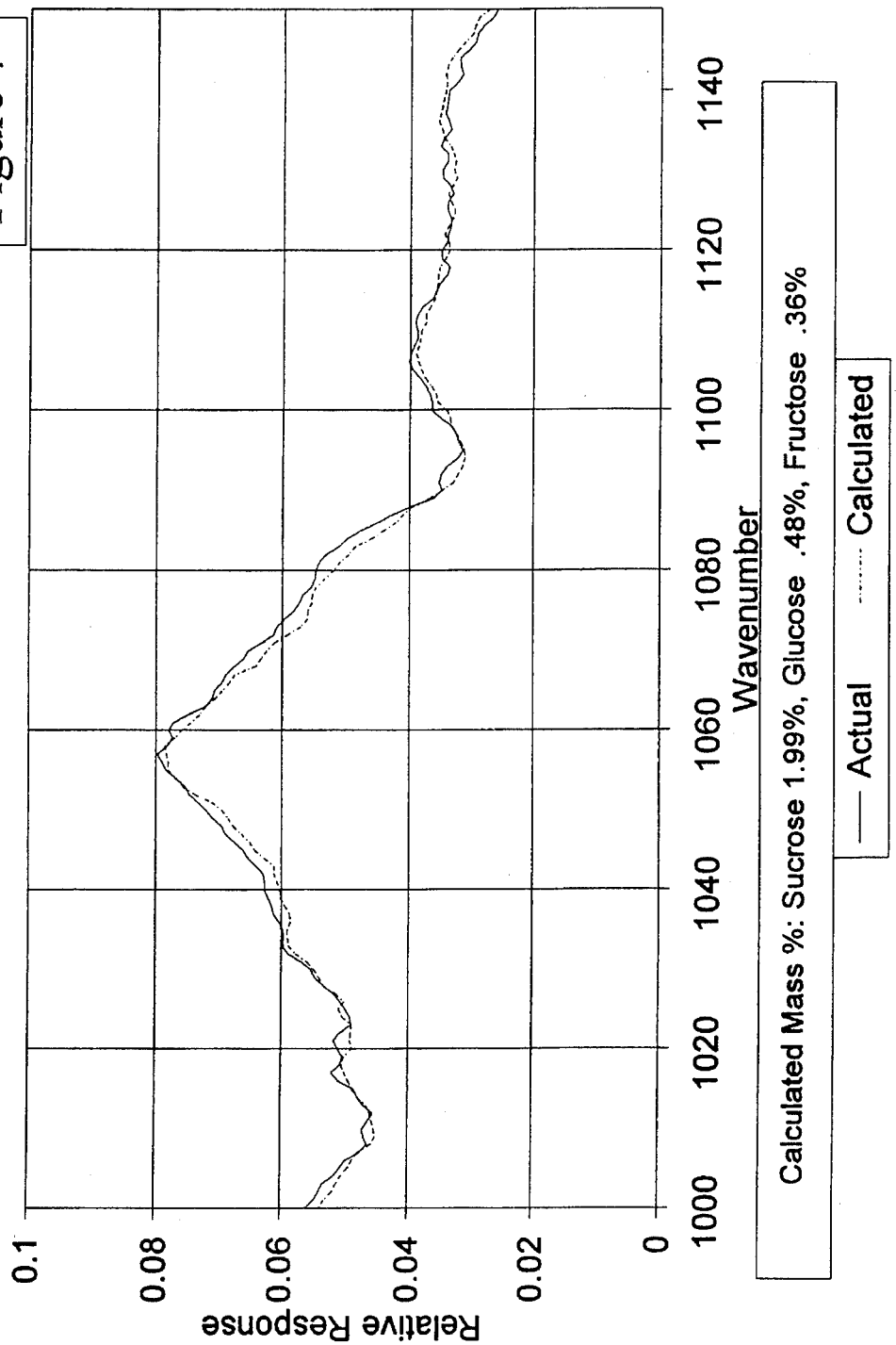

BIOCHEMICAL PROCESS FOR GROWING LIVING CELLS BY MEASURING THE AMOUNT OF NUTRIENT ADDED TO THE REACTION MEDIUM

RELATED PATENT APPLICATIONS

This application is a continuation-in-part patent application of U.S. patent application Ser. No. 07/423,800, entitled "Apparatus and Process For Conducting Biochemical Reactions and Products Made Therefrom," filed Oct. 18, 1989, now U.S. Pat. No. 5,346,826, and U.S. patent application Ser. No. 07/628,321, entitled "Method For Monitoring and Controlling A Chemical Process," filed Dec. 17, 1990, now U.S. Pat. No. 5,262,961. These prior filed patent applications are incorporated herein by reference and made a part of this patent application.

BACKGROUND OF THE INVENTION

1. Field of the Invention

This invention relates to a process and bioreactor apparatus for conducting biochemical reactions under conditions that may be varied to optimize the production of selected products, and a method for monitoring and controlling the biochemical reactions essentially instantaneously based on real time measurements of the concentration of reactants or products produced by the biochemical reactions, or both. Because conditions are readily controlled, and are easily varied, known products and products hitherto unknown are produced in the bioreactor apparatus of this invention.

2. Background Discussion

In U.S. patent application Ser. No. 06/939,818, filed Dec. 9, 1986, entitled "Chemobiotic Tissue Culturing," there is described a process (herein Folsome et al invention) for growing plants cells in a bioreactor. The plants cells are grown under conditions that are independent of weather conditions, and therefore are not subject to the ravages of droughts, floods, frost, or wind. Soil and ground water pollution is eliminated because fertilizers and pesticides are not necessary. Depending upon the plant tissue cultures used as starting material, products produced by the Folsome et al invention may be made to exhibit the original color, taste, odor, and nutritional values of the plant from which the tissue culture is obtained. Products produced by the the Folsome et al invention can be manufactured the year round, maximizing existing packaging facilities. Production facilities employing the process of Folsome et al invention may be located anywhere in the world where water and energy are available.

Franklin T. Andrews, a coinventor of the Folsome et al invention, continued work in this field and disclosed a new biochemical process in U.S. patent application Ser. No. 07/423,800, entitled "Apparatus and Process For Conducting Biochemical Reactions and Products Made Therefrom," now U.S. Pat. No. 5,346,826 (herein Andrews invention). The Andrews invention requires physical parameters to be altered based on the concentration of reactants in the process or products produced by the process. Temperatures, pressures, flow rates, pH and other physical parameters of the process must be changed to optimize the operation of the process. Until the advent of a new method (herein the Farone invention) of monitoring and controlling chemical processes by William A. Farone, the coinventor of the invention of this application, it was difficult to control precisely conditions of the Andrews invention, and in particular carefully regulate the process based on consumption of costly nutrients, namely, sugars such as sucrose, glucose, fructose, sources of nitrogen, potassium and phosphorus, or hormones and vitamins. Franklin T. Andrews and William A. Farone worked jointly to reduce to practice the invention of this application.

The Farone invention is disclosed in U.S. patent application Ser. No. 07/628,321, entitled "Method For Monitoring and Controlling A Chemical Process." Contrary to the Farone invention, conventional monitoring and control techniques are unable to measure the concentration of reactants, the products produced by the process, or both, with sufficient speed to then regulate process parameters based on the measured concentrations. One technique used to measure the concentration of reactants is electromagnetic radiation absorption technology. Over the range of the electromagnetic spectrum, all chemicals absorb or reflect "light" in a unique way that is characteristic of the structure of chemical being examined and its concentration in a mixture of different chemicals. For the present purposes, light includes all regions of the electromagnetic spectrum from x-rays, UV, visible, infrared to microwaves. For example, one may determine the concentration of sucrose in water by spectroscopy, a technology wherein, for example, an aqueous sucrose solution is exposed to infrared light (IR) at different, discrete wavelengths.

The absorption spectra (the level of light absorption over a range of different, discrete wavelengths of light) is characteristic of the aqueous sucrose solution. The spectra is usually described in terms of the wavelength of electromagnetic radiation, for example, from 1 to 100 micrometers ($\mu$m). In spectroscopy, one frequently finds it useful to use a slightly different measure for the spectral position known as the wavenumber. The wavenumber, in $cm^{-1}$, is related to the wavelength in $\mu$m by 1/10,000, that is 1 $\mu$m is 10,000 $cm^{-1}$ and 10 $\mu$m is 1,000 $cm^{-1}$. Conventional Fourier Transform-IR technology is routinely capable of scanning from 1.2 $\mu$m to 100 $\mu$m in as little as ⅛ second with a resolution of $2.5 \times 10^{-5}$ $\mu$m (0.25 $cm^{-1}$). For most purposes, including the purposes of the present invention (on-line chemical control and monitoring), a resolution of 2.0–4.0 cm and scan speed of 1–10 seconds is sufficient. This allows use of less expensive equipment since one pays a premium for speed and resolution.

The governing principle behind current quantitative analytical methods of transmission or absorption measurement instruments, in which realm IR analysis falls, relies on a relationship known as the Bouguer-Beer-Lambert Law. Many sources simply call this Beer's Law. In the simplest form it is written:

$$A = abc \qquad [1]$$

where A is the absorbance, a is the molar absorptivity, b is the pathlength, and c is the concentration. Since the amount of energy absorbed is related to the number of molecules, the concentrations involved are molar quantities such as moles per liter or mole fraction. A mole of a material is a fixed number of molecules, e.g., $6.023 \times 10^{23}$ if the weight (called the molecular weight in this case) is given in grams. The molar absorptivity is the absorbance expected when 1 mole of a particular compound is present at the particular wavelength that the measurement is made.

Equation [1] is normally assumed to hold for every discrete wavelength for which the instrument can distinguish adjacent wavelength intervals. For example, with a 2.0 $cm^{-1}$ resolution, it is possible to distinguish reproducible differences as close as 1.0 $cm^{-1}$. Thus, a spectra from 450 $cm^{-1}$ to 4400 $cm^{-1}$ would have 3,951 points and equation [1] would be assumed to apply to each of these points.

It is frequently useful to combine terms in equation [1] into the form:

$$A = kc \quad [2]$$

where k now represents a "constant" which combines the molar absorptivity and the pathlength. By measuring the absorbance, A, of samples with differing amounts of material at various concentrations, c, one can calculate k. When k does not vary over a range of concentrations, the samples and the material being measured are said to obey Beer's Law.

Once k is known, unknown samples of the material are determined simply by measuring the Absorbance, A, and dividing by k for each discrete wavelength for which the measurements are made and for which Beer's Law has been shown to apply.

One can measure transmission as well as absorbance. The two quantities are related by the expression:

$$A = \ln(1/T) \quad [3]$$

where T is transmission. The transmission is defined as the fractional reduction in intensity of a beam of electromagnetic radiation passing through the medium containing the absorbing material. Formally, it is:

$$T = I/I_0 \quad [4]$$

where I is the measured intensity with the absorbing material in the beam and $I_0$ is the measured intensity without the absorbing material. Sometimes Beer's Law is written:

$$I = I_0 e^{-abc} \quad [5]$$

which is the algebraic combination of equations [1], [3] and [4]. It is much more convenient to analyze results using equations [1] avoiding the use of exponentials.

When one has a mixture of materials, equations [1] or [2] is usually held to be applicable to each of the materials separately. That is, for a mixture of 3 materials at each wavelength or wavenumber:

$$A = k_1 c_1 + k_2 c_2 + k_3 c_3 \quad [6]$$

where the subscripts refer to the three components. Since equation [6] holds at each wavelength (or wavenumber), there are as many equations as wavelengths so the values at the selected wavelength (m) can be written as $Am = k_{m1}c_1 + k_{m2}c_2 + k_{m3}c_3$. This could be, for example, a mixture of three gases moving through a gas cell attached to an FT-IR instrument or two solutes (such as sucrose and ethanol) dissolved in a solvent (such as water). In current practice, again assuming that Beer's Law is valid, the $k_1$ would have been determined from previous experiments and thus the $c_1$ can be calculated if three sets of measurements are taken at three or more wavelengths. In current practice, the measurements over many wavelengths are used to find the "best fit" for $c_1$ using least squares or partial least squares regression analysis. There is no way of determining which series or ranges of wavenumbers is the best to use. This is done exclusively by trial and error based on the analyst's experience.

For a discussion of the state-of-the-art, the book "Fourier Transform Infrared Spectrometry" by Peter R. Griffiths and James A. de Haseth, John Wiley & Sons, 1986 is recommended. Chapter 10 in this book discusses quantitative analysis. Of particular importance is section IV on multicomponent analysis beginning on page 355. On page 356, the authors note that Beer's Law is a requirement for the analysis techniques they present.

There is also a four volume series edited by John R. Ferraro and Louis J. Basile. The series is entitled "Fourier Transform Infrared Spectroscopy" and is published by Academic Press, Inc. Volume 1 was published in 1978, Volume 2 in 1979, Volume 3 in 1982, and Volume 4 in 1985. The latest volume contains a contribution by P. C. Gillette, J. B. Lando and J. L. Koenig on "A Survey of Infrared Spectral Processing Techniques." They again state the requirements for Beer's Law as well as mention that least squares analysis is a preferred technique. Based on experimentation in connection with conducting chemical analysis which the present invention addresses successfully, the least squares and related techniques are highly overrated and are rarely the best techniques for looking at variable data or determining the "best fit" in analysis of spectral data. Further, Beer's Law rarely holds in practical systems, particularly in solvent systems or complex mixed gases or polymeric solids.

SUMMARY OF THE INVENTION

The present invention comprises a combination in a unique way of the Andrews invention and the Farone invention. The process of this invention provides an optimized way of manufacturing foods, pharmaceuticals, and specialty chemicals from such bioreacting, living procaryotic or eukaryotic cellular materials such as yeast, molds, bacteria, and plant cells. For example, plant cells derived from tissue cultures are continuously produced, with two separate streams being created: a cell mass product stream and a metabolite byproduct stream, both of which may be recycled to improve yields. Virtually any living cellular material which grows in an aqueous medium provides the starting cells used in the process of this invention. In accordance with this invention, the cells are highly dispersed throughout the aqueous medium in either a uniform distribution of individual cells or as cellular aggregates. These cells reproduce continually and rapidly, and a portion of the cells are continuously removed from the cell mass product stream in order to maintain the cells in a logarithmic growth state. That is, so that the process yields twice the original number of cells present at start up within 12 hours. Because of this rapid growth, very expensive plant derived products may now be made by the process of this invention at a cost substantially lower than conventional practice. The cell mass produced by the process of this invention may have the same general characteristics as the plant from which the cells are derived or cellular material that has substantially different characteristics may be produced. Selection of conditions determines whether the process maximizes the yield of cell mass or metabolite byproduct.

With this invention, process conditions are controlled to optimized conditions to produce the maximum yield of the selected product, either cell mass or metabolite byproduct. A bioreactor of unique design enables the concentration of reacting ingredients to be easily altered on stream while the bioreactions are occurring. It includes monitoring equipment that detects the concentration of the reacting materials and products that need be controlled. The main parameter of the process which is varied is the concentration of nutrients. A related parameter is the concentration of inhibiting metabolites which can be varied by removal of a portion of the aqueous media containing such inhibiting metabolites. By increasing or decreasing nutrient concentration, controlling the concentration of inhibiting metabolites and various hormones and growth promoters, optimum growth conditions are attained to produce the highest yield of the selected product with the most economical use of nutrients, a major cost of any biochemical process. The nutrients comprise a source of carbon (C), hydrogen (H), usually a sugar, oxygen (O), nitrogen (N), potassium (K), and phosphorous (P). There is more effective use of nutrients in the process of this invention because of recycling of both the cell mass product stream and the metabolite byproduct stream.

The cells are grown in a reaction zone employing a separation membrane. For example, either a tubular dialysis membrane immersed in an aqueous medium or a container having a membrane bottom which floats on the aqueous medium may be used. A suitable container with a membrane bottom may be obtained from Sigma Chemical Company as agents for Hoechst Celanese, Inc. The metabolic byproducts pass through the wall of the membrane into an aqueous medium. The nutrients are supplied to the cells by feeding an aqueous nutrient solution, referred to as the primary nutrient solution, to the cells. The membrane has a pore structure that only allows chemicals with a predetermined molecular weight to pass through the membrane wall. This is referred to as the molecular weight exclusion range. The molecular weight exclusion range is selected based on the desired product to be produced. If a certain metabolite byproduct is to be produced having a relatively low molecular weight, a membrane is selected having an exclusion range that only allows such low molecular weight product to pass through the membrane wall. If the production of cell mass is the objective, the exclusion range is selected that allows very high molecular weight material to pass through the membrane wall, yet prevents the large diameter cellular material from passing through the wall. In some cases the metabolic products from the cells are the desired products while in other cases (whether the metabolic products are desirable or not) the metabolic products inhibit the further rapid growth of cells and the cells benefit from their removal from the vicinity of the cells. In cases where the cells or their contents are the desired final products, the removal of growth repressing metabolites assists the rapid growth of the cells.

An important feature of this invention is that the rate at which nutrient is added to the reaction zone and metabolites are removed from the metabolite zone is carefully controlled. Real time, on-line control is accomplished by using the Farone invention to optimize the process, which broadly, comprises of the steps of:

a) placing live cells in a reaction zone including a membrane in contact with an aqueous medium with the membrane having been selected to pass extracellular metabolic by-products, b) maintaining conditions within the reaction zone to promote rapid growth of the live cells, c) feeding an aqueous nutrient solution to the live cells inside the reaction zone, with the cells digesting a portion of the nutrient solution and a portion of the nutrient solution containing the extracellular metabolic by-products passing through the membrane, d) withdrawing the cells from the reaction zone at a controlled rate, e) withdrawing the extracellular metabolic by-products from the metabolite zone at a controlled rate and f) measuring the concentration of ingredients in the nutrient solution in the reaction zone and measuring the concentration of ingredients in the metabolite zone and regulating the rate at which the nutrient solution is feed to the reaction zone and metabolites are removed from the metabolite zone (the aqueous medium) as a function of the relative concentrations in both zones.

The measuring and regulating may be accomplished directly, i.e., by measuring the concentrations in each zone, or indirectly. The indirect approach may be used when processes have been well characterized as described below. Then concentration of ingredients in both the reaction zone and the metabolite zone are made known by measuring the concentration in only one of the two zones and using a mathematical model to calculate the concentration of the ingredients in the remaining zone. This feature reduces the number of measurements needed and increases the rate at which changes can be made in the controlling parameters.

A spectrometric, i.e. an electrometric reflection or absorbance, instrument is used to determine the concentrations of nutrient in the reaction zone and the aqueous medium. As called for by the Farone invention:

(I) first there is created data files by (a) preparing a number of calibration samples at different concentrations spanning the concentration range of interest for each individual ingredient being monitored, (b) measuring the electromagnetic absorption of the calibration samples at a selected number of different wavelengths over a predetermined range of wavelengths of the electromagnetic spectrum and storing the measurements in a data file in the memory of the computer, (c) repeating steps (a) and (b) a sufficient number of times to obtain statistically significant data composed of these absorbance measurements for the known concentrations of each of the ingredients and storing said data in a data file in the memory of the computer, (d) using the following equation $$k = \frac{A - k_{solvent}(1.0 - c)}{c}$$

where

A is the absorbance measurement of each individual calibration sample, and c is the concentration in molar units of the ingredient in the calibration sample, $k_{solvent}$ (for liquids and solids) is the absorbance value of the component designated as a solvent in which the other components are distributed measured in its pure form, calculating for each calibration sample an average k value at each of said selected number of different wavelengths over said predetermined range of wavelengths, and a standard deviation value thereof, and storing said calculated k values and standard deviation values thereof in a data file in the memory of the computer, (e) preparing a plurality of calibration sample mixtures of the ingredients at known concentrations and measuring the electromagnetic absorption of the calibration sample mixtures at each wavelength within said range of wavelengths of the electromagnetic spectrum, (f) determining which wavelength within said range of wavelengths of the electromagnetic spectrum shall provide a solution to the following equations to an acceptable level of precision by solving said following equations to determine the respective concentrations of the ingredients in the calibration sample mixtures using (i) an arbitrarily selected number of wavelengths within said range of wavelengths, (ii) the lowest standard deviation among the average k values as determined in step (d), and (iii) the singular value decomposition mathematical technique to determine which of the arbitrarily selected number of wavelengths provide the lowest chi-squared statistic between calculated and known values of the concentration of ingredients in the calibration sample mixtures $$A_1 = k_{11}c_1 + k_{12}c_2 + k_{13}c_3 \ldots k_{1n}c_n$$

$$A_2 = k_{21}c_1 + k_{22}c_2 + k_{23}c_3 \ldots k_{2n}c_n$$

$$A_3 = k_{31}c_1 + k_{32}c_2 + k_{33}c_3 \ldots k_{3n}c_n$$

.
.
.

$$A_m = k_{m1}c_1 + k_{m2}c_2 + k_{m3}c_3 + \ldots + k_{mn}c_n$$

where $A_1, A_2, A_3 \ldots A_n$ are the values of the absorbance measurements at said arbitrarily selected wavelengths, $k_{m1}, k_{m2}, k_{m3} \ldots k_n$ are the average k values from step (d) which most closely correspond to the k values for the concentration of ingredients in the calibration sample mixtures for each wavenumber or wavelength, and $c_1, c_2, c_3 \ldots c_n$ are the concentrations (either known or unknown) expressed in molar units, of the ingredients in the sample mixtures, (II) second conducting on-line monitoring by (i) continually sampling the chemical process to collect individual samples in which the concentration of ingredients is unknown and measuring the electromagnetic absorption of said individual samples at the arbitrarily selected number of wavelengths which provide the lowest chi-squared statistic between calculated and known values of the concentration of ingredients in the calibration sample mixtures as determined in step (f), (j) solving the following equations in accordance with singular value decomposition mathematical technique to determine the respective unknown concentrations of the ingredients in the samples taken in step (i) using the average k values at the wave lengths determined in step (f)

$$A_1 = k_{11}c_1 + k_{12}c_2 + k_{13}c_3 \ldots k_{1n}c_n$$

$$A_2 = k_{21}c_1 + k_{22}c_2 + k_{23}c_3 \ldots k_{2n}c_n$$

$$A_3 = k_{31}c_1 + k_{32}c_2 + k_{33}c_3 \ldots k_{3n}c_n$$

.
.
.

$$A_m = k_{m1}c_1 + k_{m2}c_2 + k_{m3}c_3 + \ldots + k_{mn}c_n$$

where $A_1, A_2, A_3 \ldots A_n$ are the values of the absorbance measurements taken in step (i), $k_{m1}, k_{m2}, k_{m3} \ldots k_n$ are the k values from step (d) at each wavenumber or wavelength n, and $c_1, c_2, c_3 \ldots c_n$ are the concentrations expressed in molar units of the unknown ingredients in the samples, (k) repeating step (j) using k values which corresponds most closely to the k value for the concentration of the unknown ingredient as determined in step (j), (l) using the concentration of ingredients as determined in step (k), calculating absorption of the unknown sample and comparing said calculated absorption with the actual measured absorption, and (m) repeating steps (k) and (l) until the statistically best values of k used in determining the concentrations of unknown ingredients so that the results obtained in repeated calculations of the unknown concentrations of ingredients in the samples have a percentage deviation of less than about 1 percent.

According to the present invention, real time measurements are conducted on-line to control the process by monitoring the concentrations of nutrient in the reaction zone and the extracellular metabolite zone, and altering the rate of feeding nutrient to the reaction zone or the rate of removal of metabolites from the metabolite zone as determined by absorption data taken with a spectrometric instrument and using a general purpose computer to adjust said rate of feeding nutrient.

The process is monitored and controlled by (a) measuring the concentration of nutrient or material in extracellular metabolite zone in samples from the process using a spectrometric instrument to obtain spectral data characteristic of measured components, e.g., nutrient, (b) analyzing the spectral data using a chi-squared mathematical technique to determine the unknown concentration of measured components in said samples, and (c) altering the rates in the zones based on the determination of concentration of measured components in step (b) as required to optimize the process.

GENERAL

The versatility of this invention is best illustrated by considering two cases. The first case is where the objective is to produce large quantities of cell mass. The second case is to produce a specific metabolite byproduct.

In the first case, the concentration of nutrients and the correct mix of nutrients in the primary nutrient solution is determined by changing the concentration and mix of nutrients until the highest yield of cell mass is achieved. The composition of the aqueous medium in which the tubular membrane is immersed is also established to favor cell mass production. When these conditions are determined, they are monitored along with the rate of cell mass production. If cell mass production decreases, the conditions are again changed to maximize yield. As metabolite byproducts are produced they pass through the wall of the membrane and are continuously removed from the bioreactor. The cell mass product is continually removed from the bioreactor at a controlled rate to maintain the cells in their logarithmic growth state. Thus, the selection of the products being removed and the rate of removal are controlled to create conditions which favor cell mass production and most economical use of nutrients.

In the second case, the concentration of nutrients and the correct mix of nutrients in the primary nutrient solution is determined by changing the concentration and mix of nutrients until the highest yield of metabolite byproduct is achieved. Also, the concentration of ingredients in the aqueous medium in which the tubular membrane is immersed are controlled to favor the production of metabolite byproducts. Again conditions are monitored and changed as needed to maintain the highest yield of metabolite byproducts with the most economical utilization of the nutrients.

The cells upon reaching a mature condition divide to produce two or more immature cells, which may be cell aggregates or individual cells. If conditions prevail were the concentration of aged, mature cells are the dominate population, clumping tends to occur, which may or may not represses the cell division. In order to keep the cells in the state favoring cell growth or metabolite production, individual cells or small aggregates (as opposed to clumps, which are relatively large masses of cells that block pumps or otherwise interfere with the operation of the process) are dispersed throughout the aqueous medium and the cell or small aggregate concentration is controlled so that the cells remain in their logarithmic growth state. This is, so that the concentration and age or other characteristics of cells does not tend to suppress logarithmic growth. As used herein, cells refer to both individual cells or small diameter aggregates of a number of cells.

In some cases the cells may only produce desirable metabolic products internal to the cells if they are allowed to aggregate into cellular clumps usually referred to as callus especially when such cell clumps are not differentiated into various specific kinds of cells. These larger aggregates are best grown further by removing them from a system requiring them to pass through pumps (or to be moved about with a high rate of liquid flow) and placing them under sterile conditions on membrane supports in contact with aqueous media where they can continue to grow until harvested.

This invention includes a process, bioreactor apparatus, and unique products produced in the bioreactor apparatus in which the process is conducted. There are a number of features of this invention, no single one one of which is solely responsible for all its advantages. Without limiting the scope of this invention, as it is expressed in the claims, its more prominent features will now be briefly discussed. After considering this discussion, and particularly after reading the section of this application entitled "DETAILED DISCUSSION OF THE PREFERRED EMBODIMENTS," one will understand how the features of this invention provide its advantages, which include, but are not limited to:

1. Ability to vary conditions of the process to control yield and quality of products.

2. Low cost of otherwise expensive plant derived products.

3. Ability to make plant derived products without need for conventional farming practices.

4. Optimal conversion and use of nutrients.

5. Uses a wide range of nutrient sources.

6. Ability to make products with a minimum amount of soil, ground water, and air pollution.

7. Ability to regulate the metabolic rates and products of cells.

FEATURES

The first feature of this invention is that the cells produced by the process of this invention, while essentially the same as the source from which they are derived such as plants, frequently contain a greater proportion of the original plant's main characterizing ingredient. For example, red kidney beans, which normally contain around 42 percent protein, when grown by this process may contain as much as 80 percent protein. Because of this feature, many novel plant derived products may be produced by this process which have hitherto been unknown.

The second feature of this invention is that the cells are grown in a bioreactor which uses a flexible, semi-permeable, tubular membrane. The primary nutrient solution is continuously fed to the cells growing in the tubular membrane. Conditions are controlled to promote rapid cell growth, with the cells in the logarithmic growth state so that the number of cells in the tubular membrane doubles within 8 to 12 hours. Extracellular metabolic byproducts are dialyzed through the membrane wall into the aqueous medium (extracellular metabolite zone) surrounding the tubular membrane. The cells can be conditioned to maximize the concentration of extracellular byproducts when extracellular byproducts are the desired product. The aqueous medium may be either water or a dilute nutrient solution utilizing some of the same ingredients as the primary nutrient solution, but containing from 10 to 50 times more water than the concentrated nutrient solution. When the live cellular material is derived from plants and the cells require photosynthesis to produce desirable products, the membrane is illuminated with light of sufficient intensity to allow photosynthesis to occur.

The third feature is that the tubular membrane is made of standard membrane material such as, for example, cellulose acetate, polyacrlonitrile, or polysulfone. This eliminates the need for the development of special membrane materials. The physical dimensions of the tubular membrane are, however, important to attain the desired yields. Typically,the tubular membrane has diameters of from 0.25 to 3.0 inches, and lengths of from 1 to 8 feet. The exclusion range of the dialysis membrane depends upon the kind of cell mass product grown, the extent of biofouling (e.g. build up of extracellular polysaccharides on the membrane, and whether the desired product is the cell mass or the metabolite byproducts. Normally, an exclusion range of 500 to 1,000,000 Daltons is sufficient to retain most plant cells inside the tubular membrane while allowing most metabolite byproducts to diffuse into the aqueous medium. However, if a metabolite byproduct of a specific molecular weight is the desired product, the exclusion range of the tubular membrane is selected to accommodate the molecular weight of the desired metabolite byproduct. Although the preferred configuration of the membrane is tubular, other reactor designs are possible. Also, the tubular design allows for a bioreactor to comprise a tube within a tube to create inner and outer reaction zones. The cells may be grown in either the inner or outer reaction zone, although the inner zone is preferred. Different types of cells may be grown simultaneously in each zone. The concentration of nutrients is maintained at the correct levels for each specific type of cell mass product through introduction of nutrients dissolved in water into either the inner or outer reaction zones. The selection of the exclusion range and concentration of ingredients in the primary solution and aqueous medium is determined so that that the optimum growth rate for the selected product is achieved.

The forth feature is that the process grows cells continuously. Cells are constantly withdrawn from the tubular membrane at the same rate that new cells are grown. To do this the cell population inside the tubular membrane must be kept at an essentially constant level. Most cells have a critical population level below which they will not grow in the tubular membrane. It has been discovered that for most cellular material the minimum concentration of cells at start-up is at least $10^2$ cells per milliliter, and preferably ranges from $10^2$ to $10^7$ cells per milliliter. The cells may be either very large or very small, and therefore, cell count is not necessarily the only way to characterize conditions of the process. An alternate way is by the mass fraction of cellular material compared to the total weight of material in the membrane. Using this approach the start up concentration of cells is from 0.0005 to 0.01 mass fraction.

The fifth feature is selective cell removal, which is accomplished by installing a cell separating device on the effluent cell mass product stream from the tubular membrane which separates the cells by size. Cells can be removed quite directly by replacing the cell and liquid volume with an equal volume of nutrient media. Cell removal is controlled so that the cells are withdrawn from the tubular membrane at a rate sufficient to prevent metabolite and competitive repression of the growth of the cells. In general, this entails removal of either aged mature cells or clumps.

The sixth feature is to recycle cells exiting from the tubular membrane back to the influent end of the tubular membrane so that they may grow larger, divide and multiply, thereby increasing the yield.

The seventh feature is to recycle the metabolite byproduct stream to increase the concentration of metabolites in the metabolite byproduct stream. The metabolite byproducts are separated from the metabolite byproduct stream and this stream is recycled or the metabolite stream can be partially replaced by pure sterile water or a sterile aqueous media designed to control the diffusion of various chemical species across the membrane.

The eighth feature is to tailor the ingredients and concentration of ingredients in the primary nutrient solution to provide the greatest possible yield of cell mass or metabolite byproduct, depending on the desired product. The portion of the plant which yields the desired product is freshly harvested, and a small section of this plant is excised and cultured in accordance with conventional practice to produce the cells used at start-up of the process. These cells are grown using several different nutrient solutions to determine which nutrient solution composition produces the fastest cell growth. Of the several different solutions screened, the nutrient solution composition producing the fastest cell growth is used as the primary nutrient solution which is fed to the cells in the tubular membrane. Although this screening may be done prior to introducing the cells into the bioreactor, one of the advantages of the bioreactor is that the screening preferably is accomplished on stream in the bioreactor by simply monitoring the yield of the desired product as the concentration and mix of nutrients is altered in either the primary nutrient solution or aqueous medium, or both.

The ninth feature is to chemically tailor the dilute nutrient solution to increase the yield of the desired product in the metabolite stream. Typically, the primary nutrient solution is simply diluted with water, usually using from 10 to 50 times more water than is present in the primary nutrient solution. In some instances, the dilute nutrient solution may contain no carbon and hydrogen source (sugar), and only contain a source of nitrogen, potassium and phosphorous.

The tenth feature of this invention is that the dilute nutrient solution provides a nutrient back-up source for the cells growing inside the tubular membrane. As the cells grow in the tubular membrane nutrients are consumed. Consequently, there may be insufficient nutrients available to downstream cells. The nutrients in the dilute nutrient solution move across the wall of the membrane into the interior of the membrane to supply the downstream cells.

The eleventh feature is to maintain a higher pressure either inside or outside the dialysis tubes to obtain the most favorable osmotic pressure gradient to increase the yield of the desired product. For example, if excess metabolite byproduct is in the cell mass product stream, the pressure inside the membrane is increased to force the metabolite byproduct across the membrane wall and into the aqueous medium. If excess nutrient is in the aqueous medium, the pressure on the aqueous stream is increased to force the nutrients into the membrane. The pressure across the membrane is varied by changing the applied physical pressure on either side of the membrane or by altering the osmotic pressure by changing the concentration of ingredients in either the primary or dilute nutrient solutions. The pressure in controlled to achieved the highest yield of the desired product.

The twelveth feature of this invention is to control the physical and chemical conditions of the process to provide optimum yields of product. Each particular product being made by the process of this invention will require different conditions to optimize the yield. Some of the more important variables to be controlled are:

a) The ingredients and concentration of ingredients in the primary nutrient solution.

b) The ingredients and concentration of ingredients in the dilute nutrient solution (extracellular metabolite zone).

c) The pH of the primary nutrient solution and aqueous medium. The pH of the concentrated nutrient solution under aerobic conditions is maintained in a range from 3.0 to 8.0, and under anaerobic conditions is maintained in a range of from 6.0 to 11.0 for plant cells decreasing to as low as 2.5 for certain microbial cells.

The pH of the dilute nutrient solution may be the same or different as the primary nutrient solution.

d) The temperature. The temperature of the nutrient solutions is maintained in a range from 50 to 75 degrees Fahrenheit for plant cells and up to 120 degrees Fahrenheit for certain microbial cells.

e) Velocity of the concentrated nutrient solution. Concentrated nutrient solution velocity through the tubular membrane is within the range of 0.005 to 3.0 feet per minute.

f) The velocity of the aqueous medium. The aqueous medium (metabolite zone) velocity across the exterior surface of the tubular membrane is in the range of 0.005 to 5.0 feet per minute.

g) Cell concentration in the effluent. The effluent from the tubular membrane has a cell concentration within the range of $10^2$ to $10^{10}$ cells per milliliter or a mass fraction of from 0.005 to 0.15.

h) The aerobic or anaerobic environment. Gas containing oxygen is percolated through the tubular membrane if the cell metabolism is aerobic. Gas containing nitrogen, carbon dioxide, or a mixture of nitrogen and carbon dioxide is percolated through the tubular membrane if the cell metabolism is anaerobic. Gas under pressure is forced through the tubular membrane. The pressure may be varied to flex the membrane, thereby agitating the membrane wall to remove cell material that may prevent dialysis across the membrane wall.

The thirteenth feature of this invention is that different cell types may be simultaneously introduced into the tubular membrane to produce a unique cell product having distinctive taste, color, odor and nutritional characteristics.

The preferred embodiments of this invention illustrating all its features will now be discussed in detail. These embodiments employ garlic as the plant from which both cell mass product and metabolite byproduct are derived, but other living cells and metabolite byproducts have been produced by the process of this invention, including:

red kidney bean carrots bamboo clover lima beans wheat corn yeast, for example, saccharomyces cerevisiae

MONITORING AND CONTROL

It is the objective of this invention to measure on line in real time the concentration of reactants and products, in particular nutrients in the reaction zone and primarily metabolites in the aqueous medium (extracellular metabolite zone), and to essentially instantaneously control, if needed, the physical parameters of the processes involved based on the concentration measurements to optimize the yield of the desired products. The term instantaneous can mean from a few seconds to a few minutes, depending on the speed required for the system under control. For a biochemical reaction, which takes days to complete, a few minutes is sufficiently instantaneous. For a rapid gas phase reaction, a few seconds would be needed.

1. The mixture of chemicals being analyzed do not need to obey Beer's Law.

2. The "best" wavelength range for determining concentration is automatically located.

3. Answers are obtained based on statistical criteria, i.e., standard deviations and Chi-square.

4. The process is fast. Typically, it takes a few seconds on a 12 Mhz 80826 microcomputer with math coprocessor and hard disk to perform the final analysis. Each of the steps can also be automated and are also fast.

5. The method works for any spectrometer and with any combination of solvents and solutes to the precision set by the limits of the mathematical analysis employed. That is, if a statistically significant answer is possible for a particular combination of instrument, cell, and mixture of chemicals to a desired level of precision, the method of this invention has the best mathematical chance of finding useful ranges of the spectra and solutions to the analysis problem.

There are a number of different types of IR instruments available, including grating, prism, and Fourier transform (FT) instruments. Although grating or prism IR instruments may be used for the purposes of the present invention, the FT-IR instrument is preferred because it can scan a wide range of IR frequencies in a very short time. The methods to be described are also applicable to other portions of the electromagnetic spectrum besides IR, for example, UV, visible and microwaves.

Statistical Deconvolution

In accordance with this invention, a modified Chi-Square fitting mathematical technique is employed in analyzing spectral data. For purposes of this spectral analysis, points are better weighted by the inverse of the standard deviation at a particular wavelength rather then the minimum of the squares of the deviations as in the least squares analysis. The analytical technique used in this invention is related to the Chi-Square fitting mathematical technique and it provides a much more powerful method and is a major improvement in analysis of spectral data.

In the modified Chi-Square technique of this invention, obtaining the spectrum is repeated many times, for example, 32 or 64 replicates. The average and standard deviation are then calculated at each wavenumber (or wavelength). The calculation to find the best values of the concentrations from an equation like equation [6] are fit by weighting the points in the spectrum with the lowest standard deviation more than points with the higher deviations. This results in improved accuracy and precision.

The modified Chi-Square technique employed in the present invention is new in the context of spectroscopy. The known Chi-Square technique has been particularly modified to fit into the method of this invention for analyzing spectral data using a conventional general purpose computer and FT-IR instrument. An excellent discussion of the Chi-Square technique, in general terms, appears in "Numerical Recipes, The Art of Scientific Computing," by William H. Press, Brian P. Flannery, Saul A. Teukosky, and William T. Vetterling, Cambridge University Press, 1986. Chapter 14 in the book does a good job of explaining the short falls of the overused least squares techniques and provides a particularly robust (in the mathematical sense) technique for carrying out a Chi-Square fit known as Singular Value Decomposition (SVD). This technique assures meaningful answers even when the equations being solved are unstable.

One disadvantage of the Chi-Square technique is that the standard deviations of the measured solution are needed at each wavenumber. This would normally mean taking many spectra of the same sample. Since one purpose of our process is for continuous and rapid monitoring, a means was developed to avoid making multiple determinations.

It was found that the errors in the spectra are mostly a function of the instrument, the cell in which the sample resides, and the particular nature of the chemical solution being analyzed. That is, a sample of water, sucrose, ethanol, and glucose in a particular cell in a particular instrument will have similar errors over a wide range of concentrations. Thus, in determining unknown samples of sucrose, glucose, ethanol in water, one can use the standard deviations from previous measurements on known solutions made while calibrating the instrument to determine the k's of equation [6].

One can always improve on the algorithm, either the Chi-Square or the least squares, by selecting specific wavelengths at which the calculations are done. That is, by looking at the separate spectra of the materials to be determined in combination, one can find regions of the spectrum where there is just the right amount of overlap or interference to make the final absorbance be a "comfortable" sum of all the materials. To better understand this, consider a gas phase spectrum comprising a mixture of nitric oxide, carbon monoxide, and carbon dioxide. In the gas phase, it is possible to find regions of the spectrum where characteristic absorbance lines of only one of these items shows up. Since only one item shows up, one can use equation [1] separately for each component by only analyzing for that gas over that restricted wavelength region. It is this technique that made gas phase work easier and this logic that made artisans in this field seek simpler analytical methods for liquid or solid phase problems. The present invention provides such a simpler method using regions of the spectrum where the absorbance due to a complicated mixture is strongly influenced (overlapped) by many of all of the components of the mixture.

Surprisingly, in the case of accurate and precise multi-component analysis using equation [6], or a similar equation for however many components one wishes, the best results appear in wavelength regions where the terms $k_1$ and $c_1$ have approximately equal values in the expression $(k_1 c_1)$. One can determine the $k_1$ separately for each component beforehand. The region of the spectra that has k values for each component multiplied by the expected concentration, approximately equal to each other, will be the best range in which to work. For example, in a mixture of sucrose, glucose, and fructose in water, this region is 920 to 1250 $cm^{-1}$. This type of conclusion, for each set of materials studied, is reached naturally by use of the methods of this invention, but cannot be predicted.

Even more surprising was the discovery that once one became used to exploring the values of k versus wavenumber (or wavelength) the files of k's could be kept as a function of concentration and the best k for the values nearest the concentration range being sought could be automatically used with a very simple computer algorithm. This means that adherence to Beer's Law is no longer a requirement for the analysis. One simply must know the value of the k's as a function of concentration for each material separately or as modified by interactions with each other as shall be explained below. These k values are stored in data files in the memory of the computer as ranges of interest and then equation [6] is solved using the k values that best meet the concentration range of the mixture. After one calculation, when concentrations have been found, the k values closest to that concentration, or new k values found by non-linear cubic spline interpolation between k values above and below, are used to recalculate the concentrations. This procedure is repeated until the method converges to the desired degree of precision.

DESCRIPTION OF THE DRAWING

The preferred embodiment of this invention, illustrating all its features, will now be discussed in detail. This embodiment depicts the novel and non-obvious method of this invention depicted in the accompanying drawing, which is for illustrative purposes only. This drawing includes the following figures (FIG.), with like numerals indicating like parts:

FIG. 1' is a schematic diagram of a chemical process employing the monitoring and control method of this invention.

FIG. 5' is the absorption spectra of an aqueous solution containing known concentrations of sucrose (2.5%), glucose (0.59%), and fructose (0.30%), a calibration mixture sample, taken over a range of wavenumbers between 900 and 1150 using k values from data files 3% sucrose/0.5% glucose/ 0.25% fructose over the scan range 1114–1032. The solid line shows actual data points, the dotted line shows calculated data points.

FIG. 6' is the absorption spectra of an aqueous solution containing known concentrations of sucrose (2.5%), glucose (0.59%), and fructose (0.30%), a calibration mixture sample, taken over a range of wavenumbers between 900 and 1150 using k values from data files 3% sucrose/0.5% glucose/ 0.25% fructose over the scan range 1114–902. The solid line shows actual absorbances points, the dotted line shows calculated absorbance points.

FIG. 7' is the absorption spectra of an aqueous solution containing unknown concentrations of sucrose, glucose, and fructose taken over a range of wavenumbers between 1000 and 1160. According to the method of this invention, the concentrations were determined to be sucrose 1.99%, glucose 0.48%, and fructose 0.36%. The solid line shows actual absorbance points from the unknown measured spectrum, the dotted line shows calculated absorbance points using the values of concentration determined by the method of the invention.

DETAILED DESCRIPTION OF PREFERRED EMBODIMENTS

Biochemical Process

First, select a portion of a plant which contains the desired product, either cell mass product or metabolite byproduct, and then culture this selected portion in accordance with conventional culturing techniques to provide plant cells used at start-up. A section from a garlic bulb, cultured in accordance with the following culturing protocol, provides garlic cells which are grown by the process of this invention in the apparatus depicted in the FIGS. 1 and 2.

GARLIC PROTOCOL

Garlic (allium sativum L.) is an excellent example of the type of cell product that may be made by the process of this invention, because it is easy to culture, the cell mass produced retains garlic's characteristic color, odor and taste, and the strengths of these characteristics are enhanced by the process of this invention.

Figure 1:
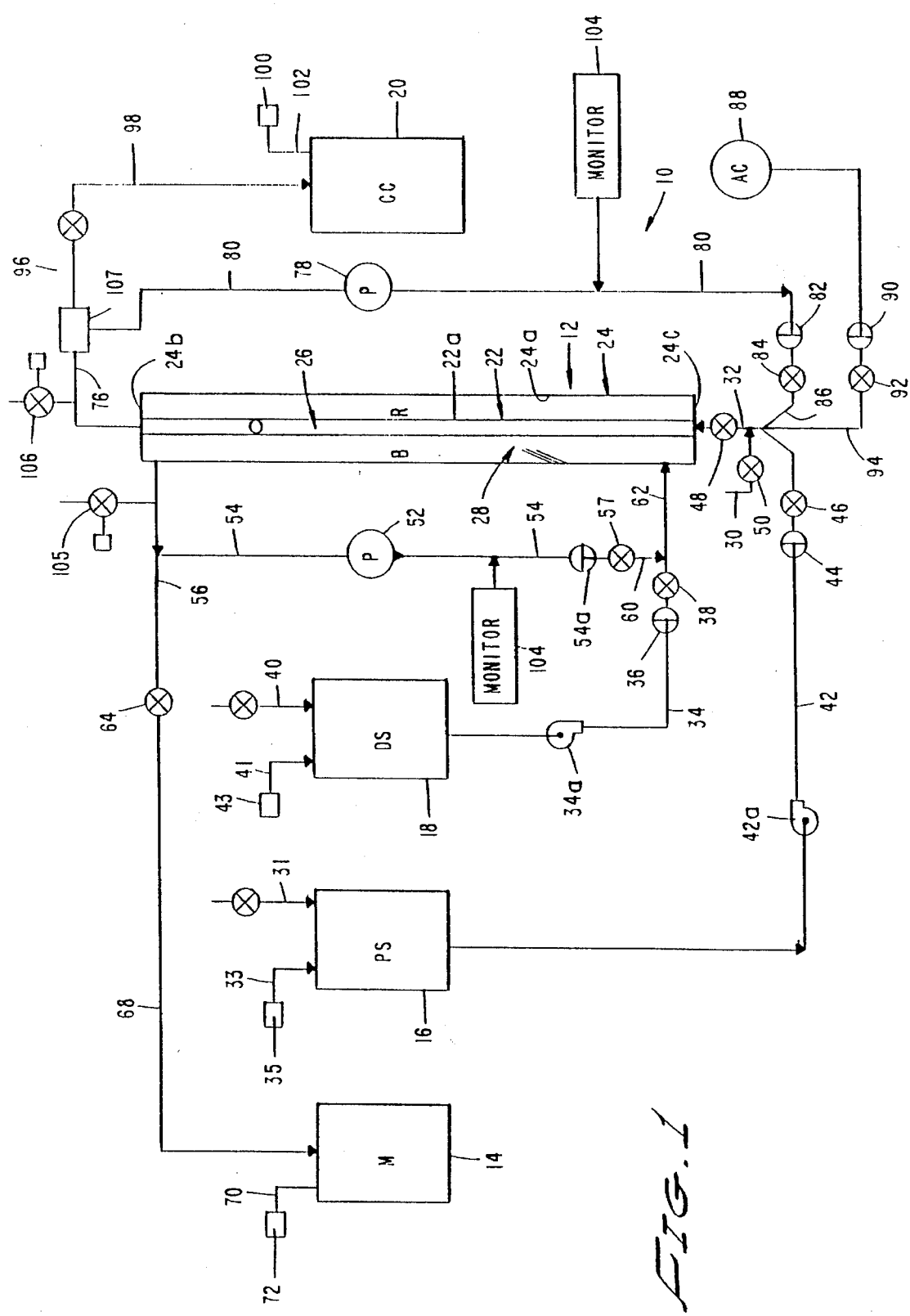
FIG. 1 is a schematic diagram showing a small scale demonstration unit for carrying out the process of this invention.
Figure 3:
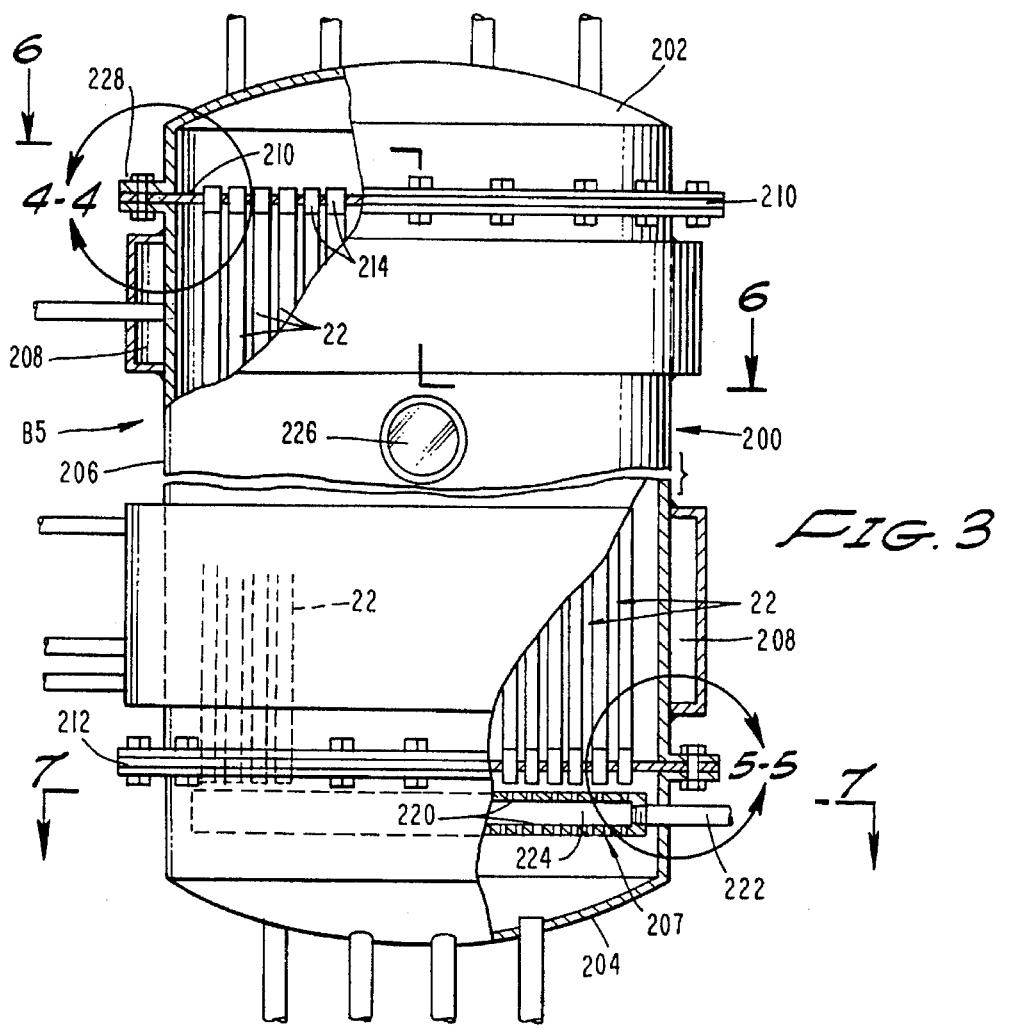
FIG. 3 is a side elevational view, with sections broken away, of the bioreactor used in the production facility shown in FIG. 2.

Preparation of Cell Culture a) The first step is to break open a fresh bulb of garlic and select a clove as the source of an explant.

b) Under a sterile hood with a sterile scalpel and tweezers remove the clove's paper thin covering and soak it in a 90% ethanol solution for 5 minutes and a 5 to 10% Chlorox solution for 5 to 10 minutes. Next, wash the clove thoroughly with sterile distilled water and place it in a sterile petri dish.

c) Hold the clove in the tweezers over a petri dish and with the scalpel, cut deep into the center of the clove and remove the apical meristem tissue.

d) Take a number bits of about 0.2 to 0.5 mm each from the sterile garlic tissue and place into a modified Murashige-Skoog nutrient medium containing 2 ppm of 2,4, dichlorophenoxyacetic acid and solidified with 0.6 to 0.8% of Difco Bacto Agar on the bottom of 250 ml Erlenmeyer flask. The use of the 2,4, dichlorophenoxyacetic acid need not be used once the cells are growing in the bioreactor shown in FIGS. 1 and 2.

e) Incubate the sections in the dark or low light at 25–28 degrees Centigrade. After 3 or 4 weeks the callus should be about twice the size of the original explant. Solid medium cultures are used to preserve desirable cell lines.

f) To prepare suspension cultures, the kind used in the bioreactor depicted in FIGS. 1 and 3, the sterile garlic bits obtained in steps (b) and (c) are placed in 250 ml Erlenmeyer flasks containing a modified, liquid Murashige-Skoog medium of the same composition as step (d) but without agar.

g) Place multiple flasks on a shaker for 4 to 6 weeks and watch for cell growth. The rate of growth, color, odor, taste and nutritional value of the cells is compared to original tissue, which is the measure of the efficiency of the culturing media. Such characteristics are measured by sampling cells from the different flasks.

Preparation of Nutrient Solutions

The primary nutrient solution is prepared using conventional screening methods. This may be done as illustrated in the following example to determine what primary nutrient solution to use at start-up, and then the composition of the primary nutrient is varied while the process is being conducted in the bioreactor to optimize for highest yield of the desired product, either cell mass or metabolic by product.

In the literature there is set forth the protocol for culturing most well known plants. Each protocol identifies the mix of ingredients and concentration of ingredients of the preferred nutrient solution for the culture explant selected. This is the starting nutrient solution which is modified as required to produce the highest yields of products with all the desirable characteristics of the original plant tissue made by the process of this invention.

The primary nutrient solution comprises water in which are dissolved inorganic nutrients, organic nutrients, and growth promoters. By varying the composition and concentration of these ingredients and screening, the optimum primary nutrient solution is obtained.

The principal inorganic nutrient elements are nitrogen (N), phosphorus (P), potassium (K), calcium (Ca), sulphur (S), and magnesium (Mg), which are used in millimolar quantities, and boron (B), copper (Cu), iron (Fe), maganese (Mn,) molybdenum (Mo), and zinc (Zn), which are used in micromolar quantities. The concentration of these nutrients remain fairly constant for growing for most plant cell and usually are not changed in the initial screening. When the process is on stream, however, they are varied to optimize yields.

The principal organic nutrient element is carbon from sugars, starch, or algae. Coconut milk and casein hydrolsolate may also be used as an extra source of carbon. In some cases, carbon dioxide can be used.

The growth promoters are, for example, hormones, phytohormones and vitamins. The vitamins, hormones and phytohormones are most important for cell division and growth, and vary widely with each type of cell. Thiamine is important for most plants. Nicotinic acid, gibberelin (a phytohormone) and pyridoxine (a B-complex vitamin) are also used for growth improvement. The phytohormones, especially the cytokinins and auxins, are of greatest importance in inducing mitosis and regulating cell growth. The cytokinin most often used is kinetin which occurs naturally in most plants. Other cytokinins used are zeatin, benzyladenine, and isopentyl adenosine. Auxins most often used are 2,4,dichlorophenoxyacetic acid, napthaleneacetic acid, 2,indolephenoxyacetic acid, and indolebutyric acid.

The best nutrient solution for any kind of cells must be determined by using different hormone modifications and ratios of the standard Murashige-Skoog, Gamborg solutions, or with specially prepared media. For example, due to rapid cell growth in the bioreactor, greater than normal concentrations of carbon source can be used.

EXAMPLE

Small bits of garlic cells prepared according to the protocol are transferred to each hole of a 98 hole Falcon test tray containing the different nutrient solutions to be tested. Six replications of each solution were tested to indicate individual solution effectiveness. The test trays were monitored weekly over a six week period to evaluate the particular solution that grew the greatest amount of cells.

The next step was to prepare a sufficient amount of sterile garlic cells in the optimized, sterile nutrient solution. Garlic bits having a diameter of 0.5 millimeter or smaller, were placed in Erlenmeyer flasks containing 100 ml of the optimum nutrient solution. The flasks were placed on shaker table and within 5 weeks the garlic formed a suspension culture which was transferred to the demonstration unit shown in FIG. 1. The optimum sterile primary nutrient solution and aqueous medium are then developed "in site" in the bioreactor to produce the highest yield of the desired product.

The Start-Up Garlic Primary Nutrient Solution

The composition of the start-up garlic nutrient solution developed by the screening procedure described above and tested in the demonstration unit depicted in FIG. 1 is as follows:

| Nutrient Source | Nutrient Provided | Concentration (mg/liter) |
| --- | --- | --- |
| Ammonium Nitrate | Nitrogen | 1650 |
| Potassium Nitrate | Potassium/Nitrate | 1900 |
| Calcium Chloride | Calcium | 330 |
| Potassium Phosphate | Potassium/Phosphorus | 170 |
| Magnesium Sulphate | Magnesium/Sulfur | 181 |
| Potassium Iodide | Iodine | 0.83 |
| Ferric Sulphate (EDTA) | Iron | 36.7 |
| Manganese Sulphate | Manganese/Sulfur | 16.9 |
| Boric Acid | Boron | 6.2 |
| Sodium Molybdenate | Molybendum | 0.25 |
| Cobalt Chloride | Cobalt | 0.025 |
| Copper Sulphate | Copper | 0.025 |
| Sucrose | Carbon | 30,000. |
| HORMONES AND VITAMINS | | |
| i-Inositol | | 100.0 |

-continued

| Nutrient Source | Nutrient Provided | Concentration (mg/liter) |
| --- | --- | --- |
| | Indole-3-acetic acid (IAA) | 1.0 |
| | Thiamine | 0.4 |
| | Glycine | 0.4 |
| | Kinetin | 5.0 |
| | (2-Isopentenyl) adenine(2iP) | 7.5 |
| | Naphaleneacetic Acid (NAA) | 1.0 |
| | Pyridoxine.HCl | 0.1 |
| | Niacin | 0.1 |
| | 2,4 Dichlorophenoxyacetic Acid (2,4-D) | 2.0 |
| | Coconut Milk (% volume/volume) = 5.0 | |

Start-Up Garlic Dilute Nutrient Solution

The dilute solution used in the demonstration unit shown in FIG. 1 to grow garlic cells contained 10 times more water than the concentrated solution described above.

Demonstration Unit

As shown in FIG. 1, the demonstration unit 10 includes a bioreactor 12, a metabolite holding tank 14, a primary nutrient solution holding tank 16, a dilute solution holding tank 18, and a cell collection tank 20. The bioreactor 12 comprises a dialysis tube or an inner tubular dialysis membrane 22 and an outer cylindrical vessel 24 which contains the aqueous medium, in this case the dilute nutrient solution in the tank 18. The arrangement of the tubular membrane 22 within the vessel 24 provides an inner reaction zone 26 within the membrane and an outer reaction zone 28 in the space between the wall 24a of the vessel and the wall 22a of the membrane. The ends 24b and 24c of the vessel are closed and sealed at the junction with the membrane wall 22a. The bioreactor 12 is vertically oriented, but may be tilted at an angle.

The tubular membrane 22 is initially filled with cultured plant tissue through the valve line 30 and valve line 32 to the lower end of the tubular membrane 22. It is important that a sufficient number of plant cells be present inside reaction zone 26. Enough cells must be present so that they will divide and multiply to maintain a minimum cell growth rate. Thus, the minimum concentration of cells inside the inner reaction zone is $10^2$ cells per milliliter. Depending upon the diameter of the cells, the initial charge may range between $10^2$ to $10^7$ cells per milliliter (mass fraction of from 0.0005 to 0.05). Dilute nutrient solution from the holding tank 18 is pumped by pump 34a through the line 34 to the check valve 36 and open valve 38 into the inside of the vessel 24 to fill the outer reaction zone 28 with dilute nutrient solution. Make up dilute solution is fed through the valve line 40 into the top of the tank 18. Tank 18 has an air escape line 41 equipped with a sterile filter 43.

Primary nutrient solution is fed from the holding tank 16 and pumped by pump 42a through line 42 through the check valve 44 and open valve 46 in line 42 and the open valve 48 in line 32 to the inside of the tubular membrane 22. Once the inner reaction zone 26 is filled with a sufficient quantity of plant cells, the valve 50 in line 30 is closed. The valves 46 and 48 in lines 42 and 32, respectively, are kept open as long as the process is running, continuously feeding the primary nutrient solution to the inner reaction zone 26 to replenish nutrients as they are used up by the metabolic reaction of the cells growing inside the inner reaction zone. Make up primary solution is added through valved line 31 and air escapes through line 33 which equipped with a sterile filter 35.

As the cells grow within the inner reaction zone 26 the byproducts of the metabolism, the metabolite byproducts, move across the membrane wall 22a into the dilute nutrient solution in the outer reaction zone 28. This dilute nutrient solution is continuously pumped by the pump 52 in line 54, moving it through the outer reaction zone 28 out the top of the reaction zone through line 56 and line 54 to the input end of the pump 52 then out the output end of the pump through the check valve 54a and open valve 57 in line 60 into line 62 to be recycled to the lower end of the vessel 24. Make up solution may be added to this recycling stream of dilute nutrient solution by opening the valve 38. The check valve 36 prevents the recycling dilute nutrient solution from backing up into or flowing into the holding tank 18. When it is desired to draw off metabolite byproduct, the valve 64 in line 68 is opened and a portion of the recycle stream is directed by line 68 into the metabolite holding tank 14. A gas escape line 70 with a sterile filter 72 at its end allows air to escape from the metabolite holding tank as it is filled with metabolite product from the outer reaction zone. Two pressure relief valves 105 and 106, one in line 56 and the other in line 76, allow gaseous products to escape.

The cell product stream from the inner reaction zone 26 flows out the top of this zone through the line 76 as it is pumped by the pump 78 through line 80, check valve 82 and open valve 84 in line 86 into the bottom of the inner reaction zone 26. Thus the cell product stream is separated by cell separator 107 into small cells and clumps. After the clumps, the remaining cells are continuously recycled by the pump 78. Compressed air from an air compressor 88 is forced through a check valve 90 and open valve 92 in line 94 and open valve 48 in line 32 into the bottom of the inner reaction zone 26 to percolate small bubbles of air including oxygen through the inner reaction zone. This maintains an aerobic environment within the inner reaction zone 26. If desired, the conditions could be changed to maintain an anaerobic environment. Gas, however, would always be forced under pressure through the inner reaction zone 26 to create an ebullient gaseous environment to enhance the growth rate of the cell mass product within the inner reaction zone.

The following table sets forth the typical conditions maintained within the bioreactor 12 using a 36 inch long dialysis tube with a 0.5 inch diameter for a garlic cell product of the type manufactured in the demonstration unit 10 when the garlic cells of the Example are placed in the inner reaction zone 26 of the bioreactor.

TABLE

| | |
| --- | --- |
| Temperature | 25° C.–27° C. |
| pH | 5.0–5.3 |
| Velocity Inside Tube (recycle) | 0.005–0.05 feet/minute |
| Velocity Outside Tube (recycle) | 0.005–0.1 feet/minute |
| Cell Count | $1.5 \times 10^7$ cells/milliliter |

When it is desired to collect cell mass product the valve 96 in line 98 is opened and a portion of the cell mass product stream is directed through the line 98 into the cell collection tank 20. This tank 20 has a sterile filter 100 in line 102 which allows air inside the tank to escape as the tank is filled with collected cell mass.

In accordance with this invention, the cell mass product stream flowing through line 80 and the metabolite byproduct stream flowing through line 54 are monitored to determine the chemical composition of these streams. The monitoring is accomplished using the methods of this invention. Upon changing the concentrations of nutrients in the primary and dilute solutions, yields of cell mass product and metabolite byproducts are altered until the correct mix and concentrations of nutrients are developed to produce the highest yield of desired product. Thus, the demonstration unit 10 provides a quick and inexpensive means of:

a) checking the efficiency of the nutrient solutions.

b) growing small quantities of cell mass for test purposes.

c) obtaining preliminary engineering data for the design of a pilot plant.

d) changing process parameters quickly to improve cell growing techniques.

e) providing the initial pilot plant bioreactor cell charge.

Operation of Demonstration Unit

First, all lines, tanks, vessels, and equipment are sterilized and then the primary and dilute nutrient solution tanks 16 and 18 are filled. All valves are closed and the main air line 94 is charged at 3 to 4 psi of air pressure.

Next, about 180 ml of fresh garlic cells produced in accordance with the EXAMPLE at a concentration of $1\times10^5$ cells per milliliter is introduced into the bioreactor 12 through the valves 50 and 48 in line 32. Air from compressor 88 is injected into the bottom of the tubular membrane 22 by cracking the valve 92 on line 94. Pumps 34a and 42a are started. Then, valves 46 and 48 on lines 42 and 32 are opened to allow solution to enter the bottom of membrane 22. Next, the valves 38 and 57 on lines 34 and 54 are opened to allow dilute solution from the tank 18 to flow into the outer reaction zone 28.

At start-up the solution levels inside and outside the membrane 22 are kept the same until the cell count is $10^7$ cells per milliliter. At this point cells can be withdrawn to the cell collection tank 20. After the growing operation is underway, recycling of cell mass product and metabolite byproduct may be activated by opening the valves 57 and 84 and starting the pumps 52 and 78.

Cell mass and metabolite samples are taken periodically and analyzed for sugar content, pH, cell count and cell diameter, carbon dioxide, and dissolved oxygen. Preferably, the FT-IR spectrometer is used, with sampling and adjustment of process conditions being under computer control. Tests were performed in the demonstration unit 10 illustrated in FIG. 1. using the described nutrients solutions and a bioreactor 12 with ½" diameter dialysis tube, 36 inches long, produced 3.2 grams of garlic with a 12% moisture content in 9.3 hours.

Large Scale Production Facility

Figure 2:
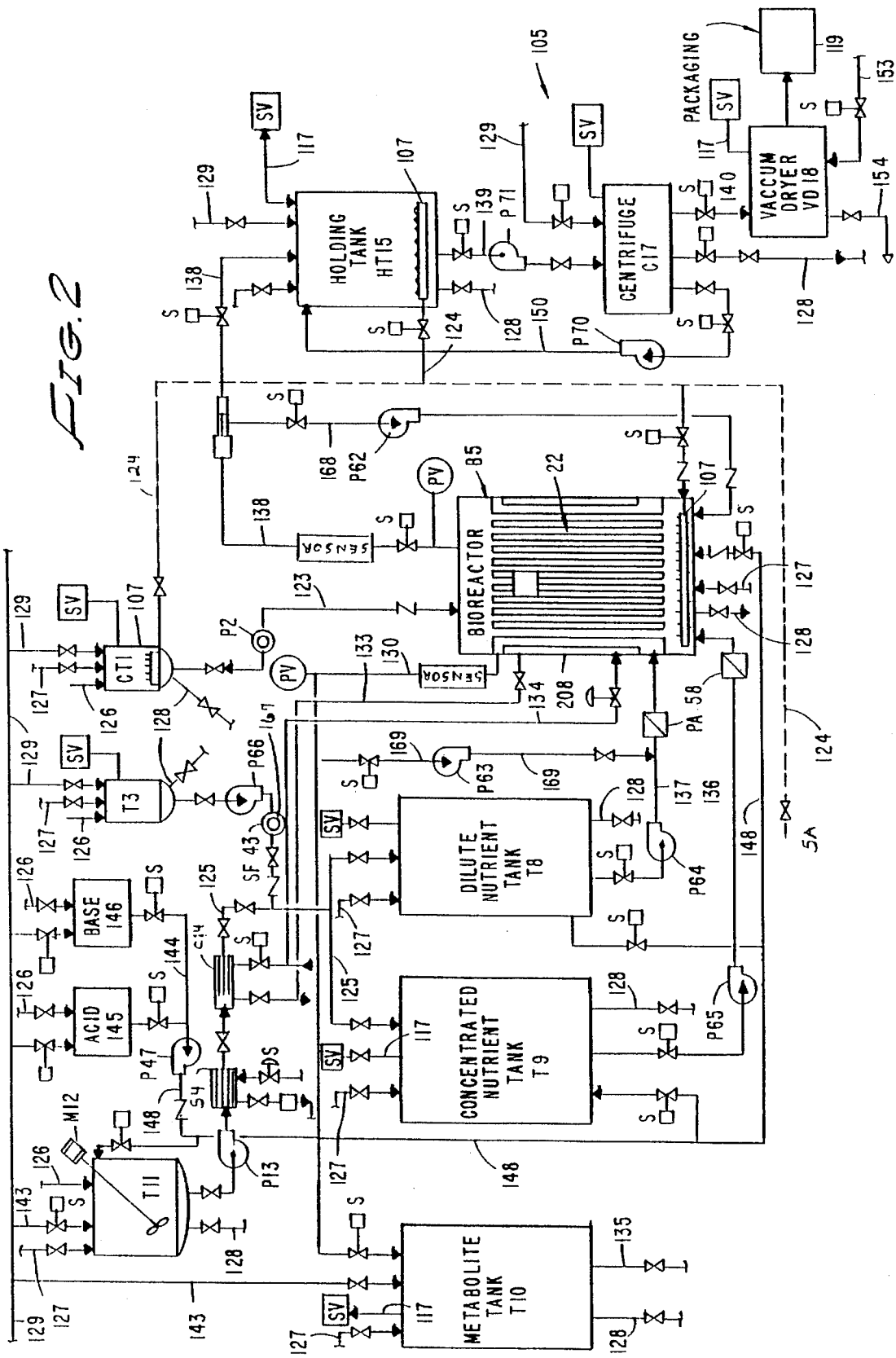
FIG. 2 is a schematic diagram showing a large scale production facility using the process of this invention.

The design for the production facility 105 illustrated in FIG. 2 is based upon the experience obtained from the design and operation of the demonstration unit 10. In this facility 105, the wetted surfaces of all equipment, the parts thereof, controls, and conduits are capable of withstanding steam sterilization and corrosion from the specific chemicals used in the process. In most instances, this means No. 316 stainless steel or polycarbonate polymeric material is used in their construction. The symbol "S" denotes a solenoid control valve. All equipment and lines are sterilized before operations can begin.

Cell Culture Supply Tank CT1

The first step is to fill Tank CT1 with a suspension of garlic cells from the demonstration unit 10. Air is supplied through line 124 to sparger 107 for agitation and enhancement the metabolic process. The symbol "SV" denotes a sterile vent and "SA" denotes sterile air.

Cell culture density is checked by drawing off samples through drain connection 128. When analysis indicates that cell count is above the critical mass required for rapid cell growth, the garlic cell suspension is pumped by pump P2 through line 123 into bioreactor B5.

Line 127 is for sterilizing by steam, or chemical sterilents such as ethylene oxide or sodium hypochlorite. Line 129 is to adjust cell density of the culture tank with sterile deionized water or wash out the system after charging the bioreactor or sterilization.

Bioreactor B5

The bioreactor B5 is the heart of the process. It is inside the dialysis tubes 22 supplied with concentrated nutrient solution from Tank T9 that cell growth and division occurs. Excess air for metabolic purposes is introduced into the dialysis tubes 22 through line 124 and sparger 107. Some air is directed towards the bottom of the bioreactor B5 to prevent cell build-up. The air agitates the cells and increases the rate of replication by constantly bathing them with fresh nutrient solution. Air also reduces biofouling on the inside walls of dialysis tubes 22, assisting in the transference of metabolic products into the dilute nutrient (metabolite) stream. Both of these reactions reduce the time for cell replication.

Concentrated nutrient solution from Tank T9 is supplied by pump P65 into the bottom of the bioreactor B5 through line 136 in an amount needed to replenish the amount of solution and newly grown cells removed to holding tank HT15. Dilute nutrient solution is pumped by pump P64 to the bioreactor B5 from Tank T8 through line 137 in an amount determined by the analysis in a monitoring system to be necessary to produce either the desired cell mass or metabolic byproduct in greatest amount and in the least amount of time.

The pH in the bioreactor B5 in which grow the garlic cells is maintained at about 5.4 by adding either acid or base by pump P47 through lines 144 and 148. Sodium hydroxide and hydrochloric acid may be used, but they create sodium chloride, which may be harmful to some plant cells. Therefore, the preferred acid and base in most instances are nitric acid and potassium hydroxide, which produce the salt potassium nitrate, a nutrient. Garlic cells are removed to holding tank HT15 through line 138 in order to maintain the efficiency of the bioreactor.

Newly grown cells (clumps removed) are recycled at the optimum rate (+or–50%) through line 168 by pump P62 to the bottom of the bioreactor B5. Metabolites are also recycled at the rate required for the maximum build-up of the desired product in the metabolite stream through line 169, pressure alternator PA58 and line 137 by pump P63.

Different kinds of cells demand different temperatures for optimum growth. Tests on garlic cells indicates that they do very well when grown between 60 and 65 degrees Fahrenheit. To maintain this temperature inside the bioreactor B5, cooling water is introduced into jackets 208 through line 134 and leaves through line 133.

Pressure alternators PA58 in lines 136 and 137 alternate the pressure to expand or flex the dialysis tubes 22 to slough off any cell materials which might cling to the walls of the tubes and prevent the transfer of nutrients or metabolic products. Line 127 is the bioreactor's sterilent wash connection. Line 128 is its sample test and drain connection.

In a production facility designed for the commercial production of garlic, batteries of parallel bioreactors B5 may be desired.

Cell Holding Tank HT15

The main purpose of this tank HT15 is to hold-up the effluent from the bioreactor B5 and grow the cells to a greater size and weight before the cells are centrifuged or separated. Line 138 carries the newly grown garlic cells from the bioreactor B5 to the holding tank HT15. The atmosphere in tank HT15 is 15 psig and sterile vented through line 117 of the excess sparger air and carbon dioxide created in the bioreactor B5 and the holding tank itself. Line 124 provides sparger air, line 126 is the sterilent connection and line 129 supplies sterile deionized water.

Instead of a cell holding tank such as HT15 the cells may be moved in a sterile manner to a chamber that contains a horizontal flat membrane supported over a nutrient solution or bathed in a nutrient solution with an aqueous media below the membrane. In this system the cells can be further grown until ready for harvest and the respective solutions on either side of the horizontal membrane can be treated as they are for the main bioreactor including monitoring and control provisions of this invention.

Centrifuge C17

Centrifuge C17 separates the cells from the nutrient solution. Its second purpose is to return the smaller cells still in the nutrient solution back to the holding tank HT15 by pump P70 and line 150. Its third purpose is to wash the centrifuged cells and remove all traces of the nutrient solution from them. The mixture of cells and nutrient solution is pumped from the holding tank HT15 through line 139 by pump P71 into a rotating basket screen (not shown) inside the centrifuge C17. Then, the relatively dry cell mass clinging to the side of the basket is sprayed with sterile deionized water from line 129 to remove the last vestiges of nutrient solution. Unless the economics are favorable, the wash water is wasted to the sewer through line 128.

Vacuum Dryer VD18

The equipment required for the last two operations depends upon the final form the product is to take. Assuming that it is to be a powder the cell mass from the centrifuge would be conveyed through line 140 to a vacuum dryer VD18 where the garlic cells would be dried to a powder with a moisture content no greater than about 10 percent. Steam for drying is supplied to a heating coil through line 153 and its condensate is returned to the boiler through line 154. Moisture and air would be sterile vented through line 117 and sterile vent SV. Line 154 is for draining the dryer. Packaging the garlic will be done in operation 119 in the kind of container customarily used by a food processing manufacturer.

Metabolite Tank T10

Tank T10 collects the garlic metabolites from the Bioreactor B5 through line 130 and stores them for further processing for valuable byproducts. Line 117 contains a sterile vent through which air is inhaled or exhaled during unloading or filling. Line 127 is the sterilent connection and 128 the sample-drain connection. Line 135 is the unloading connection and line 143 is the sterile deionized wash-water connection.

Concentrated Nutrient Solution Tank T9

Tank T9 receives the concentrated nutrient solution from mixing tank T11 through line 125 and stores it for delivery to the bioreactor B5 through line 136 by Pump P65. Line 117 is the necessary sterile vent, line 127 the sterilent connection, line 128 is the sample-drain connection and line 125 is the means by which sterile vitamins, hormones, and deionized water are delivered. Deionized water is used for concentration adjustment or wash down. Line 148 provides acid or base for the adjustment of the pH.

Dilute Nutrient Solution Tank T8

Tank T8 receives the dilute nutrient solution from mixing tank T11 and stores it for use in the bioreactor B5. Line connections are identical to those of tank T9 except for line 137 which delivers the dilute nutrient solution PA58 by means of pump P64 to the bioreactor B5. Pressure alternator on line 137 is the means by which the dialysis tubes 22 are flexed to slough off any cell material which might clings to the tube walls.

Ancillary Equipment

Nutrient Mixing Tank T11

The macro and micro salts required for the garlic's nutrient solutions are preweighed and mixed by mixer M12 with the correct amount of deionized water in tank T11. The pH of the mixture is adjusted by pumping either acid or base from Tanks 145 and 146 by pump P47 through lines 144 and 148. When ready, the mixture is pumped by Pump P13 through line 125 to sterilizer S4 then cooler C14 where it is reduced to ambient temperature before entering concentrated nutrient supply tank T9.

The dilute nutrient solution for the garlic is made in the same way as the concentrated solution except that amount of sterile deionized water used is ten times greater.

Line 126 is the conduit through which the preweighed nutrient salts are added to tank T11. Line 127 is the sterilent line and line 143 is for the addition of deionized water. Line 128 is the sample-drain connection.

Vitamin and Hormone Mixing Tank T3

The hormones and vitamins are mixed separately and added directly to the nutrient supply tanks T8 and T9 because they decompose under heat and must be filter sterilized. The vitamins and hormones are solvated and added to tank T3 through line 126. If necessary additional sterilized deionized water can be provided through line 129. When ready, the mixture of hormones and vitamins are supplied by pump P66 through line 167 and sterile filter SF43 into line 125 and then to the nutrient supply tanks T8 and T9. To insure thorough mixing in these tanks the vitamin and hormone mixture should be pumped into tanks T8 and T9 before the nutrient solutions from tank T11 are pumped into them. Line 127 is the sterilent connection and line 128 the sample-drain connection.

pH Adjustment Tanks T45 and T46

The nutrient solutions are adjusted to a pH range between 5.2 and 5.6 for optimum garlic cell growth. This is accomplished by supplying either acid or base directly from tanks 145 and 146 to mixing tank T11 in the proper amount through pump P47 and lines 144 and 148. The pH of the cell solution inside the dialysis tubes 22 of the bioreactor B5 has a tendency to rise during metabolism. To maintain a constant pH, acid is added to the bottom of the bioreactor B5 through line 148. Line 126 is the acid or base fill line for tank 145 or tank 146. Line 143 is for the addition of sterilized deionized water as either a dilutant or wash-water. Nutrient supply tanks T8 and T9 can be washed down through the pH adjustment tanks 145 and 146 or the mixing tank T11. Line 127 is the sterilent connection and line 128 the sample drain connection.

Process Control

Bioreactor B5 is the principal point of control for the entire process. Sensors in exiting cell mass line 138 monitor and control the flow rate, the number of cells per milliliter, the separation and recycling of the cells according to their size, pH, temperature, sugar content, dissolved oxygen, dissolved nitrogen, and dissolved carbon dioxide. Sensors in the exiting metabolite stream line 130 monitor and control the flow rate, concentration of metabolites, pH, temperature, sugar content, dissolved oxygen, and dissolved nitrogen. Solenoid valves S installed in the appropriate lines from other tanks and equipment insure the satisfactory and efficient operation of the bioreactor B5.

Nutrient tanks T8 and T9, in addition to supplying solenoid valves S controlled by the flow sensors in lines 138 and 130, are equipped with level controls, automatic alarms, and pH sensors. Holding tank HT15 is equipped with all the controls required to make it a self-operating but within the control of the overall process.

Controls are installed on Centrifuge C17 to make it operate automatically with holding tank HT15. The controls of other ancillary equipment such as the pH adjustment tanks, heat exchangers, hormone and vitamin tank, etc. are designed to allow them to operate automatically within the requirements of overall process.

A centrally located computer monitors, records, and controls all process variables and equipment responses required for the satisfactory operation of the process. The computer can be the same computer in which all of the monitoring and control calculations and functions are performed. In one embodiment of this invention all of the functions were combined in a single 80286 level computer which automatically handled all measurement and solenoid operation controls.

BIOREACTOR

The large scale bioreactor B5 is illustrated in FIGS. 3 through 7. This bioreactor B5 includes a plurality of generally vertically oriented dialysis tubes 22 arranged parallel to one another and contained within a reaction vessel 200 having removable heads 202 and 204 located at the top and bottom of the reaction vessel. The heads 202 and 204 are removably connected to a cylindrical member 206 having the cooling jackets 208 extending about the circumference.

Figure 4:
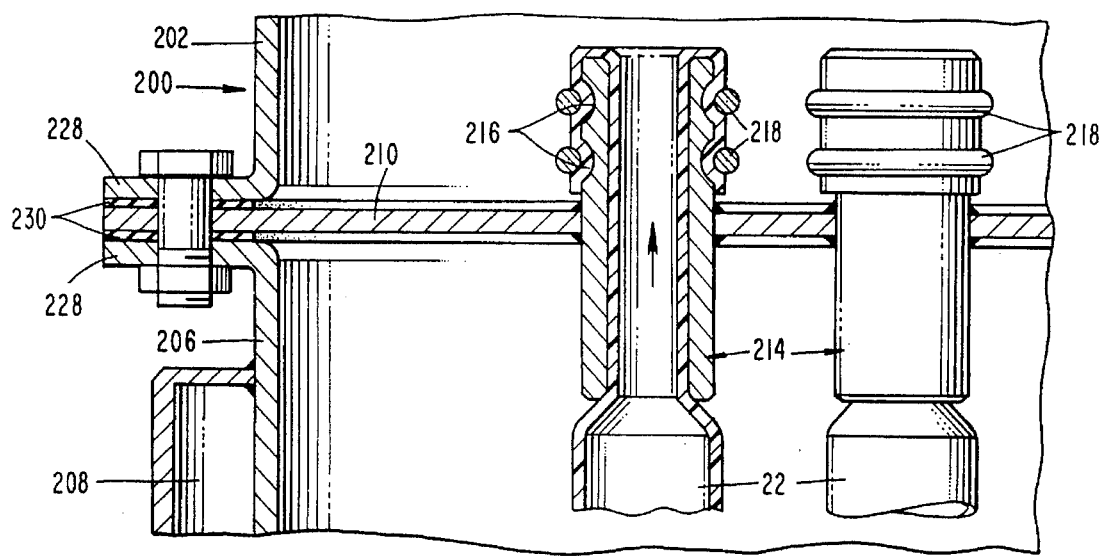
FIG. 4 is an enlarged, fragmentary, sectional view taken along line 4—4 of FIG. 3.
Figure 5:
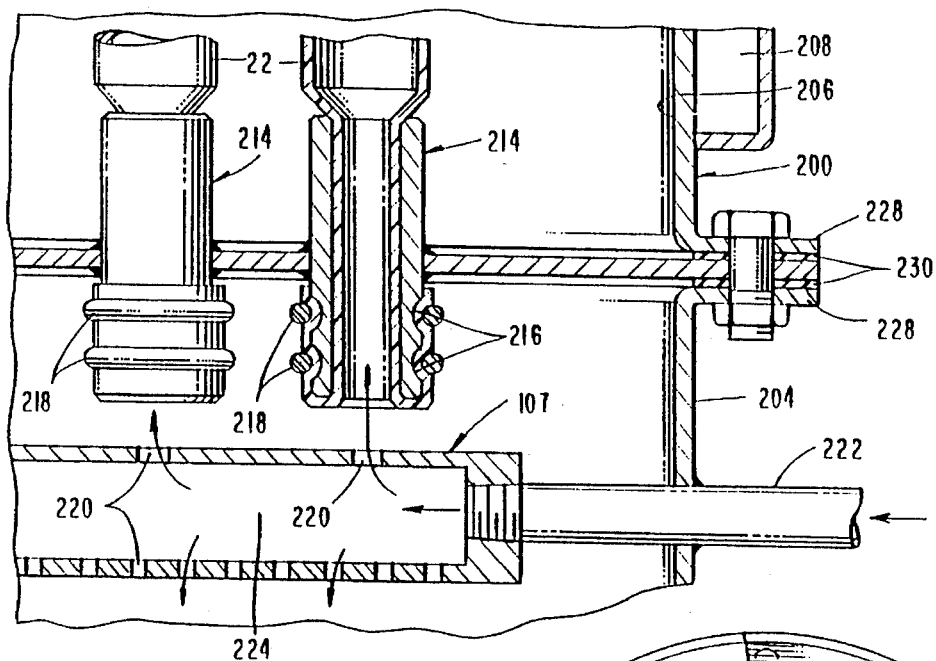
FIG. 5 is an enlarged, fragmentary, sectional view taken along line 5—5 of FIG. 3.

The vessel 200 includes both a top and bottom plates 210 and 212. Each of these plates 210 and 212 have a plurality of nipples 214 which extend through the plates and are, for example, welded in position. The outer portion of each nipple 214 has a pair of annular groves 216 therein. As best illustrated in FIGS. 4 and 5, the tubes 22 are at their ends constricted and drawn through the nipples and folded outwardly so that end portions of the tubes cover the annular groves. Pairs of 0-rings 218 are slipped over the ends of the tubes 22 and hold the tubes firmly in position.

At the bottom of the reaction vessel is the sparger 107 having a plurality of orifices 220 both in its top and bottom. Gas under pressure is forced through the gas inlet 222 to fill the interior chamber 224 of the sparger and force gas bubbles out the orifices 220. Preferably, the orifices 220 are aligned with the lower ends of the tubes so that air moves upwardly into the interior of the tubes. If an anaerobic reaction is being conducted carbon dioxide is forced through the inlet 222 rather than air. In the exterior of the vessel is an observation window 226 which allows the interior of the vessel to be observed.

In assembly, the tubes 22 are placed in position on the plates 210 and 212 and then the plates are placed between the upper and lower headers 202 and 204 with the tubes extending between the plates. The plates 210 and 212 are then bolted in position at the flange portions surrounding the headers and central cylindrical portion of the reaction vessel. Seals 230 are placed in portion between flanges 228 and the plates 210 and 212 to prevent leakage. Water flows into and from the cooling jackets 208 to regulate the temperature of the liquid on the interior of the vessel 200. The tubes 22 are immersed in the aqueous medium which is fed to the inside of the cylindrical member 206 of the vessel. The cellular material fills the head 204 and flows through the tubes 22 upwardly.

The bioreactor B5 and its controls assures: the introduction of sterile cells into the dialysis tubes, the flow of right amounts of concentrated and dilute nutrient solutions, optimum bioreactor- temperature, pH, cell density, excess air or nitrogen, the removal of unused air or nitrogen and metabolic gases, the growth and removal of new cell mass, the creation and removal of metabolites, flexible dialysis tubes 22 to prevent the build-up of cells inside the walls of the dialysis tubes which prevent metabolites from crossing through the membrane.

The preferred material of construction for the body of the bioreactor B5 is 316 stainless steel. The tubes 22 are made from cellulose acetate or polysulfone of the cut-off (Daltons 500 to 500,000) required by the product grown. Any plastic material used must be autoclavable like polycarbonate or its equal.

| | |
|---|---|
| Diameter | 36 inches, excluding cooling jacket. |
| Length | 48 inches, tube length, overall 66 inches. |
| Tubes | 340 - ½, inch diameter |
| Output | 30.6 pounds (dry) per day (estimated) |

The bioreactor B5 may be installed vertically. This is desirable for the following reasons: First, because the dialysis tubes 22 are flexible, and to function well, they preferably are upright. Second, because the tubes 22 are attached to the tube sheet nipples, they are installed in a special manner. Third, because air from the sparger 107 is directed through a separate nozzle into bottom of each dialysis tube where it flows upwards to be highly effective.

The bioreactor B5 is assembled in a special way with a special wire tool. The top and bottom tubes fastened to the nipples in the position they will occupy in the assembled bioreactor. Then, plates 210 and 212 and cylinder member 206 are placed on a raised jig to make tubing easy. The dialysis tubes 22 are precut to 54" and installed one at a time by a wire tool which is inserted inside and clipped to the top and bottom of the tube. Tube and tool are thrust through the top tube nipple 214, down through the matching bottom tube nipple. The clip from the top of the tube is removed and the tube folded back over the nipple and fastened in the grooves 216 with the "O" rings 218. Then, the bottom part of the tube 22 is fastened in the same way after a little slack has been left to allow the tube to flex and move slightly. Care is taken not to leave too much slack otherwise the tubes 22 will rub against each other and wear out prematurely.

When all the tubes have been installed, the top and bottom headers 202 and 204 are gasketed with seals 230 and bolted in place,and the bioreactor B5 is ready to be used.

j) The bioreactor B5 is designed to be taken apart easily so that its tubes 22 can be changed with minimum effort.

k) The working or exposed length of the dialysis tube 22 are 202 and 204 slightly greater than the actual distance between the headers to allow the bioreactor B5 to be assembled. However, care must be taken not to make the tubes 22 so long that they rub against each other.

l) Four glass windows 226 eight inches in diameter allow a view of what is occurring inside the bioreactor.

IR MONITORING TECHNIQUE

Figure 8:
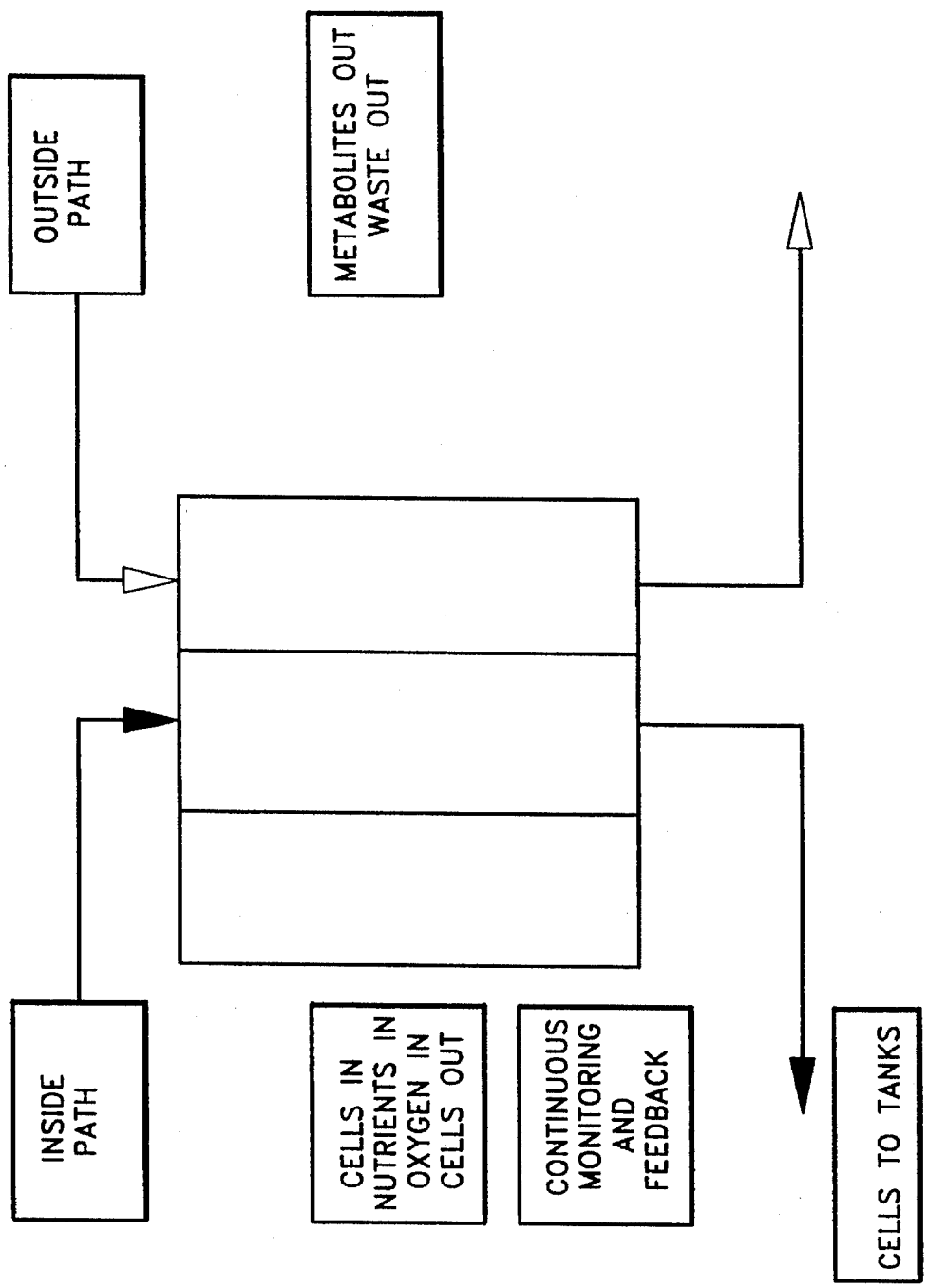
FIG. 8 is a schematic illustration of a model bioreator using a tubular membrane.

A simple engineering model is presented for the tubular membrane bioreactor depicted in FIG. 8. This bioreactor is based on the use of porous membrane tubing (e.g. dialysis tubing) contained in cylindrical shells large enough to maintain an approximate 3.25 to 1 area ratio between the inside and outside parts. Because this ratio, as well as the surface to volume ratio, does not change, no matter what the size of the bioreactor (multiple tubes are manifolded for larger sizes), scale up to larger sizes should be easier than conventional processes. The major difference in operation of larger scale equipment will be the function of peripheral equipment and not the bioreactor itself.

It has been determined, in experiments with both plant and microbial cells, the standard methods for analyzing mass transport lead to a model wherein three major parameters characterize the performance of the bioreactor for a given type of cell. These parameters are:

1. $k_u$, the rate constant for the use of nutrients (e.g. carbon source) by the cells.

2. $K_j$, a factor which describes how the membrane modifies the free solution self diffusion constant for any chemicals species, j, in the system.

3. $E_u$, the efficiency of conversion of the nutrients to the desired cell product.

These parameters can be determined empirically through use of the continuous on-line chemical monitoring system which has been developed. The effects of pH, temperature, media composition, dissolved oxygen and cell size and concentration can also be taken into account. The parameters can all be dynamically dependent on conditions and do not need to be constants.

Results are presented showing that experimental data from several trial runs of a well characterized cell line of yeast (*Kluveromyces marxianus*) follow the model closely. Plant cells (garlic suspension cultures, bamboo suspension cultures and carrot suspension cultures) have also been used.

Engineering Model

A preliminary engineering model for the Tubular Membrane Bioreactor in its most widely tested configurations is set forth below. Although many other configurations are possible, the system using normal dialysis tubing (cellulose acetate with varying molecular weight cut off) inside polycarbonate tubes appears to be the most economical.

A yeast, *Kluveromyces marxianus*, a well known food yeast which is carbon limited in normal growth, was selected for modeling purposes. Similar runs were made with *Saccharomyces cerevisiae* which follow a similar path. For studying cell growth, *S. cerevisiae* has the drawback that at sugar concentrations above 1% the yeast will convert a large percentage of the sugar to ethanol fermentatively even with a high oxygen content in the media. Since it is the objective to see how far the system can be pushed, i.e. to maximize the sugar utilization for conversion to cell mass, *K. marxianus* is a better choice.

Sucrose was used as the carbon source and the parameters monitored included sucrose, glucose, ethanol, pH, dissolved oxygen, temperature and transmission through the system at 633 nm. The bioreactor had 8 channels of continuously recording physical information available as well as up to 20 or so chemical components. All channels can be monitored on-line continuously.

The process is best understood by considering that the flow streams for the inside and the outside of the membrane are independent except for diffusion of material across the membrane. When considering the above parameters, it should be noted that there will be two values simultaneously for all the parameters: one describing the average value inside the membrane and another describing the average value outside the membrane.

Since all of this mass of data can be continuously recorded, the question becomes one of developing a consistent method for using the information. The information is collected on computer disk in time sequence data files which are to be used for proprietary control algorithms. The following presents a simple model, rather than a control algorithm, which can be expanded to cover many other items of interest and can be expanded into a control algorithm.

The System With No Cells

To begin consideration of the membrane bioreactor system we first describe the system with no living cells. We will consider the empty system into which we add a water solution of sucrose into the inside section of the membrane with only water on the outside. If we let:

$C_i$=the concentration of sucrose inside the membrane at time t $C_o$= the concentration of sucrose outside the membrane at time t P= the permeability of the membrane A= the total membrane area $V_i$= the volume inside the membrane $V_o$= the volume outside the membrane $C_i(0)$ and $C_o(0)$ will refer to the values at time t=0. For this system we will use the concentrations as moles/cm$^3$, time in seconds and volume in cm$^3$. Then, for any time t.

$$\frac{dC_i}{dt} = -\frac{PA}{V_i}(C_i - C_o) \quad [1]$$

$$\frac{dC_o}{dt} = \frac{PA}{V_o}(C_i - C_o) \quad [2]$$

The permeability of the membrane is usually taken as $$P = \frac{DK}{h} \quad [3]$$

where D is the self diffusion constant (about $5.21 \times 10^{-6}$ cm$^2$/sec for sucrose), K is a factor which accounts for the fact that the membrane is not totally water permeable (K is usually 1 to $10^{-7}$ depending on solute species and membrane type) and h is the membrane thickness. Equation (3) can be derived from Fick's Law of diffusion. The entire set of equations is repeated for any solute species which, as in this example, is anticipated to act independently.

In general P is not constant with concentration since neither D nor K can be expected to be constant. In all of the modeling we use several numerical techniques to solve simultaneously the two sets of equations. In the numerical methods, a small time step can be used and the value of P can be change with the steps as data shows it should be so changed. The functionality of P with concentration species through the membrane with time using the system (1) and (2) to determine the value of P over the concentration ranges of interest ($C_i$ and $C_o$).

Subsequently, superscripts j will be used to denote multiple species. However, to keep the notation simple, it should be kept in mind that whenever (1) through (3) are written, they are written for a particular species. It is also recommended to use the fourth order Runge-Kutta technique for these two equations and the others herein when one wishes to change P as a function of $C_i$, $C_o$ or t. When more equations are coupled together, for example when we consider glucose produced by the inversion of sucrose with a concentration varying rate constant, we may have to resort to more sophisticated techniques.

It is pointed out that (1) and (2) have the following solution if P is constant for the time period concerned:

$$C_i = \frac{a}{[1+b]} + \frac{([1+b]C_i(0) - a)}{[1+b]} \exp\left(-\frac{PA[1+b]t}{V_i}\right) \quad [4]$$

$$C_o = \frac{S_n - C_i V_i}{V_o} \quad [5]$$

$$a = \frac{S_n}{V_o} \quad [5a]$$

$$b = \frac{V_i}{V_o} \quad [5b]$$

$$S_n = C_o(0)V_o + C_i(0)V_i \quad [5c]$$

These equations can actually be used to obtain values of P (actually K since D and h are known) from segments of the data using the concentration of sucrose with time on both sides of the membrane. It was found that a good average value for K was 0.1 leading to a permeability around $5.2 \times 10^{-5}$ cm/sec for the ranges of concentration between 3 and 7 mass percent of sucrose in water.

For all of the work a three foot long version of the bioreactor was used. This leads to the following values for the parameters:

A=442 cm$^2$
$V_i$= 277 cm$^3$
$V_o$=676 cm$^3$

It should be noted that the values for the volumes include approximately 100 cm$^3$ of space in plumbing outside the bioreactor proper that still is part of the inside and outside system. The actual volumes inside and outside the membrane are therefore 177 cm$^3$ and 576 cm$^3$ respectively keeping the 3.25 to 1 ratio.

The bioreactor in this size is approximately equivalent to a 1 liter system. This should be kept in mind when considering the information to follow.

The System With Cells

When sucrose is added to the inside of the membrane while the membrane contains living cells capable of utilizing the sucrose equation (1) and (2) become:

$$\frac{dC_i}{dt} = -\frac{PA}{V_i}(C_i - C_o) - k_u C_i \quad [6]$$

$$\frac{dC_o}{dt} = \frac{PA}{V_o}(C_i - C_o) \quad [7]$$

where $k_u$ is the first order reaction constant for the conversion of sucrose to other forms as used by the cell. It should be noted that it is not necessary that the reaction be first order or that $k_u$ be a constant. Any functional description can be accommodated by the choice of numerical method for solving the system (6) and (7). Note that equation (7) is identical to (2). The major difference in solubility is that equations (1) and (2) can be solved with the help of the simplifying assumption that the number of moles of sucrose remains constant with time while no such simplification is possible for (6) and (7).

It was found that $k_u$ was a weak function of concentration in the range from $4.2 \times 10^{-5}$/sec to about $7.2 \times 10^{-5}$/sec. Next consider the means by which these values were derived. First, however, it should be recalled that we have used an independent experiment with no cells in the system to determine the value of the permeability P. Thus, in (6) and (7) we could ask the question as to what the value of $k_u$ must be to obtain the best fit to the data. Thus, in each case we are only finding one unknown from the data. After we determine $k_u$ from the concentration vs. time profiles, we can determine the amount of sucrose used as a function of time. By determining the actual mass of cells produced over the same periods of time we can also determine the conversion efficiency of sucrose to cells.

In our actual analysis we approached this in a different manner. We did not solely "fit" the data to obtain the value of $k_u$. We had available to us continuous on-line monitoring of the turbidity, or actually the transmission, through the cells suspended in the fermenter. This enabled us to develop rate constants for cell growth from the first order assumption for cell growth.

It was then assumed that the rate of cell growth is the same as sugar disappearance. We also "fit" the data to find the value of $k_u$ independent of the turbidity data. The agreement was excellent for all times except for the very early start up period in the reactor where the rate of cell growth seemed to exceed the rate of sugar utilization probably due to a different functional relationship in either (6) or (8) than the first order dependence assumed. For many hours and days, however, the values tracked quite well. From a mass balance on removed cell mass (using filtration and weighing) we appear to have an efficiency of utilization of about 25% of the sucrose that was used.

Results of Several Runs

To minimize cost and time, only the inside or the outside of the membrane need to be continuously monitored. The FT-IR monitoring system can be sterilized and kept sterile using the flow through cell. However, for these runs we wanted to measure the concentrations both inside and outside simultaneously. We therefore sampled the inside and outside streams at their outlets where they leave the system without breaking sterility and then analyzed them manually. The system was run for 10 days and the following data is indicative of portions of the run.

Figure 9:
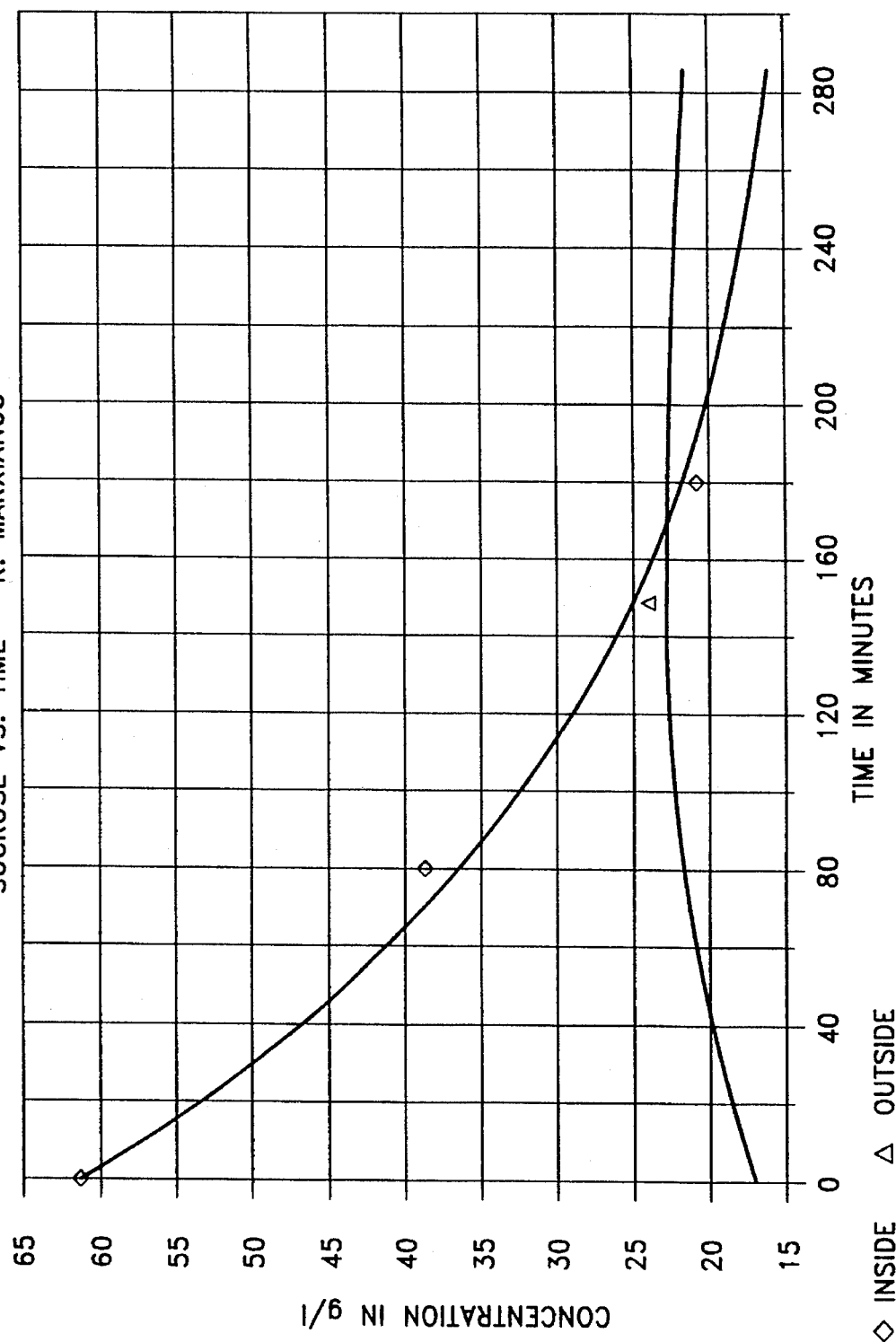
FIG. 9 is a graph of the concentraions of sucrose both inside and outside the reaction zone verses time for an experiment identified as KLUA1.

FIG. 9 shows the results of a 200 minute segment of operation with *Kluveromyces marxianus* growing in the bioreactor. The concentration began with the inside at 61 g/l of sucrose and the outside at 17 g/l. The line from the upper left descending to the lower right is the computer prediction of the decrease in sucrose concentration on the inside with time under the values of the parameters provided above for this particular bioreactor. The lower line is the computer prediction of the increase in sucrose in the outside solution. The diamonds represents two measured concentration points that were the furthest from the predicted line. The reason for the discrepancy (other than the usual limitations on accuracy in the determinations) is related to the change in $k_u$, the rate constant for use of sucrose by the cells in this reaction. The rate varied from $5.56 \times 10^{-5}$/sec to $7.35 \times 10^{-5}$/sec over the 3 hour period. The model could be made to better relate to the data by using other than a smooth changing function for $k_u$.

Since this and other segments (see below) appear to be "close enough" the extra afford did not appear warranted.

Figure 13:
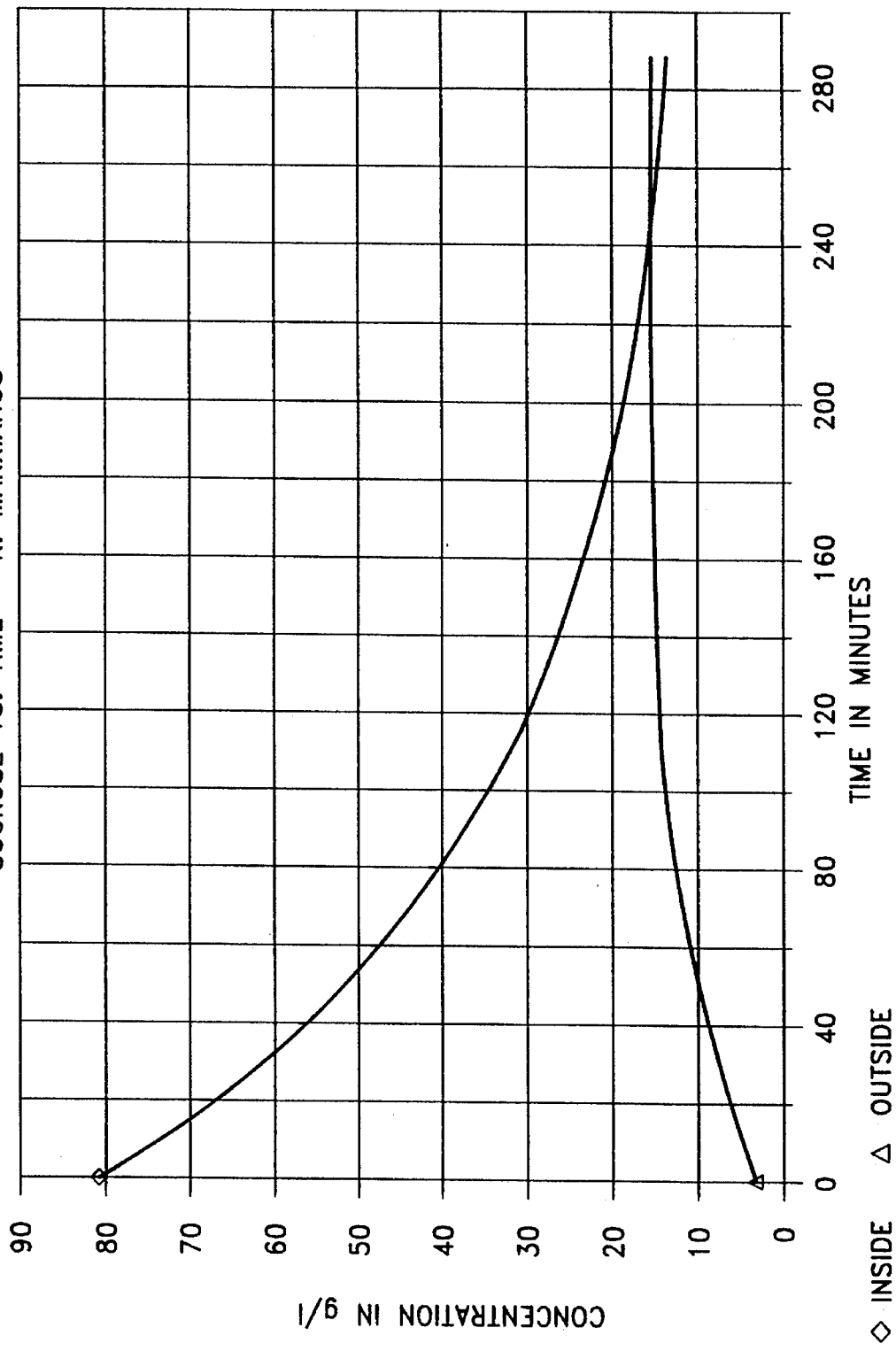
FIG. 13 is a graph of the concentraions of sucrose both inside and outside the reaction zone verses time for an experiment identified as KLUA3.
Figure 14:
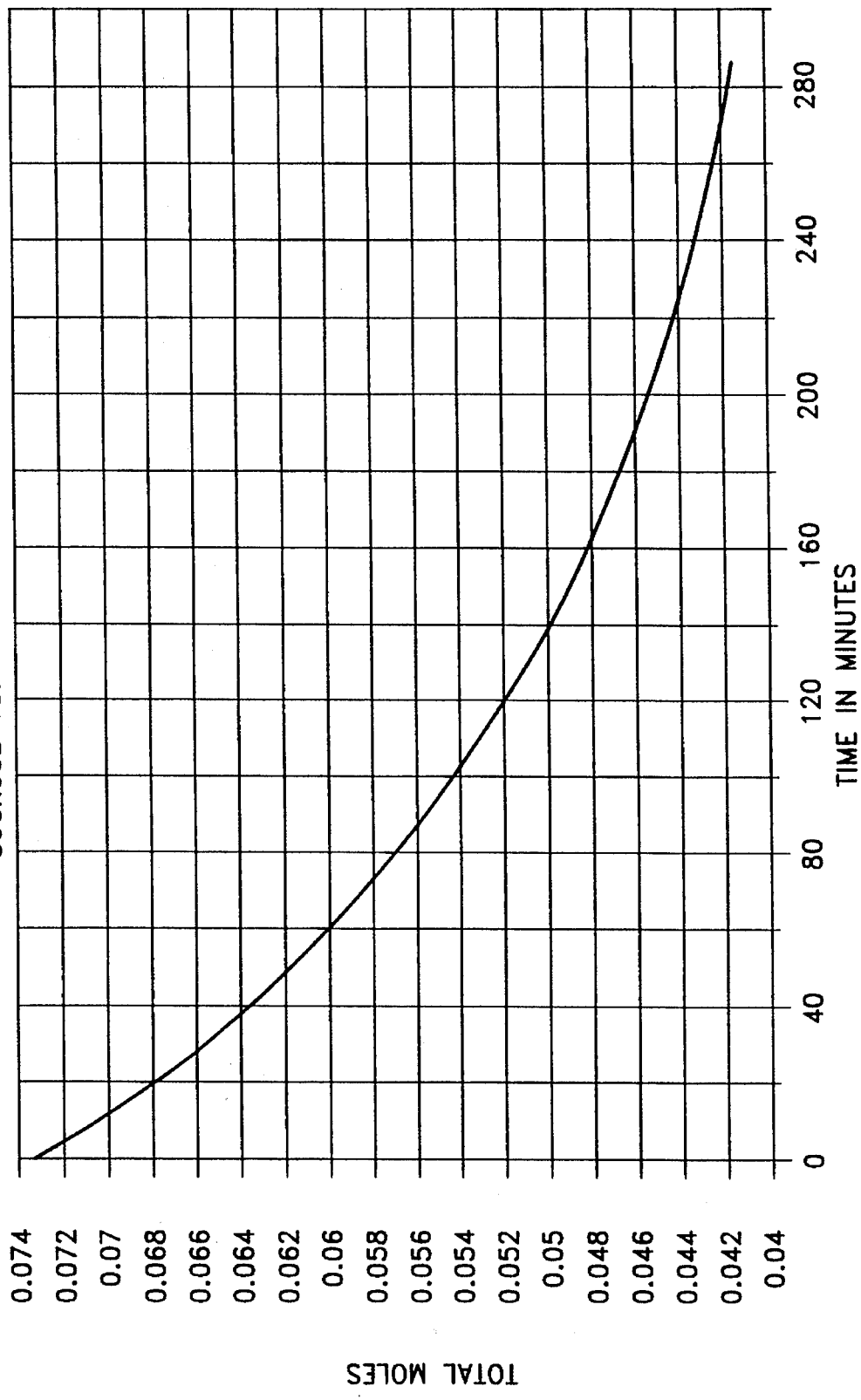
FIG. 14 is a graph of the total molar concentration of sucrose verses time for the experiment identified as KLUA3.

It should be noted in FIG. 9 that the outside concentration falls below the sucrose curve as actually measured. This is true in FIGS. 11 and 13 to follow and is due to the fact, at least partially, that we have not taken into account the loss of sucrose to other reactions such as the inversion to glucose and fructose. If small amounts of sucrose are being converted to glucose on the outside of the membrane, which by measurement we know to be the fact, then the concentration gradient is greater than that used in the model. This means that more sucrose will by pushed through than predicted as shown. Presumably, inversion inside is not so important since glucose and fructose are more readily utilized by the yeast than sucrose. Modifications to the model that account for this are given below. Once again, however, such a modification does not detract from the general quality of the simple model. The triangular point shown is the point at which the deviation from the predicted values were the greatest.

Note that with living cells in the inside membrane, the inside concentration drops below the outside concentration when the utilization rate is faster than the diffusion rate. If one lets the system continue without feeding in more sugar, the outside sugars would diffuse back inside. In other examples, the inside cells were fed by nutrients placed on the outside of the membrane. However, our purpose is to obtain the fastest growth rates which, in general, will mean feeding in nutrients at a sufficiently rapid rate to prevent the slowdown of growth while avoiding losses of nutrient to the outside aqueous medium. In this case we "feed" the inside system again at 200 minutes as will be explained below.

Figure 10:
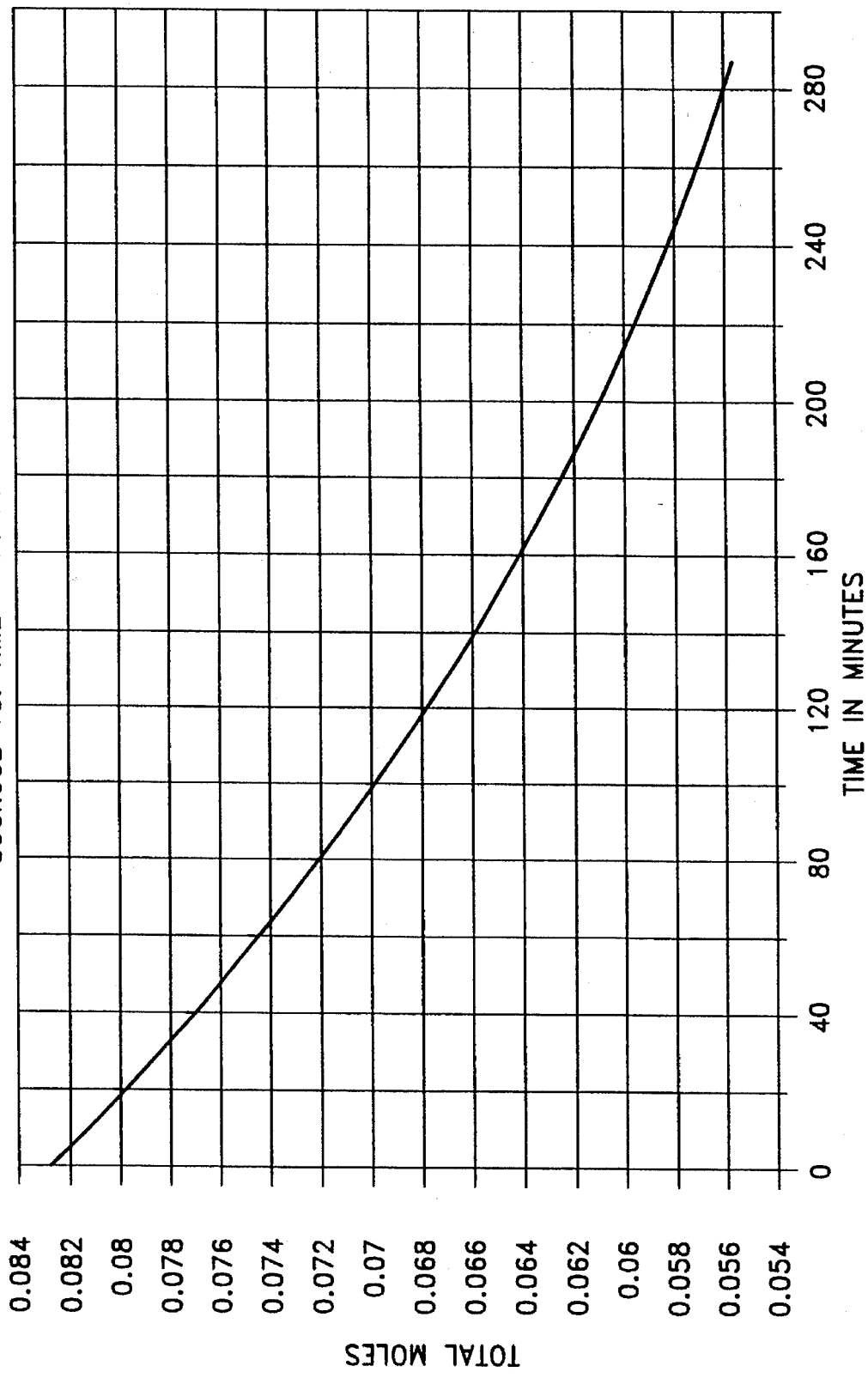
FIG. 10 is a graph of the total molar concentration of sucrose verses time for the experiment identified as KLUA1.

First, however, FIG. 10 shows the amount of sucrose "lost" during the process. This is the deficit obtained by mass balance and should be related to the amount used by the cells. Note that we began this segment with 0.083 moles of sucrose and at 200 minutes we only had 0.061 moles left. We thus used 7.5 grams of sucrose during this period. With an accurate weight of cells produced we can determine a conversion factor of sucrose to cell mass. Based on measurements made by filtering and weighing withdrawn cells at the end of the period and accounting for the volume, we estimate the conversion efficiency to be about 25%.

This measurement is made by withdrawing ⅓ of the volume of the inside after each period for which addition of more nutrient is required. The assumption is made that the concentration in the withdrawn sample is representative of the total volume. This is somewhat in error because the outlet to the inside line has a "separator" which collects predominantly larger particles. This error is small for yeast since they do not appear to aggregate in the system but it could be substantial for plant cells. Nevertheless, averaged over many periods of time, the mass of withdraw cells must balance with added nutrients.

Figure 11:
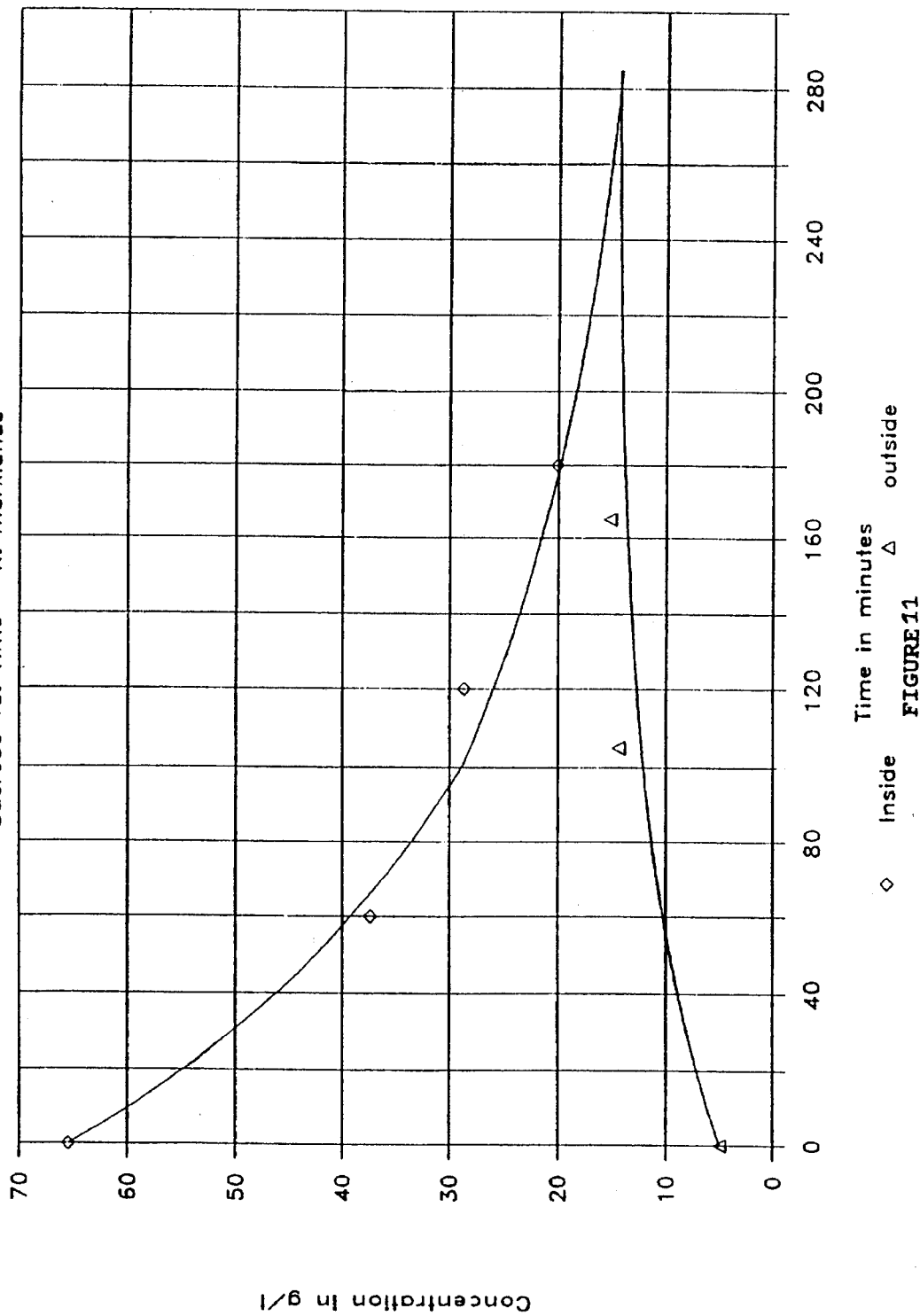
FIG. 11 is a graph of the concentraions of sucrose both inside and outside the reaction zone verses time for an experiment identified as KLUA2.
Figure 12:
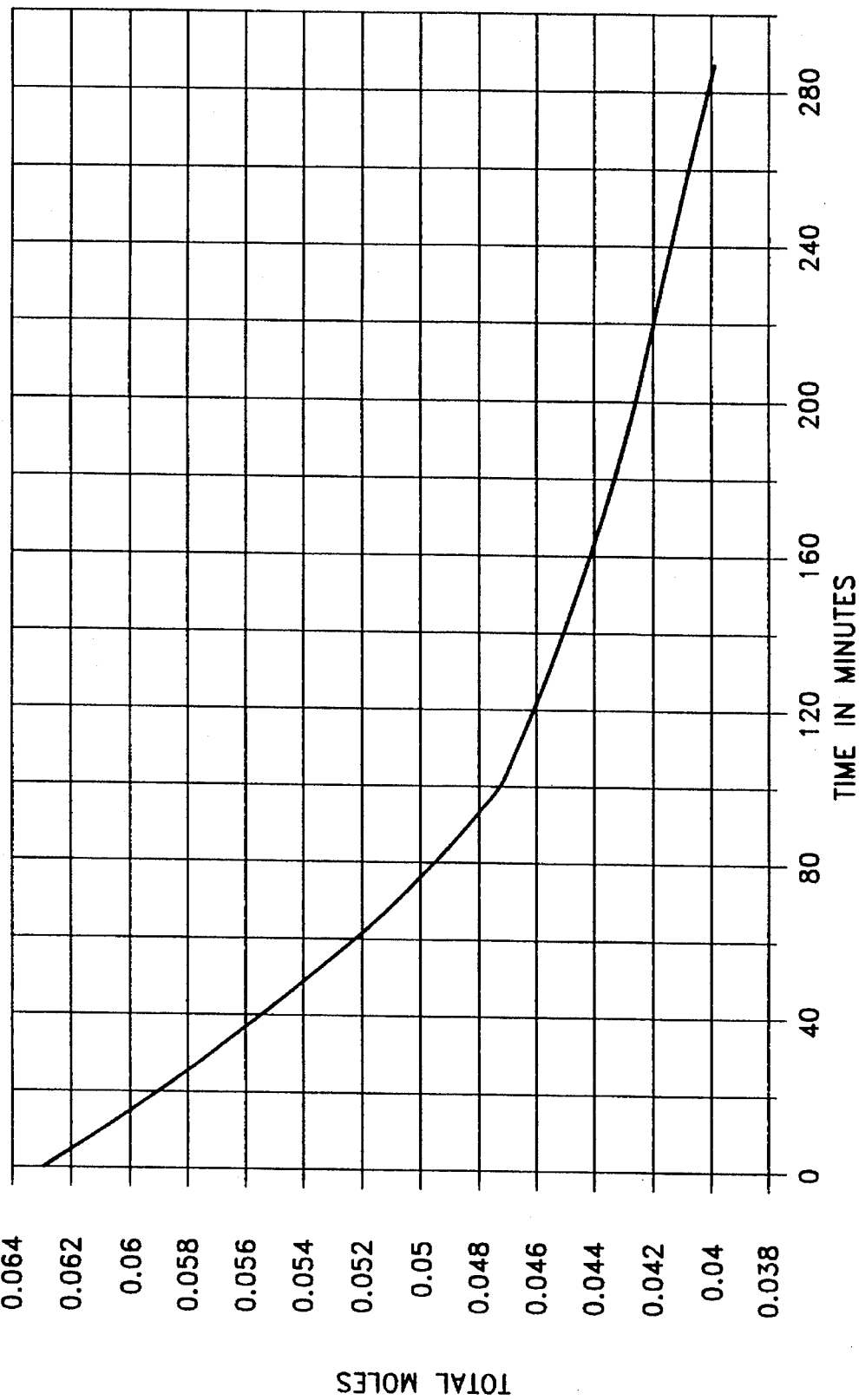
FIG. 12 is a graph of the total molar concentration of sucrose verses time for the experiment identified as KLUA2.

FIGS. 11 and 12 show the results for the next segment of time. At the 200 minute mark of the previous FIGS. 9 and 10 (Segment KLUA1) we fed new nutrient into the inside and swept unwanted metabolites out of the outside. The initial concentration for segment KLUA2 on the inside was 65 g/l and the outside was 5 g/l.

Note that the pattern agrees well with the worst points shown the outside predicted values are a small amount below the points, again presumably due to sucrose inversion on the outside of the membrane. As noted before, inversion on the inside will not have the same effect because the cells use the invert sugars faster and the rate is imbedded in $k_u$.

Segment KLUA2 showed a larger rate for $k_u$ at the beginning ($7.22 \times 10^{-5}$/sec) decreasing as the run went on to $4.17 \times 10^{-5}$/sec.

This resulted in an interesting observation. In the first segment, the rate increased with time while in the second segment it decreased. Examination of the pH and dissolved oxygen data showed the problem. While the pH held nicely at 4–4.5, the dissolved oxygen had dropped from 5 ppm in the first segment down to 2–3 ppm in the second segment. The effect is rather dramatic and made a major impact in the rate measured at around 100 minutes. If one examines the inside concentration curve closely the "kink" can be seen in the region where the rate change was noted by transmission measurements and the model corrected accordingly.

FIG. 12 shows the sugar utilization which was only 6.9 grams for this segment. The downturn in cell growth brought about by the lowering of the dissolved oxygen is definitely noticeable. As noted earlier, we also monitored ethanol during these series of runs and an increase in ethanol (although still small) was noted at this point.

When we discuss glucose and ethanol in this specific example we should note that they still can safely be ignored to understand the simply model. While sucrose values fluctuate between 61 and 5 grams per liter, for example, the glucose and ethanol were in the range of 1 to 10 grams per liter combined.

In the next segment, KLUA3, we increased the concentration of sucrose in the feed to 30% from 20%. In the previous segments we could only get initial concentrations of 60–70 g/l of sucrose at the beginning of the segment. By increasing the feed to 30% and initial concentration of 80 g/l was achieved at the beginning of KLUA3. This segment was run until the concentrations were equal at about 240 minutes. The sucrose use rate went from $7.2 \times 10^{-5}$ down to only $6.87 \times 10^{-5}$. The system used 10.4 grams of sucrose during the segment which is better, on a per hour basis, than either of the other two segments.

Maintaining a utilization rate of 2.6 grams of sucrose per hour would lead to a continuous production rate of cells of 15.6 grams per liter per day continuously. This is in keeping with the best rates reported for these yeasts in small tank, high oxygen content systems. The model is quite predictive and, since the conditions are not necessarily the optimum conditions for operating the bioreactor with these yeast, one can use the system to optimize yeast production. Other experiments have shown that the nature of the nitrogen source may also be important.

Two experiments with garlic cells lead to a similar conclusion of 15 g/l per day of biomass produced. However, for the garlic cells, the prior nature of the treatment of the cultures played a critical role in the quality of the bioreactor results. A well defined suspension culture was necessary to achieve those results.

Other Factors

The FT-IR measures molar relationships between components since IR absorbance is related to the number of molecules of a specific type in the path. In our algorithms the results thus appear as mole fractions which are easily converted to mass fraction. From the viewpoint of engineering control, mass fraction or percent is exactly the correct way to present the information since it facilitates mass balances. For the purposes of clarity, however, we converted the data to more "normal" concentrations in g/l by measuring the density of the solution and using these values to perform the conversion. The solutions behave almost as pure sucrose solutions as may have been expected.

We indicated above that allowances could be made for glucose, ethanol, etc. Considering glucose the equations become:

$$\frac{dC_i^s}{dt} = -\frac{PA}{V_i}(C_i^s - C_o^s) - k_u^s C_i^s - k_I^i C_i^s \quad [8]$$

$$\frac{dC_o^s}{dt} = \frac{PA}{V_o}(C_i^s - C_o^s) - k_I^o C_o^s \quad [9]$$

$$\frac{dC_i^g}{dt} = \frac{PA}{V_o}(C_i^g - C_o^g) + k_I^i C_i^s - k_u^g C_i^g \quad [10]$$

$$\frac{dC_o^g}{dt} = \frac{PA}{V_i}(C_i^g - C_o^g) + k_I^o C_o^s \quad [11]$$

where the s denotes sucrose and g denotes glucose. The subscript u still refers to a constant for use of the material by the cells, whether glucose or sucrose. The subscript I refers to the rate constant for first order inversion of sucrose to glucose. Note that we cannot assume the inside and outside inversion rates are the same and so we have used the i superscript for inside and o for outside.

This model has been developed such that it gives engineering estimates of the membrane bioreactor based on a three parameters for each nutrient source. These parameters are:

1. Rate constants for utilization of the nutrient.
2. Corrections to the diffusion constant for flow through the membrane.
3. The efficiency of conversion of the nutrient to cell mass (or to metabolites in the case of biotransformations).

The model may be refined and used as the basis for a control algorithm. The major work lies in exploring the growth characteristics of individual cell lines to determine the most profitable systems for commercial exploitation.

DIFFUSION THROUGH A MEMBRANE RAFT

The first model for diffusion through a membrane raft is based on the solution of the diffusion equation subject to the boundary condition at one surface is a semipermeable membrane. To simplify the first considerations, we will not consider edge effects. It is not, in principle, difficult to add any degree of complexity to these models. The basic constraint is one of time and understandability of the model. For this reason, we will consider the simplest practical case first.

The membrane is assumed to be located in the plane x=0 with the liquid below. Diffusion across the membrane takes place according to Fick's Law in the form:

$$\frac{\delta C(0,t)}{\delta t} = -h(C(0,t) - C_0(t)) \quad [1]$$

where $C(0,t)$ is the concentration at the membrane for any time t at position x=0

$C_0(t)$ is the concentration outside the membrane which could also vary with time t is the time h is the ratio of the permeability of the membrane to the diffusion constant in solution of the species under consideration.

For general use, we will denote the permeability as P and the diffusion constant as D. In all the calculations, we will use the c-g-s system of units since this seems appropriate for containers of the size we are considering. In this system, P has units of cm/sec and D has units of $cm^2$/sec. In the first example, we will consider sucrose as the species, even though equation (1) is actually more complicated for sucrose. Sucrose inverts to glucose and fructose so there is an additional term in equation (1) for the boundary condition. Again, it is quite straightforward to add this later. Inside the liquid, below the membrane, the diffusion of material in the solution is given by:

$$\frac{\delta C(x,t)}{\delta t} = D\frac{\delta^2 C(x,t)}{\delta x^2} \quad [2]$$

To solve the equation, we will also assume that the liquid is very deep below the membrane raft. Again, this keeps things simple and allows the necessary complexity to be added as one understands the system. The distance is actually about 1.5 cm which, as we will see below, is sufficiently deep to not disturb the "deepness" assumption for the first 60 hours which is long enough to illustrate the point of the model. Our last assumption is that the sucrose is used by the cells as soon as it crosses the membrane. This would only be true for a rapidly growing culture, but that is the situation we are interested in exploring. This last assumption has the mathematical effect in equation (1) that $C_0(t)= 0$ for all times.

Subject to these additional conditions, the solution is:

$$C(x,t)=C_i[f_1(x,\tau)+e^{h(x+h\tau)}(1-f_2(x,\tau,h))] \quad [3]$$

where t is $Dt/A^2$, A is a unit area, in our case the area of the membrane and $$f_1(x,\tau) = \phi\left(\frac{x}{2\sqrt{\tau}}\right) \quad [4]$$

$$f_2(x,\tau,h) = \phi\left(h\sqrt{\tau} + \frac{x}{2\sqrt{\tau}}\right) \quad [5]$$

$$\phi(z) = \int_0^z e^{-y^2} dy \quad [6]$$

The function in equation (6) is the "error function" and has the property that it tends to 0 at z=0 and tends to 1 at large z. Methods of calculating this function are given in most numerical analysis references designed for use with computers.

For the cellulose acetate membrane of 12,000 molecular weight cut off, we found that the permeability was about 10 times the diffusion constant. The permeability and diffusion constant are related by a simple expression: permeability was about 10 times the diffusion constant. The permeability and diffusion constant are related by a simple expression:

$$P = \frac{DK}{\Delta X} \quad [7]$$

Where Dx is the thickness of the membrane and K is determined experimentally as a factor which slows down (or in rare cases speeds up) diffusion. In our laboratory, we determine P from an analog of equation (1) where the medium is stirred on both sides of the membrane:

$$\frac{dC}{dt} = -\frac{PA}{V}(C - C_0) \quad [8]$$

where C is greater than $C_0$ and they represent the concentrations on either side of the membrane. A is the membrane area and V is the volume on the side which contains the concentration C. If one used the volume on the other side, then the sign on the right hand side of equation (8) would be positive (appearance of material) rather than negative.

We use the FT-IR spectrometer and a control program to analyze for the simultaneous diffusion of many species. If the microporous polypropylene was the same as cellulose acetate, calculations based on the equations above would give the results shown in FIGS. 15 through 18.

Figure 15:
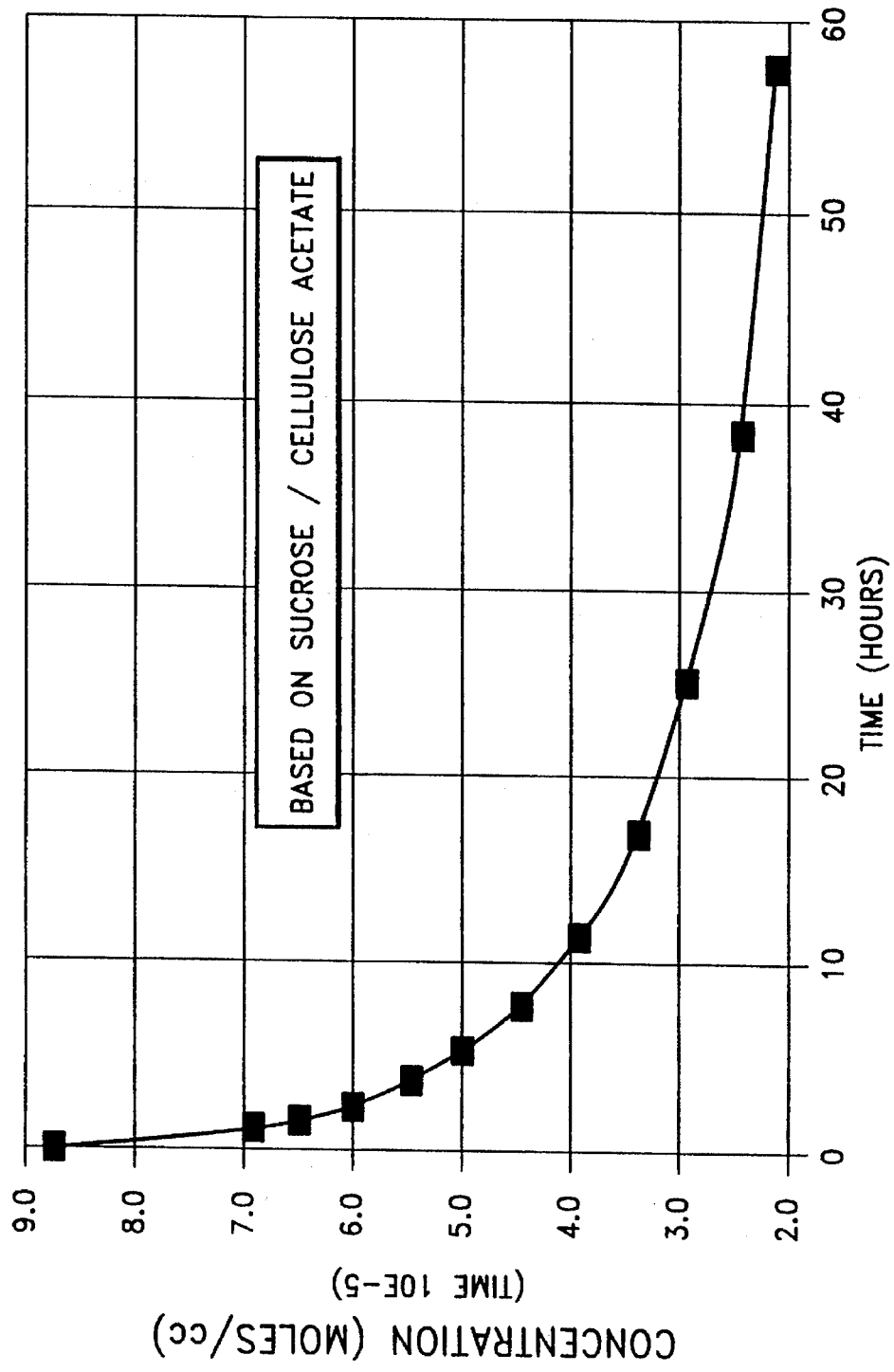
FIGS. 15 through 18 shows sucrose concentration immediately below a raft membrane container at four different depths.
Figure 16:
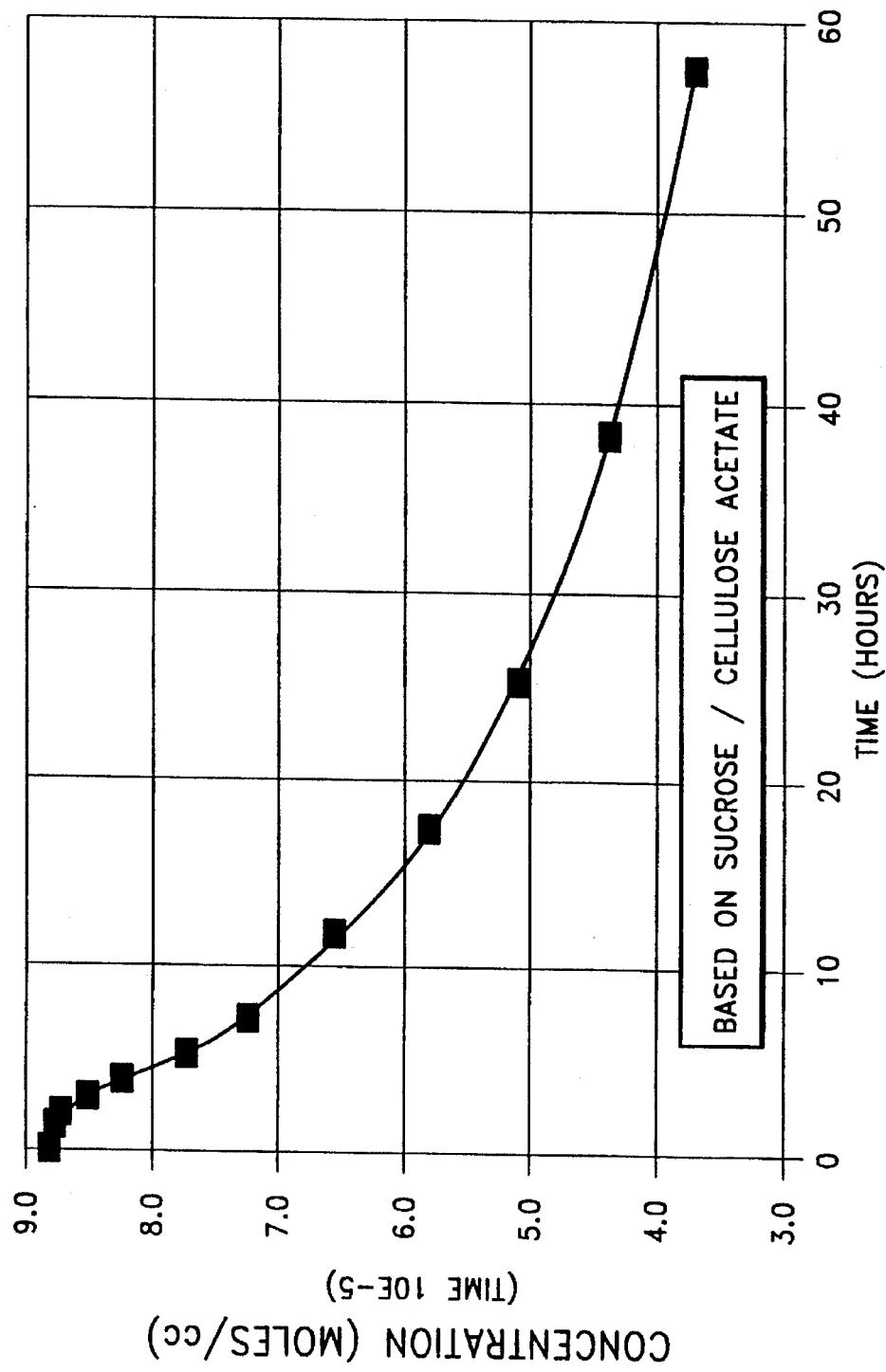
Figure 17:
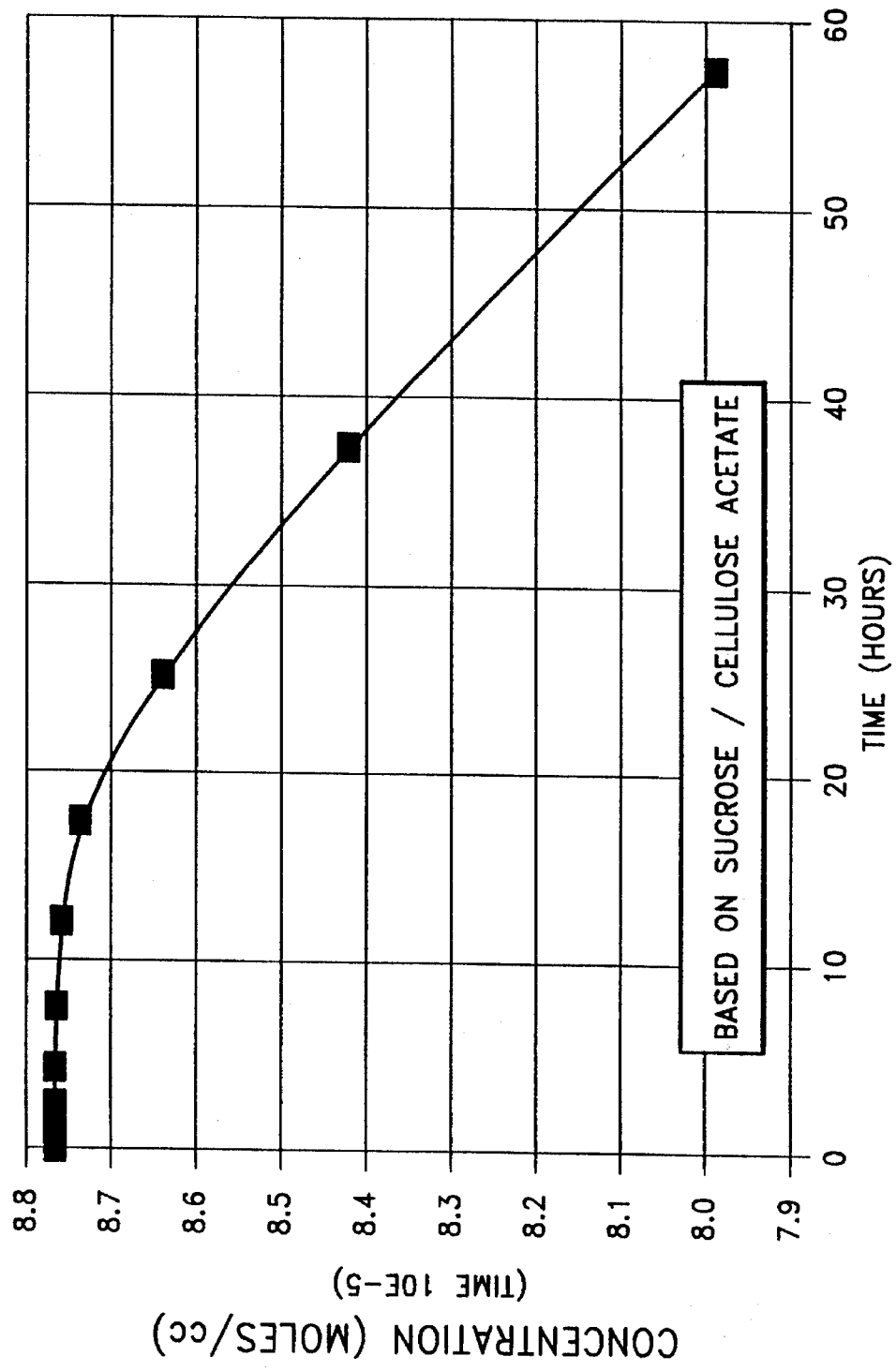
Figure 18:
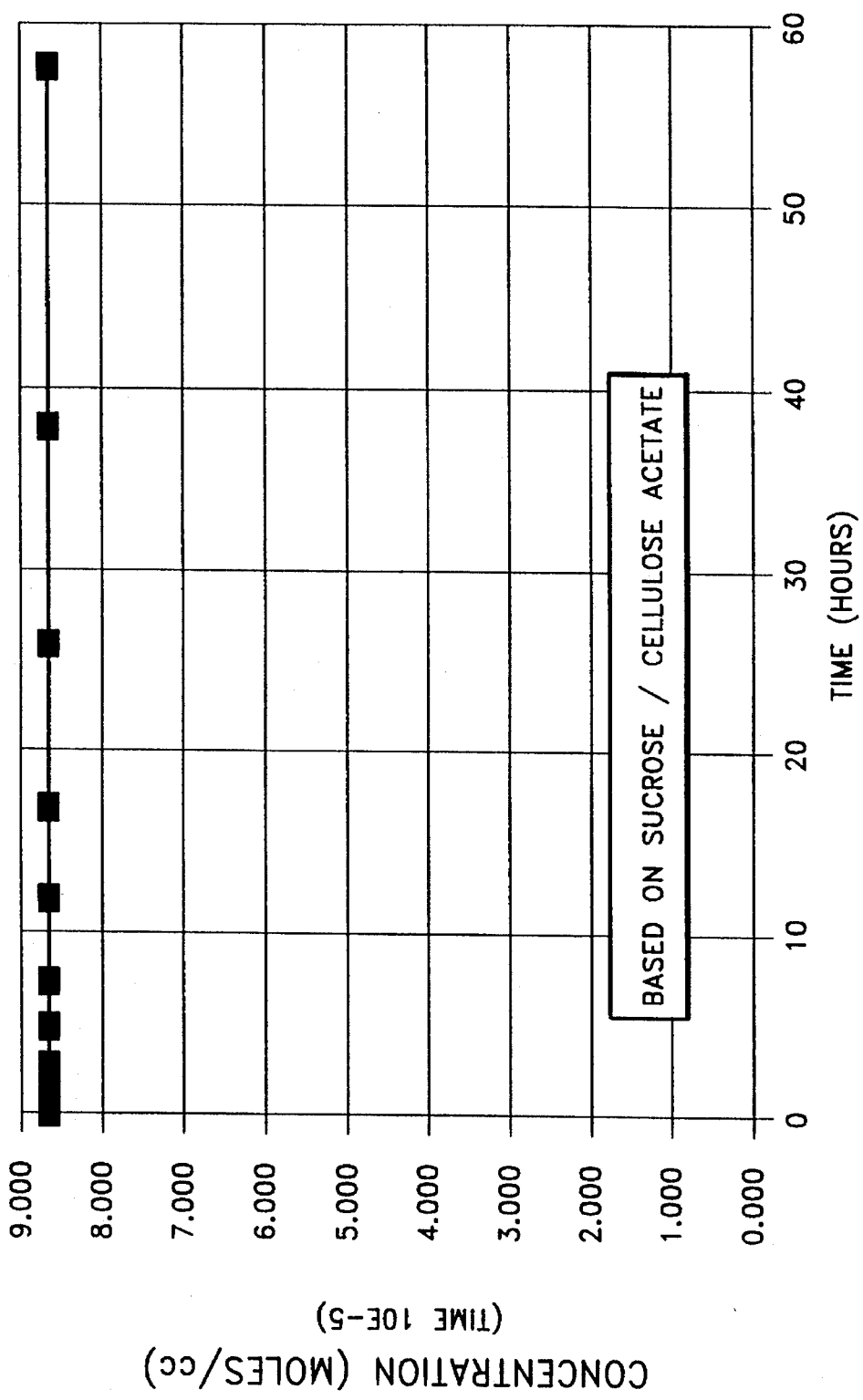
Figure 1:
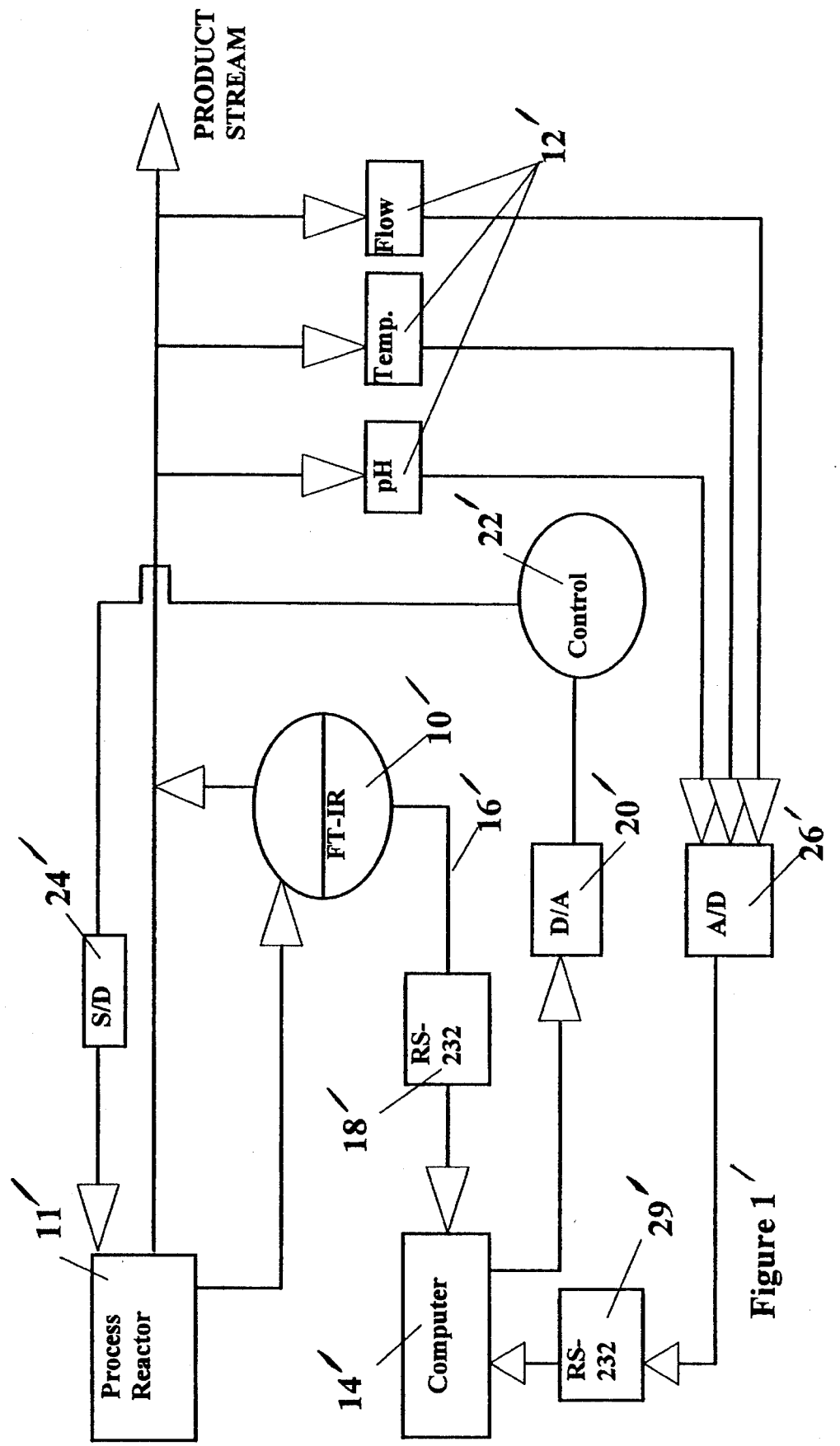

The FIGS. 15 shows the depletion of sucrose immediately below the raft. We used a sucrose concentration of 3% which is common in many media. The rate at which sucrose crosses the membrane is proportional to the concentration across the membrane [e.g., equation (1)]. We see that in less than two hours, the rate at which it crosses has been reduced by two. Meanwhile, further down in the solution respectively below the raft at depths of 0.1, 0.5, and 1.0 centimeter, as depicted in FIGS. 16 through 18, the solution is being depleted less as one would intuitively expect. It should be recalled that there are not many cell lines that would use the sucrose this fast and the actual results would be different for each value of $C_0$ I used in equation (1). To use other values and have them be a function of time (a real case) would simply make the answer more complicated to write down and, it may be equally advantageous to use numerical techniques to make the solution general. The big advantage of an analytical solution such as this one is that you can use it to check more complicated numerical models later.

One interesting conclusion is that if one does not stir the bottom to keep the concentration high below the raft, one can eventually impede the growth of cell mass. The local concentration below the raft drops more quickly than the bulk of the solution slowing down transport. In agar, most often used for cell growth, there is no membrane to slow things down, but the diffusion constant is smaller so we end up at about the same place. The advantage over agar would be improved by gentle shaking.

There are several things that can be done to utilize this model for more complex cases:

1. Some of the simplifying assumptions can be removed.
2. Species specific data on permeability for individual membrane types could be used.
3. A general algorithm that was only constrained by geometry could be developed for use on computers.

Modified Chi-Square Technique

The modified Chi-Square technique is used in the determination of the actual concentrations of the chemical species in solution is best explained with reference to a concrete example such as analysis of a mixture of sucrose, glucose, and ethanol in water. The method steps are:

1. Make up a series (5) of individual calibration solutions or samples of each of the components at a known concentration in water, spanning the concentration range of interest, for example, 1–10 weight percent. Take the spectra of these calibration samples over a selected range of interest, for example 600 cm$^{-1}$ to 4400 cm$^{-1}$, and determine k's for each sample at each concentration and at each wavenumber from:

$$A = k_{water} c_{water} + k_{sample} c \qquad [7]$$

and $$c_{water} + c = 1.0 \quad [8]$$

Equation [8] is true because the concentrations are in mole fractions which must add up to 1.0. The $k_{water}$ is simply the absorbance of the background water. This is obtained by taking a spectra of pure water alone in the same cell. The range for the spectra can be in any portion of the spectra in which one expects to find significant information. In this case, based on general knowledge of the spectra of the components, the range of 600 cm$^{-1}$ to 4400 cm$^{-1}$ was chosen. This means that one has a file of k's for each of the compounds, sucrose, glucose, and ethanol for each wavenumber. This process is repeated 5–20 times, optimally 10, such that one can obtain statistically significant values of the k's at each concentration.

2. Use the same spectra from 1 to obtain a standard deviation file. For example, the 10 spectra of sucrose (without modification) are averaged and the standard deviation is obtained at each wavenumber. The standard deviation of the set of three (glucose, sucrose, ethanol) are then averaged (or summed) to obtain the standard deviation file to be used for the Singular Value Decomposition (SVD) fit of the data in step 3 below. Generally the average is preferred. However, the sum would give the most conservative estimate of the goodness of fit, which is also available from the covariance matrix in the SVD technique.

3. Make up one mixture of known composition and use this as a "mock unknown" or calibration sample mixture. Measure its spectrum and then analyze it according to [6] and the SVD technique over a range of wavenumbers covering all significant features of the absorbance spectra of the previous separate knowns used in 1 and 2. For example, the range 800 cm$^{-1}$ to 1500 cm$^{-1}$ could be a good wide starting choice. The SVD technique provides a statistical measure of the goodness of fit in two ways. First, it provides the Chi-Square statistic and second, it provides a standard deviation for each determined quantity. In this case, we are determining the mole fractions of water, sucrose, glucose, and ethanol, so each of these would have a standard deviation associated with it which are compared to the actual values. The range of wavenumbers used is reduced and/or moved in the spectrum to find the range of wavenumbers that provide the lowest Chi-Square statistic and lowest standard deviations. In the example, this could be the range 994 cm$^{-1}$ to 1100 cm$^{-1}$. The exact range will differ from instrument to instrument and cell to cell, but the technique will find the best range for the particular combination one has available. The computer can be programmed to move the range randomly or systematically. The method will always find the best range of those examined based on the Chi-square value and standard deviations. The range can be varied until a desired degree of precision is achieved.

4. One can now measure true unknowns. The measurement is made normally and the first analysis is made using the k's determined form knowns from step 1 that are close to the anticipated concentrations. The standard deviations are also used from the same files that provide the k's. When the answers are obtained from the SVD technique, they are examined to see if there is a set of k's determined from any of the non-solvent unknowns (sucrose, glucose, ethanol) at a concentration closer to the answer just found than were those used in determining the answer. If a set of k's from a closer concentration is available, it is used and the concentrations recalculated. This procedure is repeated until the closest k's are used. It is preferred to refine this procedure by interpolating between k's such that the final answer is as close to the concentration corresponding to the k's as one would like it to be, e.g., within 1% or so. For mixtures of gases, equations [7] and [8] are replaced by the simpler expression of equation [2].

Use of the Modified Chi-Square Technique

The modified Chi-Square technique of this invention is ideal for on-line monitoring and control of a chemical process. Any suitable computer using, for example, an 80826 microprocessor and equipped with analog to digital (A/D) and digital to analog (D/A) interfaces, may be use to implement this modified Chi-Square technique. The computer is attached to both the D/A and A/D boards via a parallel port (D/A) and a serial port (A/D). A second serial port is attached to the FT-IR instrument.

A chemical stream from the process of interest is constantly flowed through the cell in the FT-IR instrument. For example, this could be the exhaust of a combustion device, the broth in a fermenter, water being discharged from a factory, a chemical process, etc. The same process is also monitored with various probes to measure temperature, pressure, flow, pH, dissolved oxygen, humidity, density, weight, etc.

The probes monitoring the physical parameters of the process are connected to the A/D board, which has an on board microprocessor to act as storage and shipping center of the information to the host 80826 microprocessor. The host computer need not use an 80826 microprocessor and, in fact, all of the hardware and software is designed to be portable to any computer environment. The A/D board collects the probe information until it is polled by the host computer. The FT-IR instrument is also commanded by the host computer. In this manner, the host computer can regulate the flow of both chemical and physical input information and create files and displays of all of these parameters as a function of time.

The host computer also contains outputs through the D/A board connected to the parallel port that allows the chemical and physical information to be used to control switches and valves of the control instrumentation for the process. The process of this invention performs the integrated tasks of monitoring and control based on measurements of chemical concentrations as well as physical criteria. Until now, processes that use chemical composition criteria have been limited to those which use electrodes (which are relatively inaccurate and require frequent replacement) or to those which use mass spectrometry or combination gas chromatography and mass spectrometry. These later cases are slower in response and more costly and frequently require either removal or pretreatment of the sample. Using FT-IR instruments, the sample essentially never leaves the system being monitored, the sample requires no pretreatment, and the answers are as rapid as the scans. Including analysis processing, the answer is available in seconds compared to minutes or hours for the other instrument techniques and much more accurately and for a much wider range of chemicals when compared to the very limited electrode technique.

FIG. 1' illustrates a typical biochemical process such as those discussed above wherein sucrose is added periodically to sustain the growth of living plant cells in a reactor 11'. The sucrose inverts to glucose and fructose and some is consumed by the cells which are undergoing transformation in the process. To maximize the yield of the desired product of the process, in this case cell mass and metabolic byproducts, the temperature, pressure and pH of the reaction must be carefully regulated based on the concentration of the sucrose, glucose, and fructose.

A conventional FT-IR instrument 10' (Perkin Elmer Model 1640) is used to obtain absorption spectra on a sample stream from the process. Samples are passed through the transmission cell (not shown) of the FT-IR instrument continuously, with readings taken every 5 to 10 minutes over a period of 72 hours. More frequent readings may be made as required in order to optimize the physical parameters of the process. Conventional monitoring probes 12' are used to monitor the physical parameters of the process and a conventional general purpose computer 14 stores data and provides control functions as required based on the concentration of the reaction ingredients. An output 16' from the FT-IR instrument is connected through an RS-232 port 18 to memory of the computer 14' and the data collected by the FT-IR instrument 10 is stored in the computer's memory. According to the method of this invention, data files are created which enable the computer 14', based on measurements being made as the process proceeds, to analyze the data and determine the concentration of reactants accurately and rapidly. Based on this determination, the process parameters are adjusted to optimize the process. As discussed above, a digital to analog converter (D/A) 20' is coupled between the computer and a controller 22' which opens and closes a shut off valve 24' for the process. If the sucrose, fructose, and glucose drop below predetermined ranges, more sucrose is added to the system. If they remain high, either pH or temperature is adjusted to increase the rate of cell growth. If unwanted new chemicals are observed as measured by a sudden increase in Chi-square value, the operator is warned. If either the concentrations or physical parameters fall outside dangerous limits for cell viability, the system can be automatically shut down. Temperature, pressure, pH, flow rate are monitored by the conventional sensors or probes 12' and the electronic output measurements are feed to an analog to a digital A/D converter 26' connected between the computer 14 and these probes as discussed above. The output of the A/D converter 26' is connected through an RS-232 port 29'. Thus, both the concentration of reactants, and if desired the concentration of the reaction products, are monitored in real time along with the physical parameters of the process to control the process to optimize it. Hitherto this has never been achieved. Consequently, conditions may now be controlled precisely to optimize the process. This has been achieved using this invention for a wide variety of plant and yeast cells.

CREATION OF DATA FILES

In accordance with this invention, calibration samples are prepared before starting the process and data files are created and stored in the memory of the computer 14'. The first step of the method of this invention is to prepare a number of calibration samples spanning the concentration range of interest. Ten samples at each concentration were thus prepared. Calibration samples of aqueous solutions of 0.5, 1.0, 3, 5, and 7.0 weight percent sucrose, 0.5, 1, 2, and 4 weight percent glucose, and 0.25, 1, 2, and 4 weight percent fructose were initially prepared and spectra obtained.

The electromagnetic absorption of these calibration samples at a selected number of wavelengths (wavenumbers) over a predetermined range were measured to obtain a spectra for each sample, k values and standard deviations thereof were calculated at each wavenumber, and data files consisting of these values were created and stored in the memory of the computer.

Using following equation:

$$k = \frac{A - k_{solvent}(1.0 - c)}{c} \quad [10]$$

(for solvent system—liquids or solids)

A is the absorbance measurement of each individual calibration sample, and c is the concentration in molar units of the ingredient in the calibration sample, $k_{solvent}$ is the absorbance value for pure solvent, for example, water, an average k value for each calibration sample is calculated at each of the selected number of different wavelengths over the predetermined range of wavelengths selected. The standard deviation value S of k values were determined according to the following formula.

$$S = \left[ \frac{1}{m-1} \sum_{i=1}^{m} (k_i - k)^2 \right]^{1/2}$$

where $k_i$ are the m individual values at each wavenumber, k is the average k at each wavenumber, and m is the number of replicates performed at each wavenumber (10 for example).

Figure 2A:
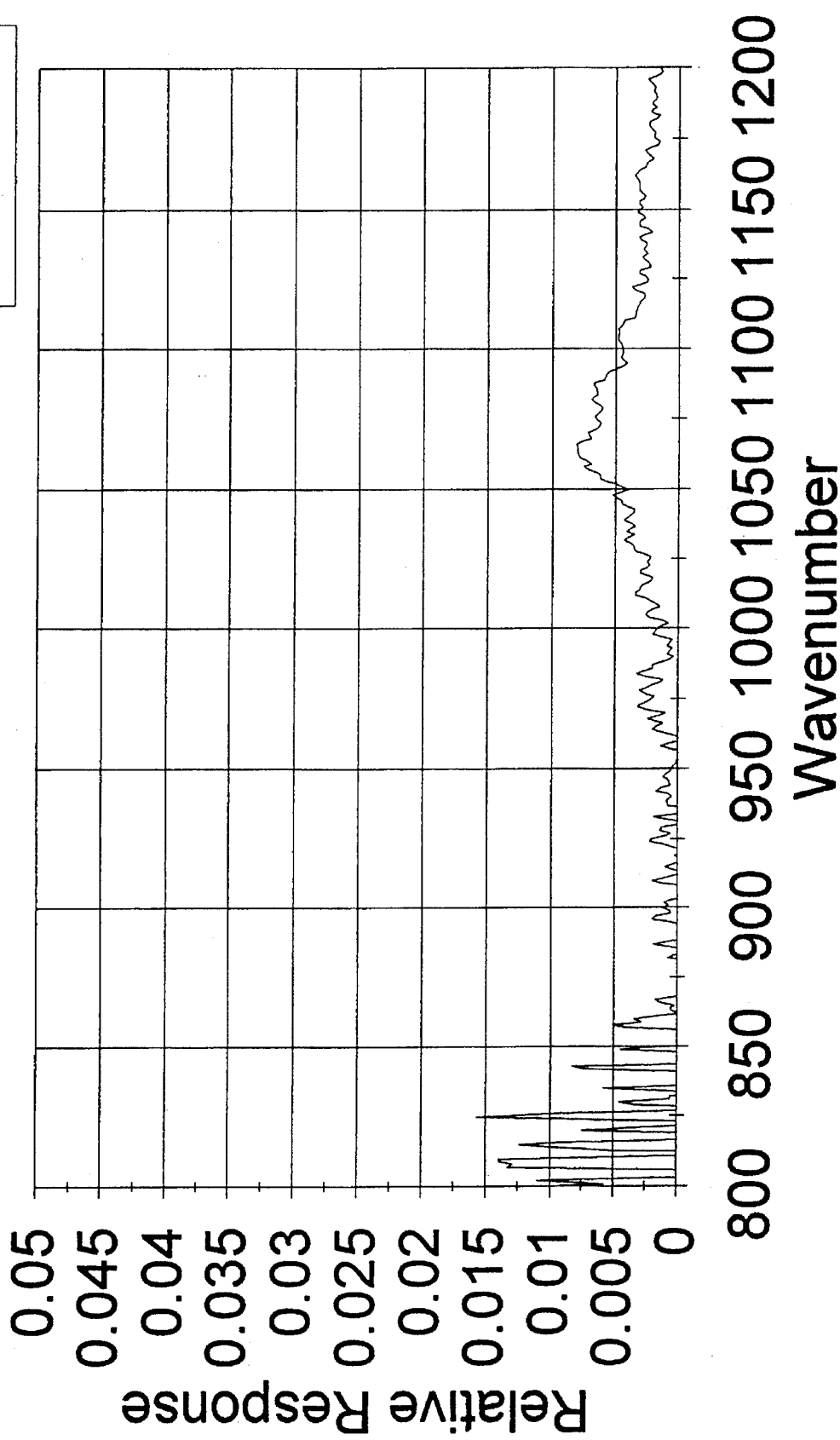
FIGS. 2A' through 2E' is the absorption spectra for a 0.25 weight percent aqueous fructose solution taken over a range of wavenumbers between 800 and 2800.
Figure 2B:
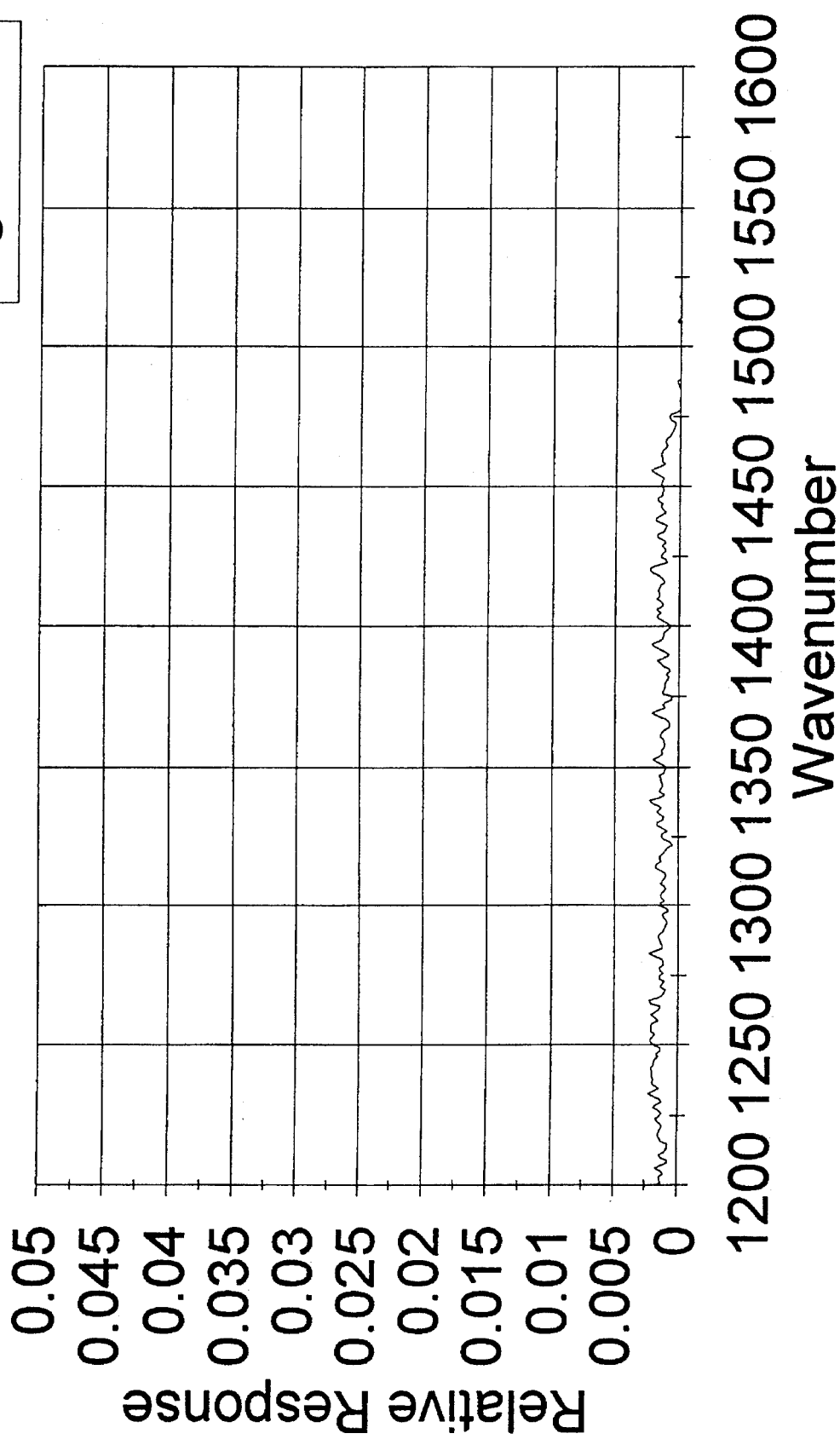
Figure 2C:
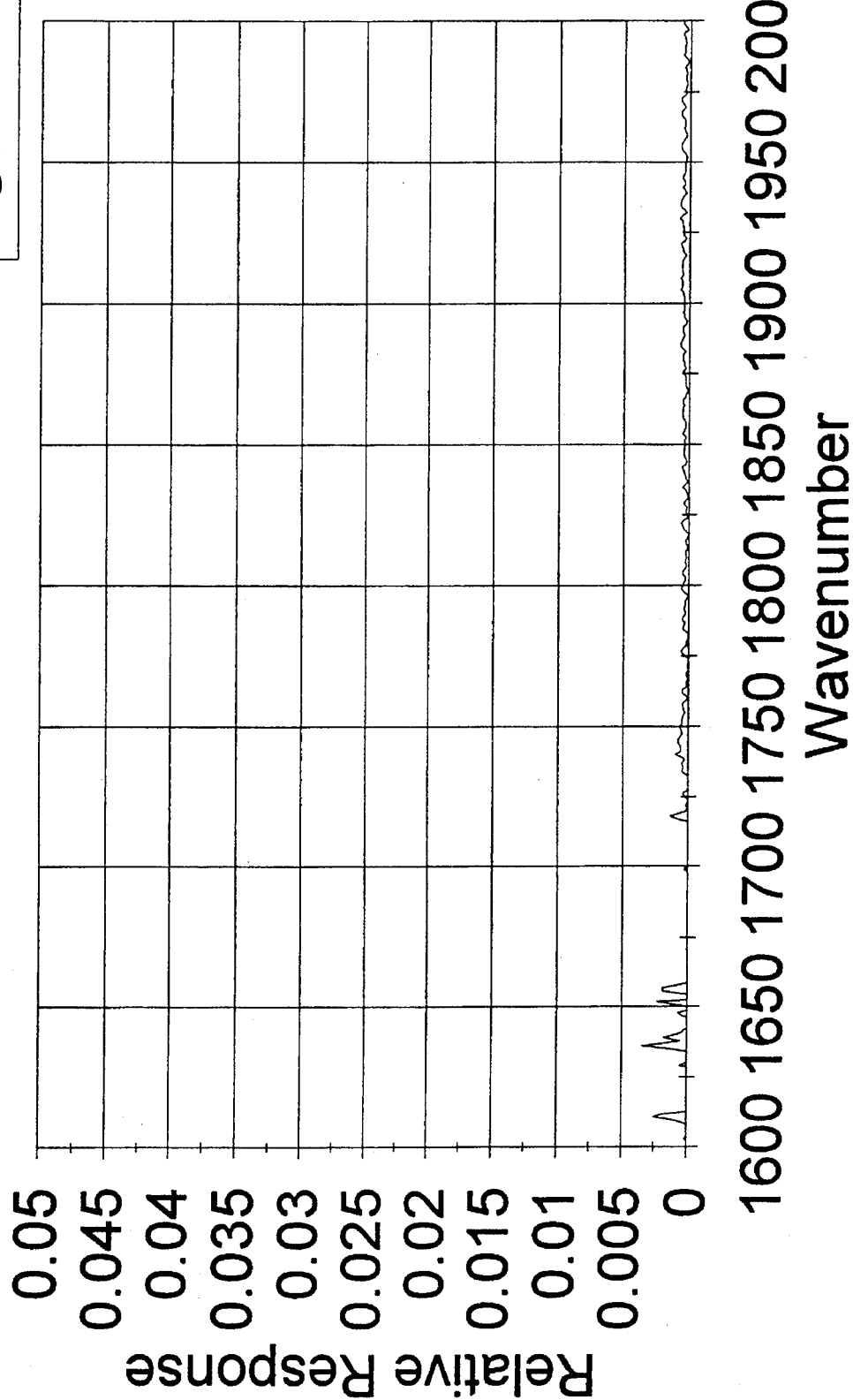
Figure 2D:
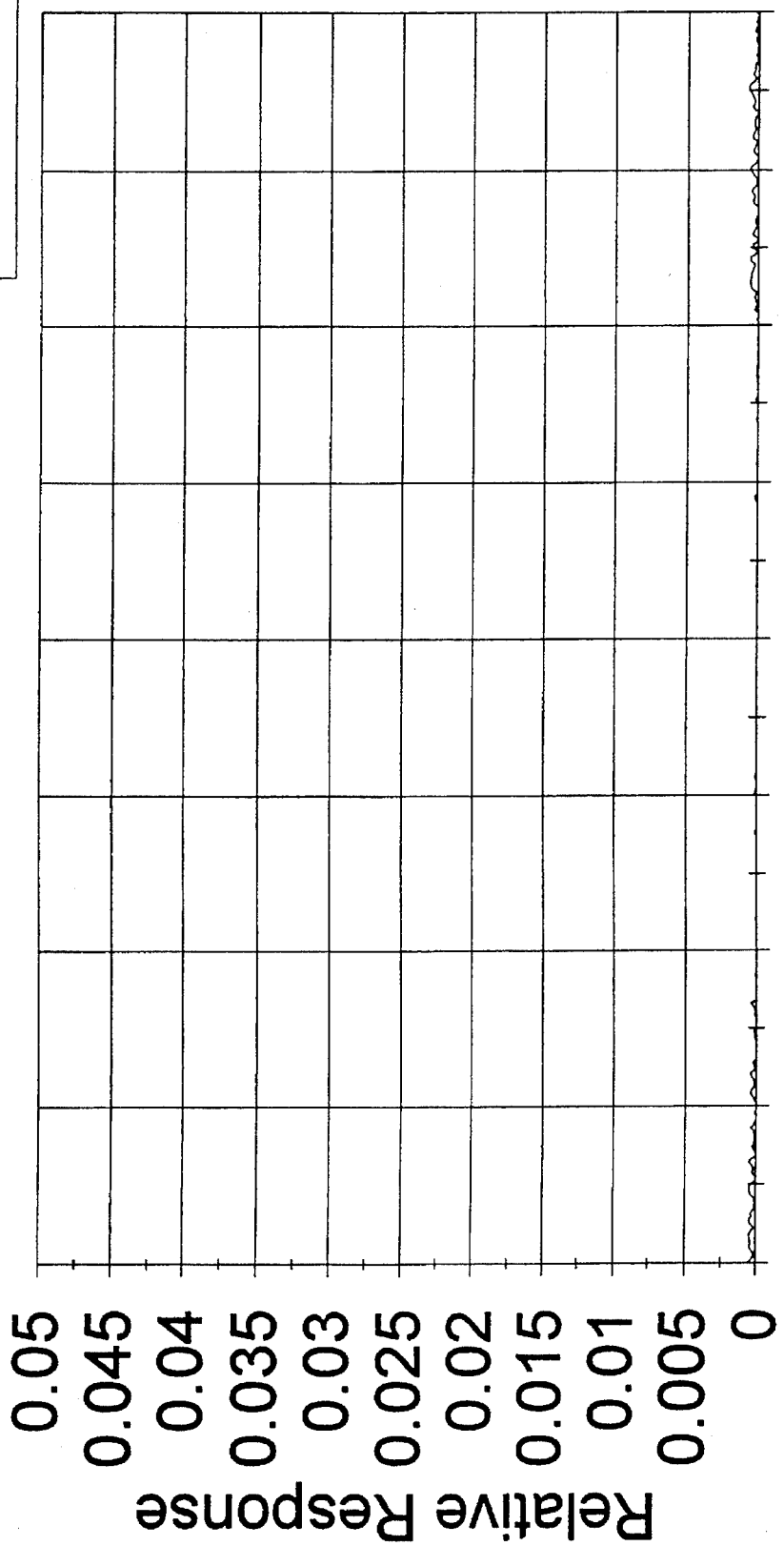
Figure 2E:
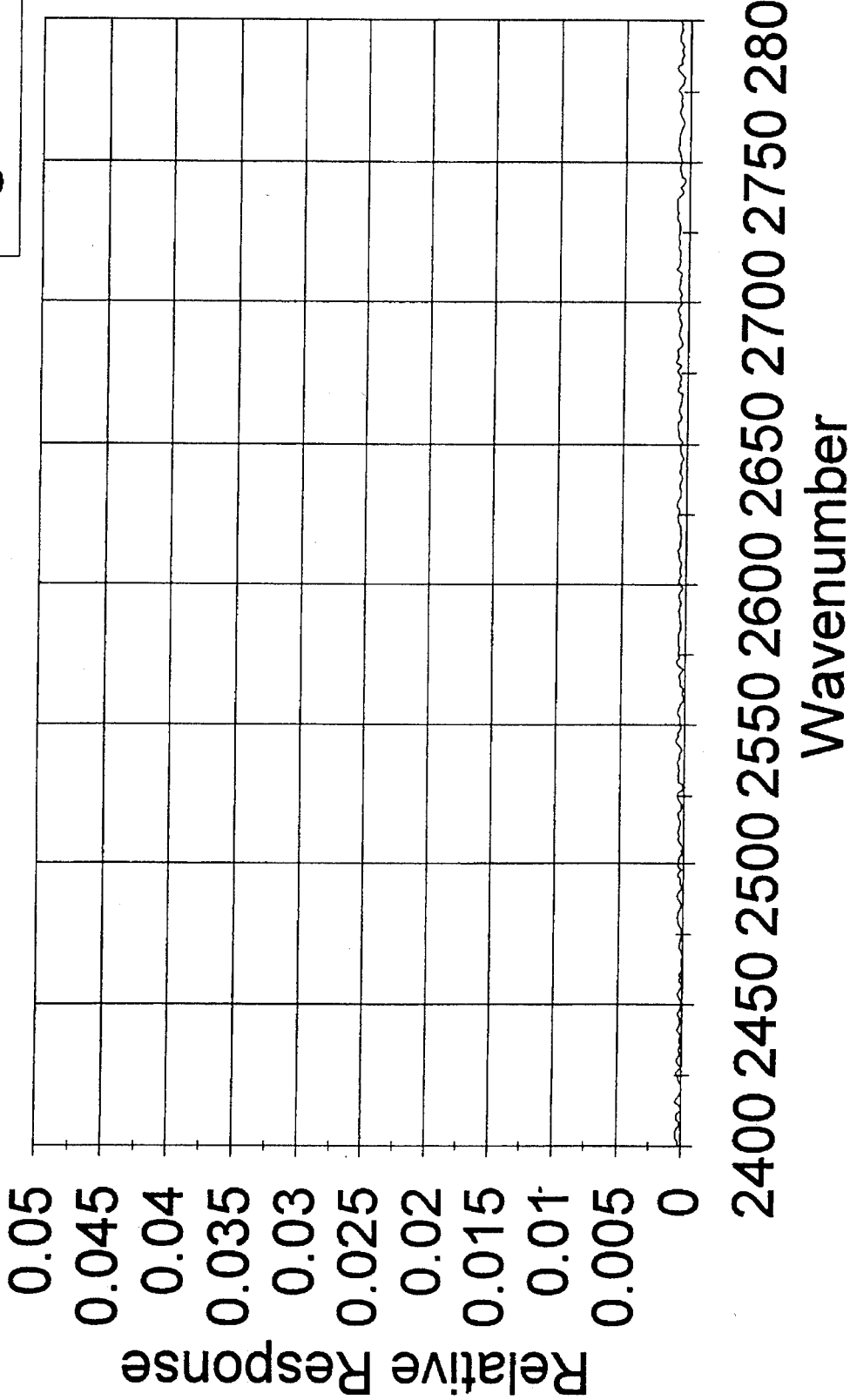
Figure 3B:
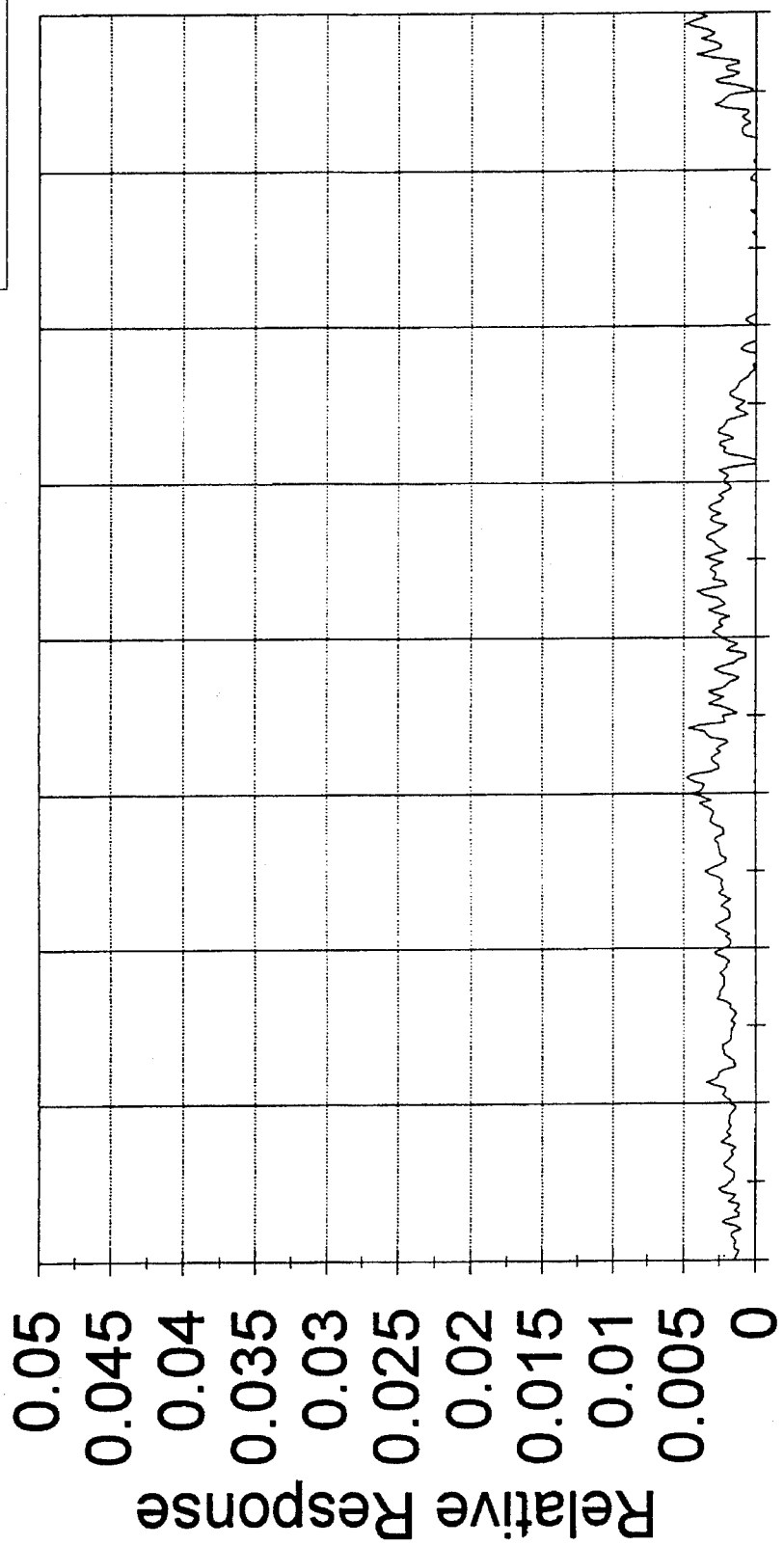
FIGS. 3A' through 3G' is the absorption spectra for a 0.50 weight percent aqueous glucose solution taken over a range of wavenumbers between 800 and 4400.
Figure 3C:
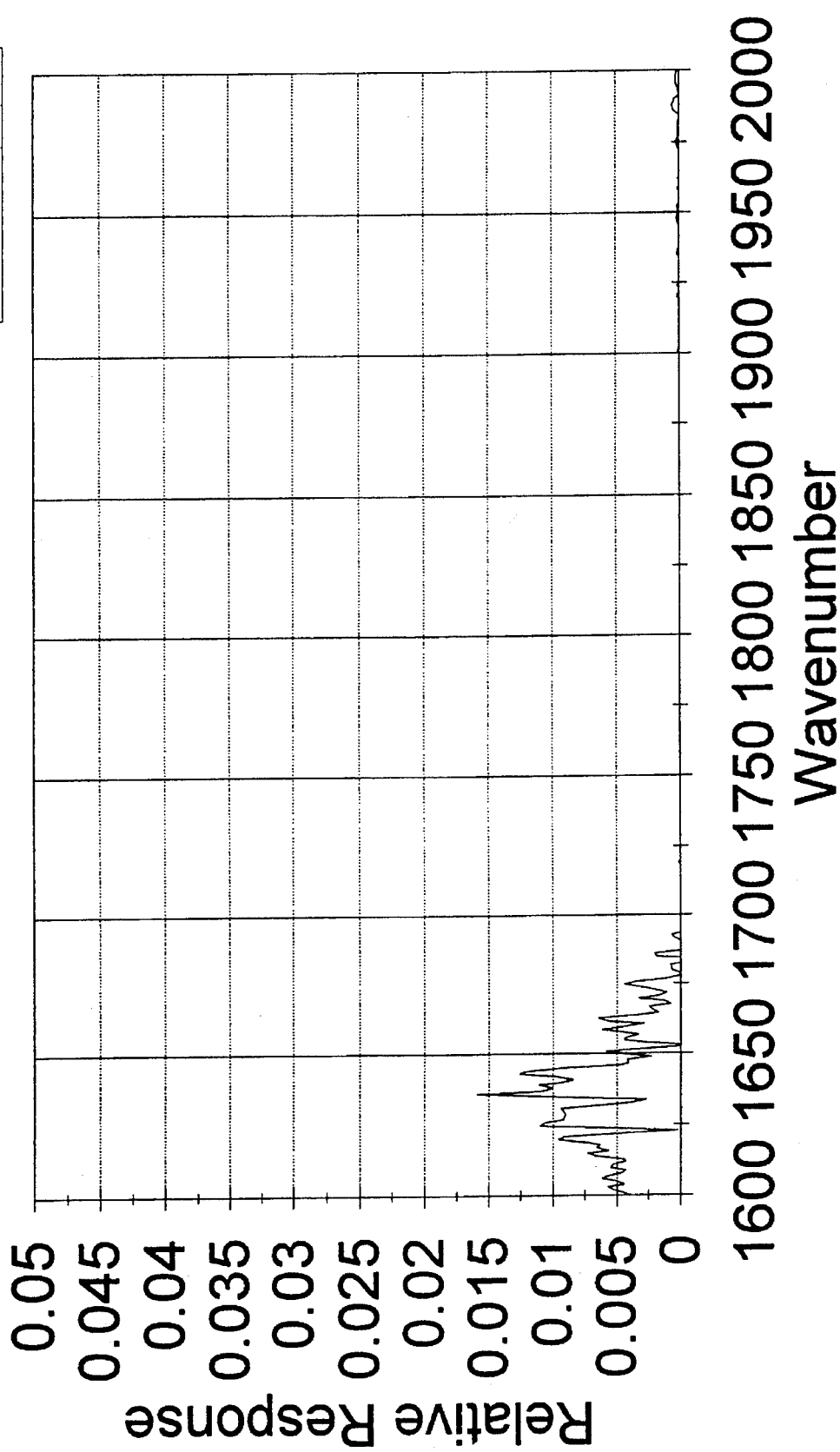
Figure 3E:
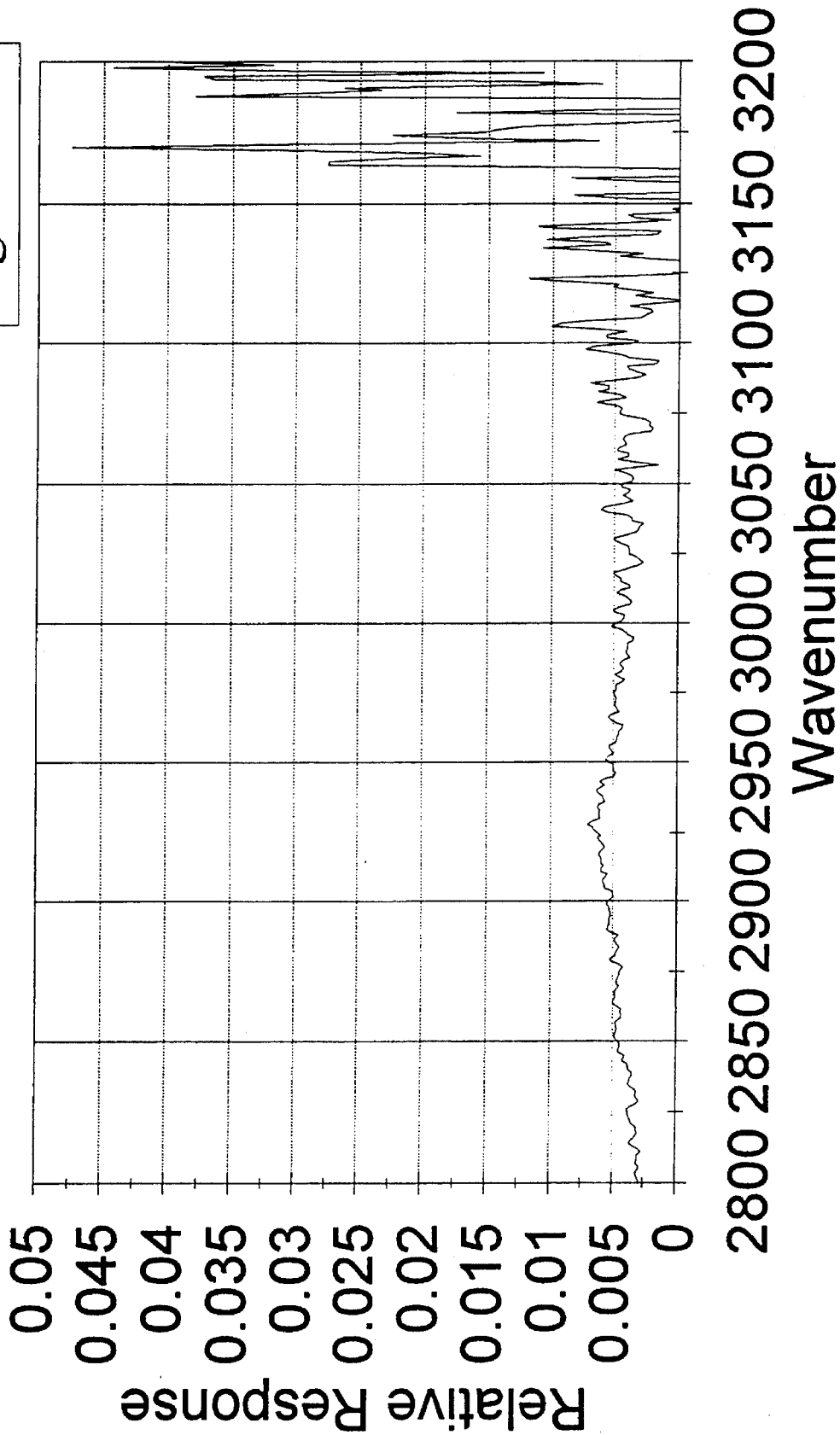
Figure 3G:
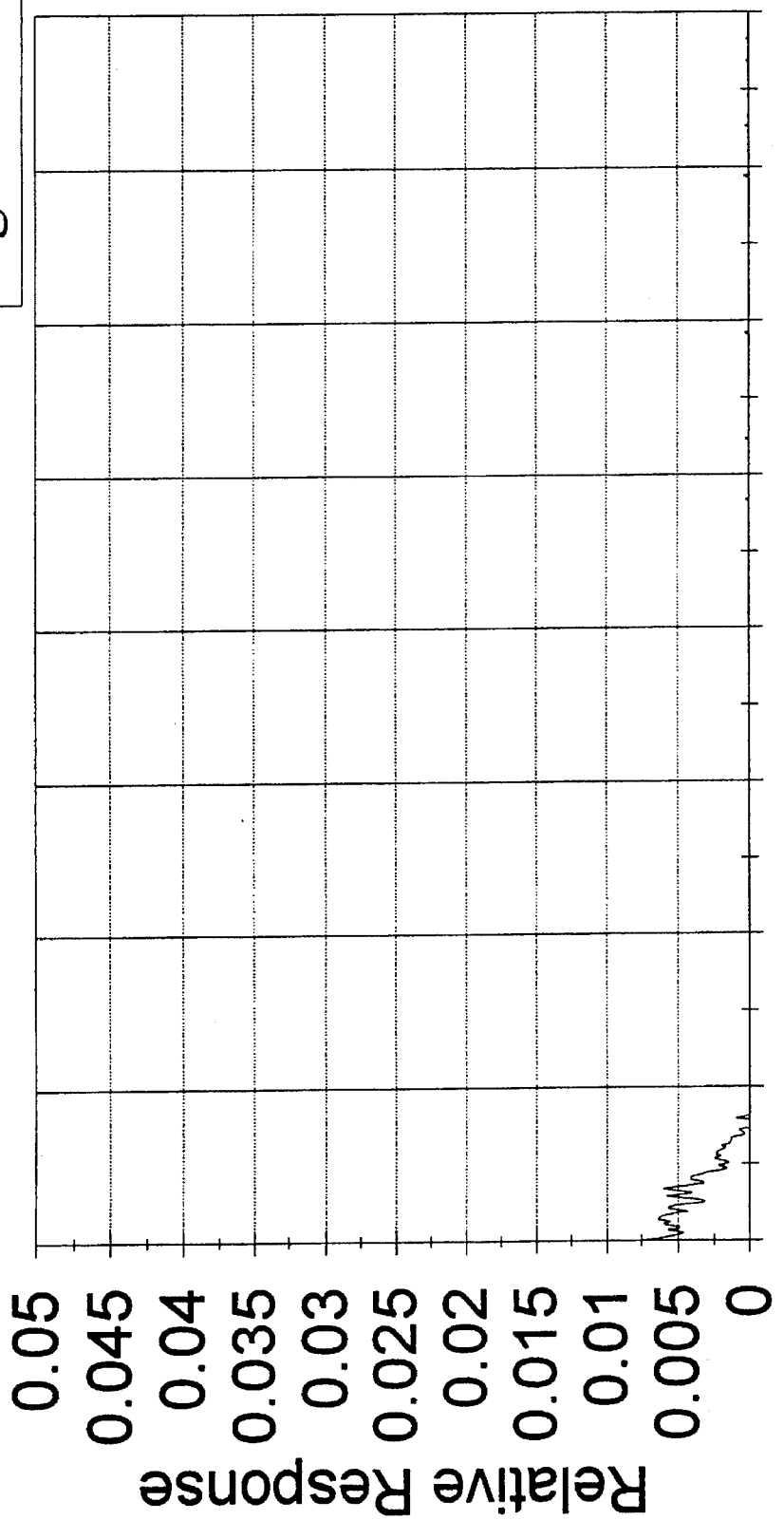
Figure 4B:
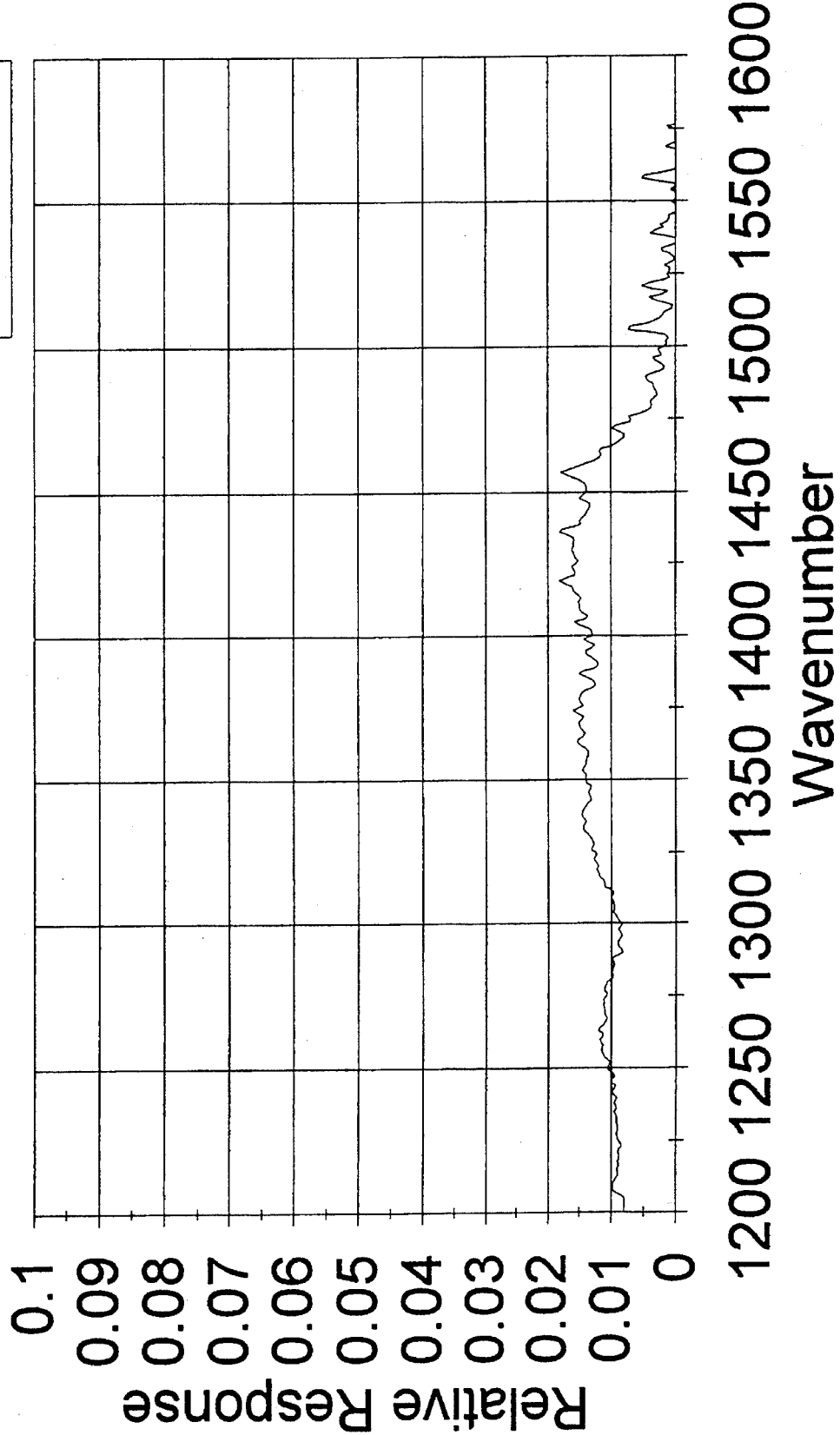
FIGS. 4A' through 4H' is the absorption spectra for a 3.0 weight percent aqueous sucrose solution taken over a range of wavenumbers between 800 and 4400.
Figure 4C:
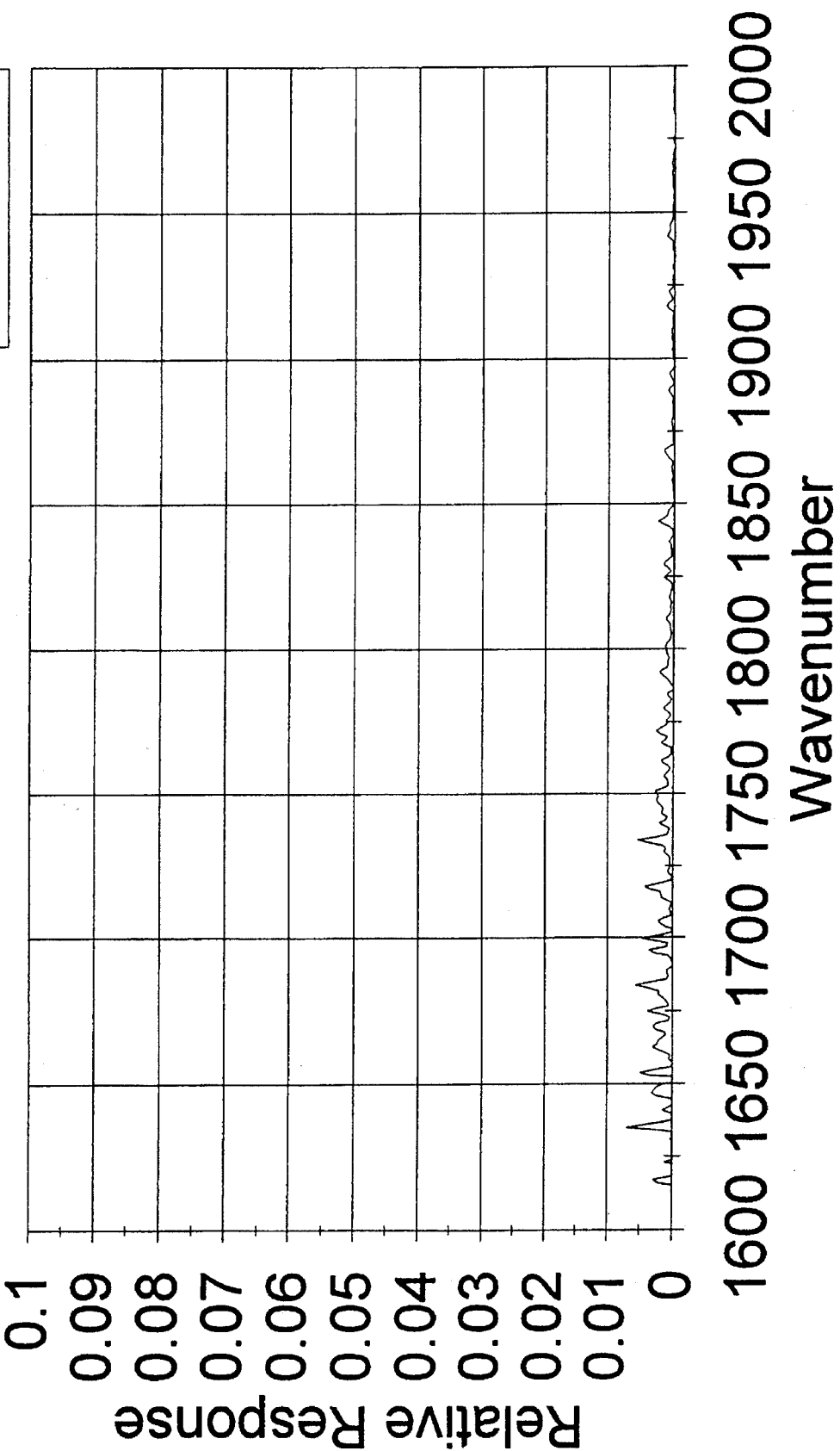
Figure 4D:
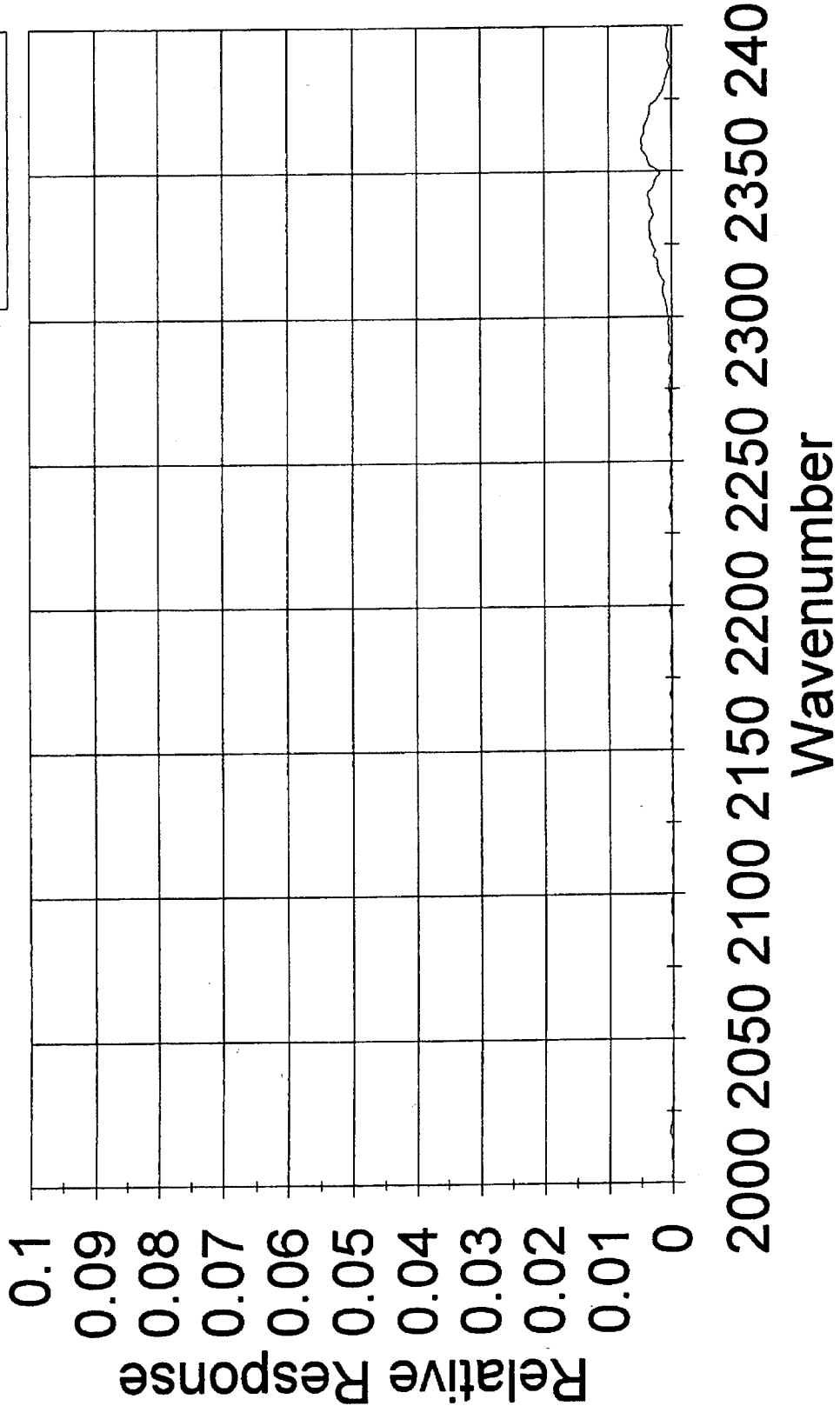
Figure 4E:
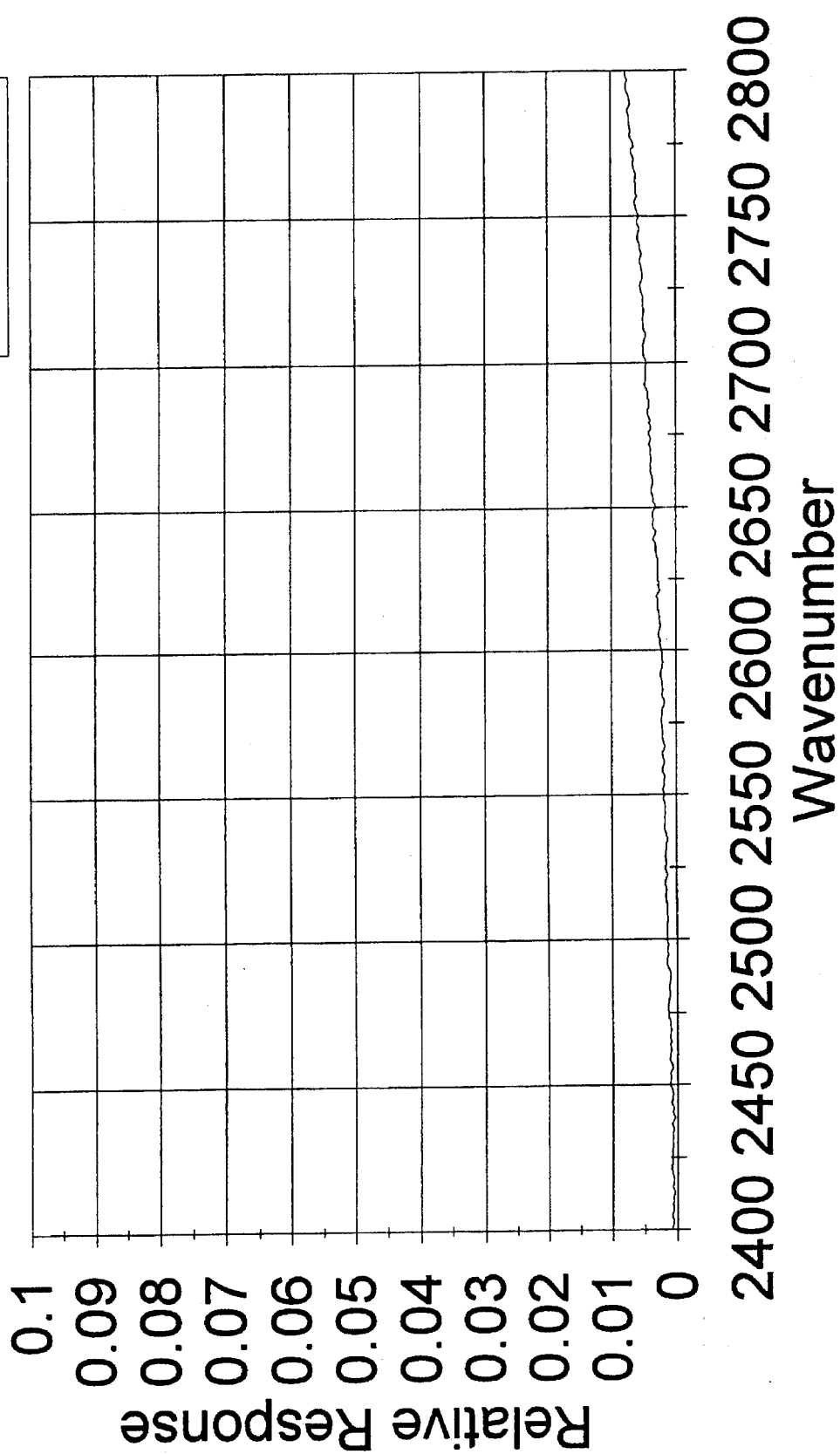
Figure 4G:
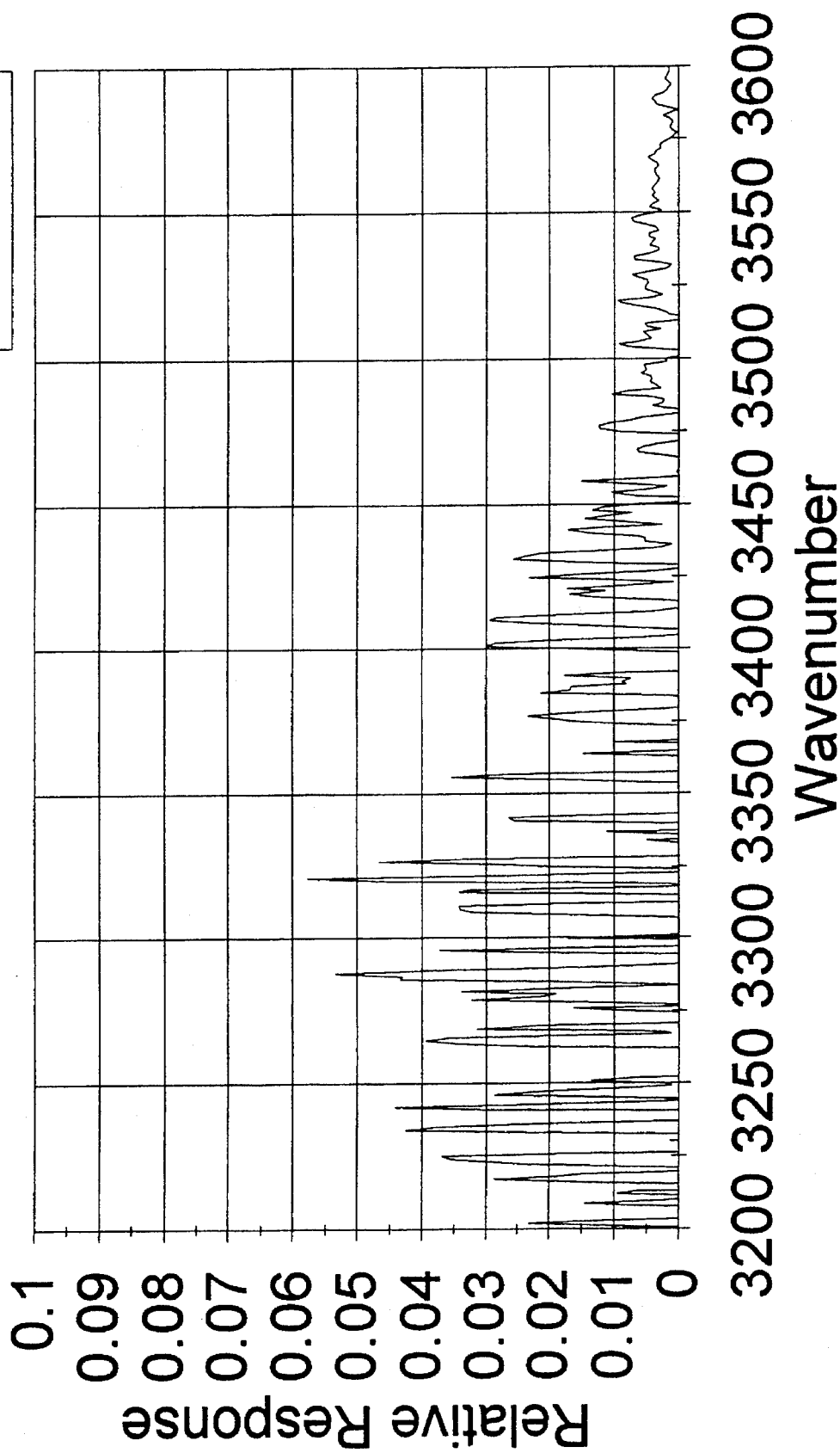
Figure 4H:
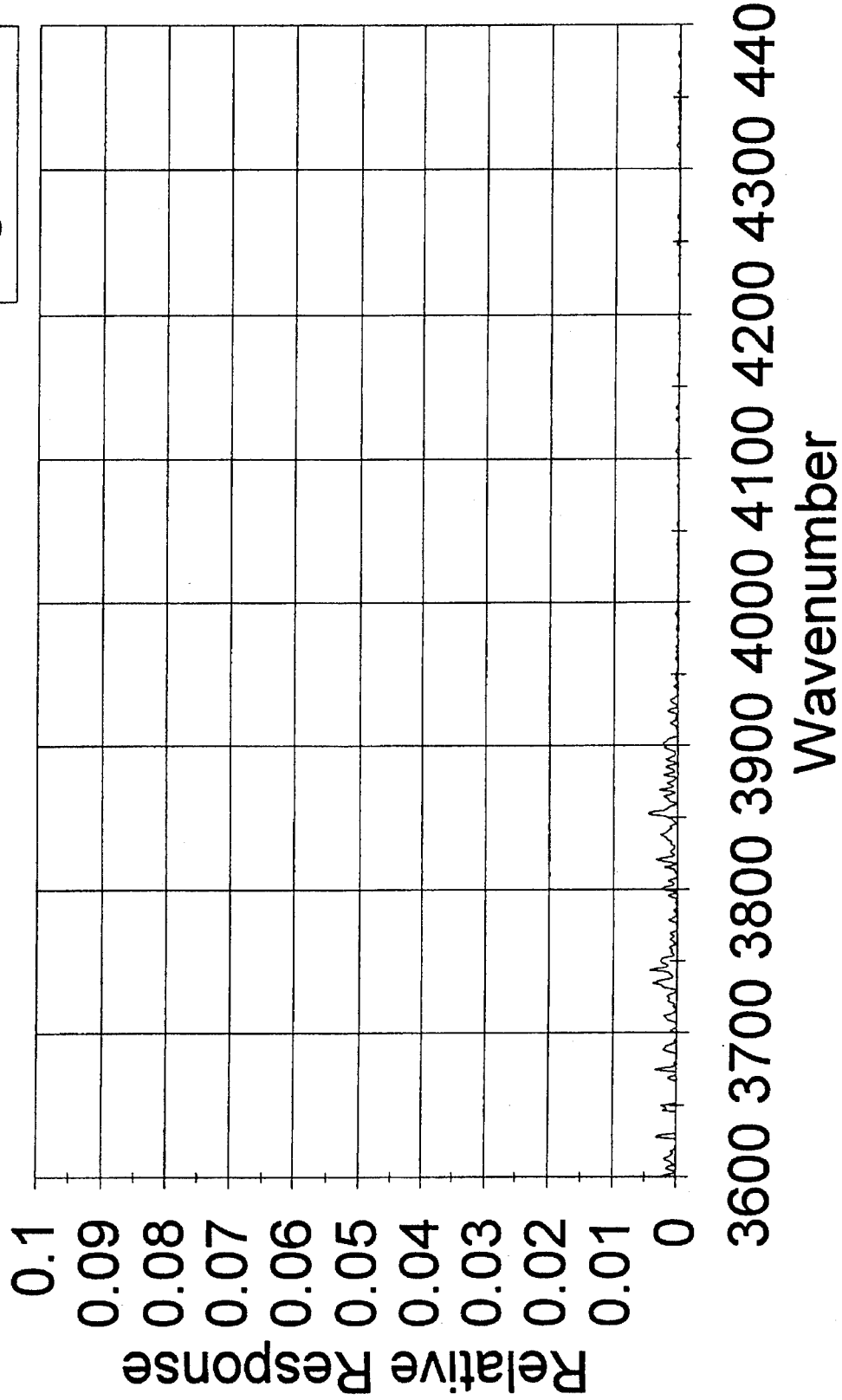

FIGS. 3A'–3G' is the spectra of the 0.5 weight % glucose-water solution and Table I (Exhibit A) is illustrative of the date file for this solution. FIGS. 2A'–2E' is the spectra of the 0.25 weight % frutose-water solution and Table II (Exhibit B) is illustrative of the date file for this solution. FIGS. 4A'–4H' is the spectra of the 3.0% sucrose-water solution and Table III (Exhibit C) is illustrative of the data file for this solution.

In Tables I, II and III, the column designated # presents the wavenumber; the columns designated A through J presents the k values for the ten replicated calibration samples at each wavenumber in the column designated #; the column designated AVG presents the average of the ten k values at each wavenumber; and the column designated STD presents the standard deviation of the average of the ten k values at each wavenumber. Because ten replicated calibration samples were taken for each calibration sample, statistically significant results are obtained. For greater accuracy a greater number of replicas are required. For most purposes twenty replicas are sufficient. The data in the Tables I, II and III is stored as data files in the memory of the computer 14.

After data files for individual reactants have been created, data files for the mixture of reactants is created: First, a sample mixture of the reactants at known concentrations is prepared and then the electromagnetic absorption of the sample mixture is measured at each of a selected number of different wavelengths over a range of wavelengths of the electromagnetic spectrum anticipated to be best representative of the absorption characteristics of the sample mixture based on collected data from the individual components.

Second, it is determined which wavelengths within the range (scan range) of wavelengths of the electromagnetic spectrum shall provide a solution to the following equations to an acceptable level of precision. This is accomplished by solving the following equations to determine the respective concentrations of the ingredients in the calibration sample mixtures using (i) an arbitrarily selected number of wavelengths within the range of wavelengths, (ii) the lowest standard deviation among the average k values as determined from the data files for the individual calibration samples as set forth in Tables I, II, and III, and (iii) the singular value decomposition mathematical technique to determine which of the arbitrarily selected number of wavelengths (scan range) provide the lowest chi-squared statistic between calculated and known values of the concentration of ingredients in the calibration sample mixtures.

$A_1 = k_{11}c_1 + k_{12}c_2 + k_{13}c_3 + k_{1n}c_n$ $A_2 = k_{21}c_1 + k_{22}c_2 + k_{23}c_3 \ldots k_{2n}c_n$ $A_3 = k_{31}c_1 + k_{32}c_2 + k_{33}c_3 \ldots k_{3n}c_n$ $A_n = k_1c_1 + k_2c_2 + k_3c_3 \ldots k_nc_n$ $A_m = k_{m1}c_1 + k_{m2}c_{c2} + k_{m3}c_3 \ldots k_{mn}c_n$ where $A_1, A_2, A_3 \ldots A_n$ are the values of the absorbance measurements at said arbitrarily selected wavelengths, $k_{m1}, k_{m2}, k_{m3} \ldots k_{mn}$ are the average k values from the data files for the individual calibration samples which most closely correspond to the k values for the concentration of ingredients in the calibration sample mixtures (the first subscript is the wavenumber and the second matches the subscript for the unknown chemical species being determined), and $c_1, c_2, c_3 \ldots c_n$ are the concentrations (either known or unknown) expressed in molar units, of the ingredients in the sample mixtures.

Figure 6:
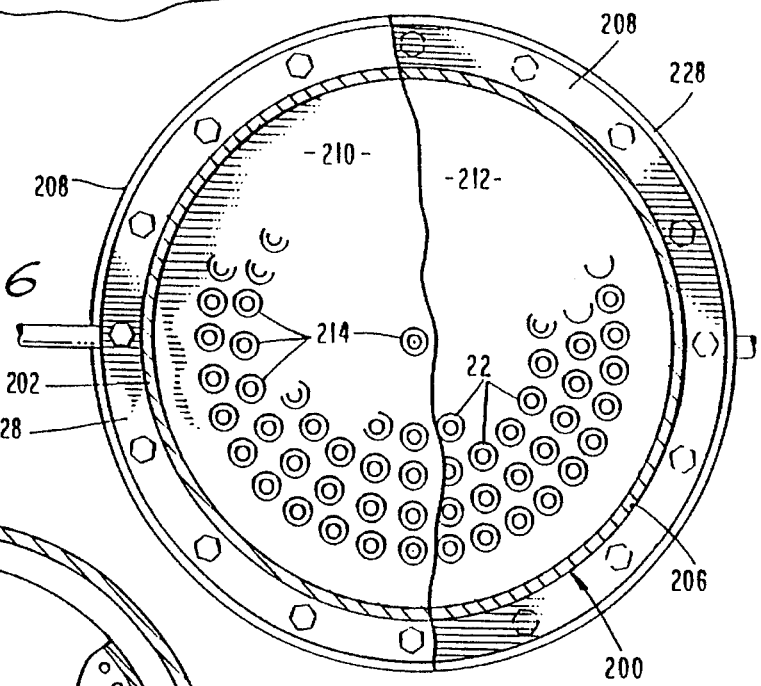
FIG. 6 is a sectional view taken along line 6—6 of FIG. 3.

FIGS. 5' and 6' are illustrative of these later steps of the method. FIG. 5' is the spectra over a wavenumber range between 900 and 1150 for a calibration sample mixture of 2.5% sucrose, 0.59% glucose, and 0.30% fructose. Concentrations of ingredients in the calibration samples were determined using k values from the data files of 3% sucrose, 0.5% glucose, and 0.25% fructose aqueous solutions over a scan range of 1114–1032 wavenumber. FIG. 6' is similar to FIG. 5' except for the very important difference that the scan range was 1114–902 wavenumber rather than 1114–1032 wavenumber. Calculated results (dotted line) and actual reading (solid line) from the FT-IR instrument are displayed together. In FIG. 5' the calculated values match more closely to the actual reading than in FIG. 6'. Therefore, the scan range of 1114–1032 wavenumber is used to determine unknown concentrations in a sample stream from the process.

ON-LINE MONITORING OF CHEMICAL PROCESS

Figure 7:
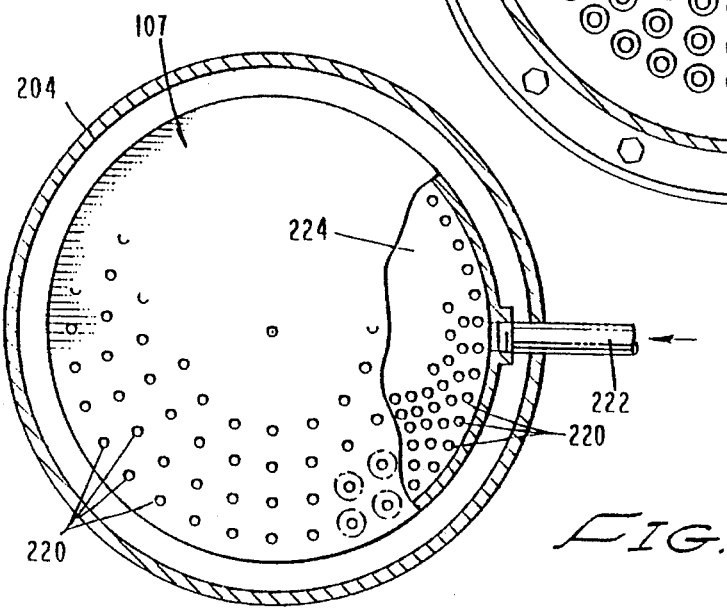
FIG. 7 is a sectional view taken along line 7—7 of FIG. 3.

Using the data files created for the calibration samples and calibration mixture samples, the reactants and products (sucrose, glucose, and fructose) of chemical process shown in FIG. 1' are monitored by measuring the spectra of a sample stream from the process. This spectra is shown in FIG. 7'. First, the chemical process is continually monitored to collect individual samples in which the concentration of ingredients is unknown and the electromagnetic absorption of each individual samples is measured over the scan range which provided the lowest chi-squared statistic between calculated and known values of the concentration of ingredients in the calibration sample mixtures.

Second, the following equations are solved in accordance with singular value decomposition mathematical technique to determine the respective unknown concentrations of the ingredients in the test samples using the average k values at the wavenumbers determined above. Specifically, the following equations are solved at 1114–1032 wavenumbers.

$A_1 = k_{11}c_1 + k_{12}c_2 + k_{13}c_3 \ldots k_{1n}c_n$ $A_2 = k_{21}c_1 + k_{22}c_2 + k_{23}c_3 \ldots k_{2n}c_n$ $A_3 = k_{31}c_1 + k_{32}c_2 + k_{33}c_3 \ldots k_{3n}c_n$

.

.

.

$A_m = k_{m1}c_1 + k_{m2}c_2 + k_{m3}c_3 + \ldots + k_{mn}c_n$ where $A_1, A_2, A_3 \ldots A_n$ are the values of the absorbance measurements of the test samples (the abscissa of FIG. 7'), $k_{m1}, k_{m2}, k_{m3} \ldots k_{mn}$ are the k values from Tables I, II, and III, and $c_1, c_2, c_3 \ldots c_n$ are the concentrations expressed in molar units of the unknown ingredients in the test samples, in this case, four values representing sucrose, glucose, fructose, and water.

Forth, the second step is repeated using k values which corresponds most closely to the k value for the concentration of the unknown ingredient as determined in the second step.

Fifth, using the concentration of ingredients as determined in the forth step calculate the absorption of the test sample and compare the calculated absorption with the actual measured absorption. The forth and fifth steps are repeated until the values of k used in determining the unknown concentrations of ingredients in the test samples provide the statistically best results. Specifically, repetition is mandated so that the results obtained in repeated calculations of the unknown concentrations of ingredients in the test samples have a percentage deviation of less than about 1 percent. When this is achieved the concentration of unknown ingredients has been determined with the desired accuracy.

Table IV presents two sets of calculated values for an unknown mixture using the k values for two different mixtures:

TABLE IV

| (Unknown Sucrose, Glucose, Fructose Solution) | | | |
|---|---|---|---|
| MIXTURE 1 Using k file 3% Suc, 0.5% Glu, .25% Fru | | MIXTURE 2 Using k file 1% Suc, 0.5% Glu, .25% Fru | |
| Mass % | Mole % | Mass % | Mole % |
| Sucrose 1.99 | 0.108 | 2.00 | 0.108 |
| Glucose 0.48 | 0.049 | 0.45 | 0.046 |
| Fructose 0.36 | 0.037 | 0.35 | 0.036 |
| Chi-Square Value | 2.3 | | 4.5 |

In TABLE IV, the MIXTURE 1 comprises 3.0 weight % sucrose, 0.5 weight % glucose, and 0.25 eight % fructose, and MIXTURE 2 comprises 3.0 weight % sucrose, 0.5 weight % glucose, and 0.25% fructose. The results are expressed as mole percent (as mole fractions are used in the calculations) as well as in the more usual engineering units of mass percent. The method of the invention obtained the results using the k files corresponding to mixture two with a Chi-square value of 4.5 and the results using the k files corresponding to mixture 1 with a Chi-square value of 2.5. These were the last two iterations zeroing in on the best values for the unknown concentrations at the desired level of precision (better than 0.1%). The results are taken corresponding to the answers given by the k files associated with mixture 1 because the Chi-square value is lowest.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. (For the purposes of this invention absorbance and transmission and wavelength and wavenumbers are equivalent terms, and light and electromagnetic radiation are equivalent terms.) Consequently, it is not the invention to limit this invention to the particular embodiment disclosed. On the contrary, the intention is to cover all modifications and alternate constructions coming within the spirit and scope of the invention as generally expressed by the following claims:

We claim:

1. A process for growing living cellular material comprising of the steps of:

a) placing live cells in a reaction zone including a membrane in contact with an aqueous medium, said membrane selected to pass unwanted metabolites from the reaction zone into the aqueous medium, b) maintaining conditions within the reaction zone to promote rapid growth of the live cells, c) feeding an aqueous nutrient to the live cells inside the reaction zone, with the cells digesting a portion of the nutrient and a portion of the nutrient passing through the membrane, d) withdrawing the cells from the reaction zone and metabolites from the aqueous medium at a controlled rate, and e) measuring on a real time, on-line basis either directly or indirectly the concentration of nutrient in the reaction zone and regulating on a real time basis the rate at which the nutrient is feed to the reaction zone as a function of said concentration.

2. The process of claim 1 where the aqueous nutrient feed is pulsed.

3. The process of claim 1 where the aqueous nutrient feed is feed continuously at different rates.

4. The process of claim 1 where the the number of cells within the reaction zone is maintained in the range of from $10^2$ to $10^{10}$ cells per milliliter.

5. The process of claim 1 where the cells are withdrawn from the reaction zone at a rate to maintain the live cells in the reaction zone at a concentration range of from $10^2$ to $10^7$ cells per milliliter.

6. The process of claim 1 wherein the conditions within the reaction zone are anaerobic or aerobic.

7. The process of claim 1 wherein the aqueous medium is water or a dilute aqueous nutrient solution utilizing some of the same ingredients as the nutrient solution but containing from 10 to 50 times more water than the concentrated nutrient solution.

8. The process of claim 1 wherein the membrane has an exclusion range of from 500 to 1,000,000 Daltons.

9. The process of claim 8 wherein the membrane is in the form of a container which floats on the aqueous medium.

10. The process of claim 8 wherein the membrane is in the form of a tubular membrane has a length of from 1 to 8 feet, and a diameter of from 0.25 to 3.0 inches.

11. The process of claim 1 wherein the number of cells within the reaction zone are maintained essentially constant under equilibrium conditions.

12. The process of claim 1 wherein a portion of the cells are withdrawn from the reaction zone before they reach a size that interferes with proper operation process equipment.

13. The process of claim 1 wherein the metabolites concentration in the aqueous medium is measure on a real time, on-line basis and the rate of withdrawal of metabolites from said aqueous medium is regulated on a real time, on-line basis as a function of said concentration.

14. The process of claim 1 wherein a general purpose computer and an electromagnetic absorption or reflection instrument are used to determine the concentrations of nutrient solution in the reaction zone and the aqueous medium, comprising (I) first creating data files by (a) preparing a number of calibration samples at different concentrations spanning the concentration range of interest for each individual ingredient being monitored, (b) measuring the electromagnetic absorption of the calibration samples at a selected number of different wavelengths over a predetermined range of wavelengths of the electromagnetic spectrum and storing the measurements in a data file in the memory of the computer, (c) repeating steps (a) and (b) a sufficient number of times to obtain statistically significant data composed of these absorbance measurements for the known concentrations of each of the ingredients and storing said data in a data file in the memory of the computer, (d) using the following equation $$k = \frac{A - k_{solvent}(1.0 - c)}{c}$$

where

A is the absorbance measurement of each individual calibration sample, and c is the concentration in molar units of the ingredient in the calibration sample, $k_{solvent}$ (for liquids and solids) is the absorbance value of the component designated as a solvent in which the other components are distributed measured in its pure form, calculating for each calibration sample an average k value at each of said selected number of different wavelengths over said predetermined range of wavelengths, and a standard deviation value thereof, and storing said calculated k values and standard deviation values thereof in a data file in the memory of the computer, (e) preparing a plurality of calibration sample mixtures of the ingredients at known concentrations and measuring the electromagnetic absorption of the calibration sample mixtures at each wavelength within said range of wavelengths of the electromagnetic spectrum, (f) determining which wavelength within said range of wavelengths of the electromagnetic spectrum shall provide a solution to the following equations to an acceptable level of precision by solving said following equations to determine the respective concentrations of the ingredients in the calibration sample mixtures using (i) an arbitrarily selected number of wavelengths within said range of wavelengths, (ii) the lowest standard deviation among the average k values as determined in step (d), and (iii) the singular value decomposition mathematical technique to determine which of the arbitrarily selected number of wavelengths provide the lowest chi-squared statistic between calculated and known values of the concentration of ingredients in the calibration sample mixtures $$A_1 = k_{11}c_1 + k_{12}c_2 + k_{13}c_3 \ldots k_{1n}c_n$$

$$A_2 = k_{21}c_1 + k_{22}c_2 + k_{23}c_3 \ldots k_{2n}c_n$$

$$A_3 = k_{31}c_1 + k_{32}c_2 + k_{33}c_3 \ldots k_{3n}c_n$$

.

.

.

$$A_m = k_{m1}c_1 + k_{m2}c_2 + k_{m3}c_3 + \ldots + k_{mn}c_n$$

where $A_1, A_2, A_3 \ldots A_n$ are the values of the absorbance measurements at said arbitrarily selected wavelengths, $k_{m1}, k_{m2}, k_{m3} \ldots k_n$ are the average k values from step (d) which most closely correspond to the k values for the concentration of ingredients in the calibration sample mixtures for each wavenumber or wavelength, and $c_1, c_2, c_3 \ldots c_n$ are the concentrations(either known or unknown) expressed in molar units, of the ingredients in the sample mixtures, (II) second conducting on-line monitoring by (i) continually sampling the chemical process to collect individual samples in which the concentration of ingredients is unknown and measuring the electromagnetic absorption of said individual samples at the arbitrarily selected number of wavelengths which provide the lowest chi-squared statistic between calculated and known values of the concentration of ingredients in the calibration sample mixtures as determined in step (f), (j) solving the following equations in accordance with singular value decomposition mathematical technique to determine the respective unknown concentrations of the ingredients in the samples taken in step (i) using the average k values at the wave lengths determined in step (f)

$$A_1 = k_{11}c_1 + k_{12}c_2 + k_{13}c_3 \ldots k_{1n}c_n$$

$$A_2 = k_{21}c_1 + k_{22}c_2 + k_{23}c_3 \ldots k_{2n}c_n$$

$$A_3 = k_{31}c_1 + k_{32}c_2 + k_{33}c_3 \ldots k_{3n}c_n$$

.

.

.

$$A_m = k_{m1}c_1 + k_{m2}c_2 + k_{m3}c_3 + \ldots + k_{mn}c_n$$

where $A_1, A_2, A_3 \ldots A_n$ are the values of the absorbance measurements taken in step (i), $k_{m1}, k_{m2}, k_{m3} \ldots k_n$ are the k values from step (d) at each wavenumber or wavelength n, and $c_1, c_2, c_3 \ldots c_n$ are the concentrations expressed in molar units of the unknown ingredients in the samples, (k) repeating step (j) using k values which corresponds most closely to the k value for the concentration of the unknown ingredient as determined in step (j), (l) using the concentration of ingredients as determined in step (k), calculating absorption of the unknown sample and comparing said calculated absorption with the actual measured absorption, and (m) repeating steps (k) and (l) until the statistically best values of k used in determining the concentrations of unknown ingredients so that the results obtained in repeated calculations of the unknown concentrations of ingredients in the samples have a percentage deviation of less than about 1 percent.

15. The process of claim 14 where real time measurements are conducted on-line to control said process by monitoring the concentrations of nutrient in the reaction zone and aqueous medium, and altering the rate of feeding nutrient to the reaction zone as determined by absorption data taken with a spectrometric instrument and using a general purpose computer to adjust said rate of feeding nutrient.

16. The process of claim 1 where said process is monitored and controlled by (a) measuring the concentration of nutrient in samples from the process using a spectrometric instrument to obtain spectral data characteristic of nutrient components, (b) analyzing the spectral data using a chi-squared mathematical technique to determine the unknown concentration of nutrient components in said samples, and (c) altering the rate at which nutrient is fed to the reaction zone based on the determination of concentration of nutrient components in step (b) as required to optimize the process.

* * * * *